(12) United States Patent
Sanders et al.

(10) Patent No.: US 8,754,133 B2
(45) Date of Patent: *Jun. 17, 2014

(54) COMPOUNDS, COMPOSITIONS AND METHODS FOR THE TREATMENT OF INFLAMMATORY DISEASES

(75) Inventors: Virginia Sanders, San Francisco, CA (US); Joel Cummings, Seattle, WA (US); Alan D Snow, Lynnwood, WA (US)

(73) Assignee: ProteoTech, Inc., Kirkland, WA (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/268,170

(22) Filed: Oct. 7, 2011

(65) Prior Publication Data

US 2012/0058998 A1    Mar. 8, 2012

Related U.S. Application Data

(63) Continuation-in-part of application No. 12/475,097, filed on May 29, 2009, now abandoned, and a continuation-in-part of application No. 10/077,596, filed on Feb. 15, 2002, now abandoned, and a continuation-in-part of application No. 10/053,625, filed on Nov. 2, 2001, now Pat. No. 6,929,808, and a continuation of application No. 13/188,636, filed on Jul. 22, 2011, now abandoned, and a continuation-in-part of application No. 12/837,721, filed on Jul. 16, 2010, now Pat. No. 8,163,957, and a continuation of application No. 12/269,017, filed on Nov. 11, 2008, now abandoned, and a continuation of application No. 10/452,851, filed on May 30, 2003, now Pat. No. 7,514,583.

(60) Provisional application No. 60/385,144, filed on May 31, 2002, provisional application No. 60/409,100, filed on Sep. 9, 2002, provisional application No. 60/412,272, filed on Sep. 20, 2002, provisional application No. 60/435,880, filed on Dec. 20, 2002, provisional application No. 60/463,104, filed on Apr. 14, 2003.

(51) Int. Cl.
*A61K 31/12* (2006.01)
*A61K 31/135* (2006.01)
*A61K 31/075* (2006.01)
*A61K 31/05* (2006.01)

(52) U.S. Cl.
USPC ........... 514/679; 514/649; 514/717; 514/733; 514/734

(58) Field of Classification Search
None
See application file for complete search history.

(56) References Cited

U.S. PATENT DOCUMENTS

| | | | |
|---|---|---|---|
| 2,769,817 A * | 11/1956 | Martin et al. | 549/446 |
| 3,536,809 A | 10/1970 | Applezweig | 424/28 |
| 3,598,123 A | 8/1971 | Zaffaroni et al. | 424/20 |
| 3,845,770 A | 11/1974 | Theeuwes et al. | 424/15 |
| 3,916,899 A | 11/1975 | Theeuwes et al. | 128/280 |
| 4,008,719 A | 2/1977 | Theeuwes et al. | 128/260 |
| 4,710,384 A | 12/1987 | Rotman | 424/465 |
| 4,844,901 A | 7/1989 | Keplinger et al. | 424/195.1 |
| 4,940,725 A | 7/1990 | Keplinger et al. | 514/411 |
| 5,059,595 A | 10/1991 | LeGrazie | 424/468 |
| 5,061,629 A | 10/1991 | Coffen et al. | 435/280 |
| 5,073,543 A | 12/1991 | Marshall et al. | 514/21 |
| 5,120,548 A | 6/1992 | McClelland et al. | 424/473 |
| 5,166,139 A | 11/1992 | Bombardelli et al. | 514/26 |
| 5,166,180 A | 11/1992 | Jenkins | |
| 5,302,611 A | 4/1994 | Keplinger et al. | 514/411 |
| 5,354,556 A | 10/1994 | Sparks et al. | 424/9 |
| 5,478,579 A | 12/1995 | Sawruk | 424/535 |
| 5,591,767 A | 1/1997 | Mohr et al. | 514/413 |

(Continued)

FOREIGN PATENT DOCUMENTS

EP    0 324 521 A2    7/1989
EP    0 515 128 A1    5/1992

(Continued)

OTHER PUBLICATIONS

Calis et al. "Flavunoid, Iridiod, and Lignan Glycosides from *Putoria calabrica*," J. Nat. Prod 64:961-964 (2001).

(Continued)

*Primary Examiner* — Sreeni Padmanabhan
*Assistant Examiner* — Jody Karol
(74) *Attorney, Agent, or Firm* — Rebecca Eagen

(57) ABSTRACT

A method of inhibiting the inflammatory process, the method comprising administering to a mammal suffering from inflammation a therapeutically effective amount of a pharmaceutical composition comprising a compound

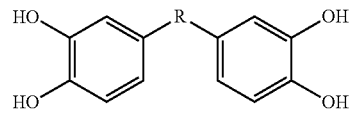

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by $NR^1$ (where $R^1$ is H, alkyl, or acyl), O, or S; and 1 or 2 methylene groups are optionally replaced by a carbonyl or hydroxymethylene group and pharmaceutically acceptable esters or salts of the compounds and wherein the inflammatory process results from a disease selected from the group consisting of ulcerative colitis, endotoxic shock, rheumatoid arthritis, juvenile arthritis, osteoarthritis, psoriasis, Crohn's disease, inflammatory bowel disease, multiple sclerosis, insulin dependent diabetes mellitus, gout, psoriatic arthritis, reactive arthritis, vital or post-viral arthritis and ankylosing spondylarthritis.

9 Claims, No Drawings

(56) References Cited

U.S. PATENT DOCUMENTS

| | | | |
|---|---|---|---|
| 5,639,476 A | 6/1997 | Oshlack et al. | 424/468 |
| 5,643,562 A | 7/1997 | Kisilevsky et al. | 424/78.31 |
| 5,674,533 A | 10/1997 | Santus et al. | 424/493 |
| 5,681,569 A | 10/1997 | Kuznicki et al. | 424/195 |
| 5,703,129 A | 12/1997 | Felsenstein et al. | 514/613 |
| 5,726,375 A | 3/1998 | Kislievsky et al. | 424/78.31 |
| 5,733,566 A | 3/1998 | Lewis | 424/426 |
| 5,767,126 A | 6/1998 | Marchbanks | 514/297 |
| 5,869,469 A | 2/1999 | Szarek | 514/120 |
| 5,958,883 A | 9/1999 | Snow | 514/16 |
| 5,972,956 A | 10/1999 | Hays et al. | 514/297 |
| 5,981,168 A | 11/1999 | Reiner | 435/4 |
| 6,037,327 A | 3/2000 | Castillo et al. | 514/23 |
| 6,039,949 A | 3/2000 | Pero | 424/195.1 |
| 6,165,912 A | 12/2000 | McConnell et al. | 438/758 |
| 6,207,842 B1 | 3/2001 | Romanczyk et al. | 549/399 |
| 6,264,994 B1 | 7/2001 | Castillo et al. | 424/725 |
| 6,297,281 B1 | 10/2001 | de Lassauniere et al. | 514/589 |
| 6,340,783 B1 | 1/2002 | Snow | 800/12 |
| 6,346,280 B1 | 2/2002 | Castillo et al. | 424/725 |
| 6,432,636 B1 | 8/2002 | Maresh et al. | 435/6 |
| 6,563,016 B1 | 5/2003 | Snow et al. | 800/12 |
| 6,607,758 B2 | 8/2003 | Castillo et al. | 424/769 |
| 7,514,583 B2 | 4/2009 | Snow et al. | 564/179 |
| 7,601,876 B2 | 10/2009 | Snow et al. | 568/331 |
| 7,714,170 B2 | 5/2010 | Snow et al. | 568/331 |
| 7,763,747 B2 * | 7/2010 | Snow et al. | 560/250 |
| 8,163,957 B2 * | 4/2012 | Snow et al. | 564/155 |
| 2001/0047032 A1 | 11/2001 | Castillo et al. | 514/453 |
| 2002/0088067 A1 | 7/2002 | Choi et al. | 424/729 |
| 2002/0111309 A1 | 8/2002 | Castillo et al. | 514/12 |
| 2002/0119934 A1 | 8/2002 | Castillo et al. | 514/23 |
| 2002/0150637 A1 | 10/2002 | Castillo et al. | 424/730 |
| 2002/0150948 A1 | 10/2002 | Castillo et al. | 435/7.1 |
| 2002/0151506 A1 | 10/2002 | Castillo et al. | 514/27 |
| 2002/0168753 A1 | 11/2002 | Castillo et al. | 435/226 |
| 2002/0197692 A1 | 12/2002 | Castillo et al. | 435/184 |
| 2003/0013648 A1 | 1/2003 | Castillo et al. | 514/12 |
| 2003/0017998 A1 | 1/2003 | Snow et al. | 514/27 |
| 2003/0153734 A1 | 8/2003 | Castillo et al. | 530/370 |
| 2004/0127555 A1 | 7/2004 | Snow et al. | 514/464 |

FOREIGN PATENT DOCUMENTS

| | | |
|---|---|---|
| EP | 0 659 418 A1 | 6/1995 |
| EP | 1 014 996 B1 | 5/2003 |
| JP | 1-151514 | 6/1989 |
| JP | 1151514 | 6/1989 |
| JP | 10-175852 | 6/1998 |
| JP | 10-175854 | 6/1998 |
| JP | 10-245342 | 9/1998 |
| JP | 2001-341424 | 12/2001 |
| WO | 90/00047 | 1/1990 |
| WO | 9628187 | 9/1996 |
| WO | 97/46664 | 12/1997 |
| WO | 9746664 | 12/1997 |
| WO | 98/08381 | 3/1998 |
| WO | 98/09653 | 3/1998 |
| WO | 9809653 | 3/1998 |
| WO | 9815178 | 4/1998 |
| WO | 98/34646 | 8/1998 |
| WO | 9834646 | 8/1998 |
| WO | 98/39653 | 9/1998 |
| WO | 9839653 | 9/1998 |
| WO | 98/51302 | 11/1998 |
| WO | 9851302 | 11/1998 |
| WO | 99/09999 | 3/1999 |
| WO | 9909999 | 3/1999 |
| WO | 9945947 | 9/1999 |
| WO | 99/61013 | 12/1999 |
| WO | 00/12102 | 3/2000 |
| WO | 0012102 | 3/2000 |
| WO | 0030666 | 6/2000 |
| WO | 0033659 | 6/2000 |
| WO | 0055187 | 9/2000 |
| WO | 00/57707 | 10/2000 |
| WO | 0057707 | 10/2000 |
| WO | 01/21160 | 3/2001 |
| WO | 01/49281 | 7/2001 |
| WO | 01/49307 | 7/2001 |
| WO | 0149301 | 7/2001 |
| WO | 01/55115 | 8/2001 |
| WO | 0156567 | 8/2001 |
| WO | 0241842 | 5/2002 |
| WO | 0242329 | 5/2002 |
| WO | 02/47679 | 6/2002 |
| WO | 02/062422 | 8/2002 |
| WO | 02/076381 | 10/2002 |
| WO | 02076381 | 10/2002 |
| WO | 03/053425 | 7/2003 |
| WO | 2004/006906 | 1/2004 |

OTHER PUBLICATIONS

Castillo and Templeton, "Structure and metabolism of multiple heparin sulphate proteoglycans synthesized by the isolated rat glomerulus", Biotechimica et Biophysica Acta, 1136:119-128 (1992).

Castillo and Templeton, "Subunity structure of bovine ESF (extracellular-matrix stabilizing factor(s)) a chondroitin sulfate proteoglycan with homology to human Iai (inter-α-trypsin inhibitors". FEBS. 318(3):292-296 (1993).

Clark et al. "Islet Amyloid. Increased A-Cells. Reduced B-Cells and Exocrin Fibrosis: Quantitative Changes in the Pancreas in Type 2 Diabetes," Diabetes Res. 9:151-159 (1988).

Czochanska et al. "Direct Proof of a Homogenous Polyflan-3-ol Structure for Polymeric Proanthocyanidins," J.C. Chem. Comm. 3 375-377 (1979).

Derwent World Patents Index, Dialog File No. 351 Accession No. 12134240:JP 10245342A "Agent for Reducing Cell Toxicity of Beta-Amyloid Protein—Contains Tea Polyphenol" (1998).

Derwent World Patents Index, Dialog File No. 351 Accession No. 8128744, WO 9000047 "Hari Dye Contg. Oxidn. Dye Precursor Developer—and Dihydroxyhenzamide Deriv as Coupler" (1990).

Ferreira et al. "Tetrahedron Report No. 308: Diversity of Structure and Function in Oligomeric Flavanoid" Tetrahedron 48:1743-1803 (1992).

Fletcher et al. "Plant Proanthocyanidins Part 3. Conformational and Configurational Studies of Natural Procyanidins" JCS Perkin 1:1628-1637 (1977).

Gujer et al. "Gluosylated Flavonoids and other Phenolic Compounds From Sorghum" Phytochemistry 25:1431-1436 (1986).

Hashimoto et al. "Tannins and related Compounds. XC. 8-C-Ascorbyl (−)-Epigallocatechin. 3-)-Gallate and novel dimeric Flavin-3-ols. Oolonghomobistlavans A and B from Oolong tea", Chem Pharm Bull 37(12) 3255-3263 (1989).

Hemingway et al. "Linkage Isomerism in Trimeric and Polymeric 2,3-cis-Procyanidins" J. Chem . Soc. Perkins Trans. 1:1209-1216 (1982).

Ho et al. "Phytochemicals in Teas and Rosemary and Their Cancer-Preventive Propertis" ACS Symp. Ser. (Food Phytochemicals for Cancer Prevention II) vol. 547:2-19 (1994).

Hsaio et al. "Age-related CNS Disorder and early death in transgenic FVB/N mice overexpressing alsheimer amyloid precursor proteins", Neuron, vol. 15: 1203-1218 Nov. 1995.

Ishimaru et al "Flavin-2-ol and Procyanidin Glycosides from *Quercus Miyagii*" Phytochemistry 26:1167-1170 (1987).

Jain et al. "Antiinflammatory Effects of an Ayurvedic Preparation. Brahmi Rasayan. in Rodents" Indian Journal of Experimental Biology. 32:633-636 (1994).

Jones et al, "The Condensed Tannins of Pasture Legume Species" Photochemistry, 15:1407-1409 (1976).

Kashiwada et al. "Tannins and Related Compounds. XCII, Occurance of Enantiomeric Proanthocyanidins in the Leguminosae Plants. *Cassia fistula* L., and *C. javanica* L.,", Chem. Pharm. Bull. 38:888-893 (1990).

Kim et al. "Neuroprotective Constituents from *Hedyotis diffusa*," J. Nat. Prods. 64:75-78 (2001).

(56) References Cited

OTHER PUBLICATIONS

Cunnane et al., "Amyloid prescursors and amyloidosis in rheumatoid arthritis," Balliére's Clinical Rheumatology, (1999) vol. 13, No. 4; pp. 615-628.
"Progress Report on Alzheimers Disease," The National Institute on Aging, National Institutes of Health, 1997.
Arai et al, "Argyrophilic glial inclusions in the midbrain of patients with Parkinson's disease and diffuse Lewy body disease are immunopositive for NACP/α-synuclein," *Neurosc. Lett.* 259:83-86 (1999).
Barner et al. "Donepezil Use in Alzheimer Disease," The Annals of Pharmacotherupy, 32:70-77 (1998).
Baumann et al, "A simple isolation method for the major catechins in green tea using high-speed countercurrent chromatography," *J. Natural Prod.* 64:353-355, (2001).
Benson et al. "Serum Amyloid a Protein in Amyloidosis, Rheumatic, and Neoplastic Diseases," *Arthritis and Rheumatism*, 22(1): 36-42, (1979).
Braquet et al. "Ethnopharmacology and the Development of Natural PAF Antagonists as Therapeutic Agents," *Journal of Ethnopharmacology*, 32:135-139, (1991).
Calis et al, "Flavonoid, Iridoid, and Lignan Glycosides from *Putoria calabrica*," *J. Nat. Prod.* 64:961-964, (2001).
Castillo and Templeton, "Structure and metabolism of multiple heparan sulphate proteoglycans synthesized by the isolated rat glomerulus", *Biochimica et Biophysica Acta*, 1136:119-128 (1992).
Castillo and Templeton, "Subunit structure of bovine ESF (extracellular-matrix stabilizing factor(s)) a chondroitin sulfate proteoglycan with homology to human Iαi (inter-α-trypsin inhibitors,", *FEBS*, 318(3): 292-296 (1993).
Castillo et al. "Sulfate content and specific glycosaminoglycan backbone of perlecan are critical of perlecan't enhancement of islet amyloid polypeptide (Amylin) Fibril formation." *Diabetes*, 47: 612-620, (1998).
Castillo et al., "Laminin inhibition of beta-amyloid protein (A beta) fibrillogenesis and identification of an A beta binding site localized to the globular domain repeat on the laminin a chain", *J. Neurosci. Res.*, 62(3):451-462 (2000).
Castillo et al., "The sulfate moieties of glycosaminoglycans are critical for the enhancement beta-amyloid protein fibril formation", *J. Neurochem.*, 72(4):1681-1687 (1999).
Castillo. "Novel Purification and detailed characterization of perlecan isolated from the engelbreth-holm-swarm tumor for use in an animal model of fibrillar AB amyloid persistence in brain." *J. Biochem.* 120(2):433-444, (1996).
Castillo. "Perlecan Binds to the β-amyloid proteins (Aβ) of alzheimer's desiase, Accelerates Aβ fibril formation, and Maintains Aβ fibril Stability."*Journal of Neuochemistry*, 69(6): 2452-2465, (1997).
Clark et al, "Islet Amyloid, Increased A-Cells, Reduced B-Cells and Exocrine Fibrosis: Quantitative Changes in The Pancreas in Type 2 Diabetes," *Diabetes Res.* 9:151-159, (1988).
Conway et al., "Accelerated in vitro fibril formation by a mutant α-synuclein linked to early-onset Parkinson disease," *Nature Med.* 4:1318-1320, (1998).
Cooper et al. "Purification and characterization of a peptide from amyloid-rich pancreases of type 2 diabetic patients." *Proc. Natl. Acad. Sci. USA*, 84:8629-8632, (1987).
Crutcher et al., "Cellular and molecular pathology in Alzheimer's disease", *Hippocampus*, 3:271-287 (1993).
Cutler et al. "Correspondence: Tacrine in Alzheimers Disease," *The New England Journal of Medicine*, pp. 808-810, (Mar. 18, 1993.).
Czochanska et al, "Direct Proof of a Homogeneous Polyflavan-3-ol Structure for Polymeric Proanthocyanidins," *J.C. S. Chem. Comm.* pp. 375-377, (1979).
Derwent Abstract, Accession No. 7950380 citing JP 1151514 published Jun. 14, 1989, "Compsns. for treating and preventing nervous diseases—contains carboxylic acid, pref. genic or pyrogallol-4-carboxylic acid, esp. useful fro alzheimers disease—contains carboxylic acid, pref. gallic or pyrogallol-4-carboxylic acid, esp. useful for alzheimers disease."
Ferreira et al, "Tetrahedron Report No. 308: Diversity of Structure and Function in Oligomeric Flavanoid," *Tetrahedron* 48:1743-1803, (1992).
Fletcher et al, "Plant Proanthocyanidins. Part 3. Conformational and Configurational Studies of Natural Procyanidins," *JCS Perkin* 1:1628-1637, (1977).
Flood et al. "Amnestic effects in mice of four synthetic peptides homologous to amyloid B protein from patients wit alzheimer disease." *Proc. Natl. Acad. Sci. USA*, 88:3363-3366 (1991).
Flood et al. "An amyloid β-protein fragment, Aβ[12-18], equipotently impairs post-training memory processing when injected into different limbic system structures." *Brain Research* 663:271-276 (1994).
Fraser et al., "Conformation and fibrillogenesis of Alzheimer A beta peptides with selected substitution of charged residues", *J. Mol. Biol.*, 244(1):64-73 (1994).
Fukuchi et al., "Increased expression of beta-amyloid protein precursor and microtubule-associated protein tau during the differentiation of murine embryonal carcinoma cells", *J. Neurochem.*, 58(5):1863-1873 (1992).
Games et al. "Alzheimer-type neuopathology in transgenic mice overexpressing V717F B-amyloid precursor protein." *Nature*, 373: 523-527 (1995).
Gejyo et al. "A New Form of Protein Associated with Chronic Hemodialysis was Identified as B2 Metroglobulin ," *Biochemical and Biophysical Research Communications*, 129(3): 701-706, (1985).
Gejyo et al. "β2-Metroglobulin: A New Form of Protein Associated with Chronic Hemodialysis," *Kidney International*, 30:385-590 (1986).
Glenner et al. "Alzheimer's Disease: Initial Report of the Purification and Characterization of a Novel Cerebrovascular Amyloid Protein," *Biochemical and Biophysical Research Communications*, 120(3): 885-890 (1984).
Grundke-Iqbal et al. "Abnormal Phosphorylation of the Microtubule-Associated Protein Tau Alzheimer Cytoskeletal Pathology," *Proc. Nati. Acad. Sci. USA*, 83:4913-4917 (1986).
Gujer et al, "Glucosylated Flavonoids and Other Phenolic Compounds From Sorghum," *Phytochemistry* 25:1431-1436 (1986).
Haass et al. "The modish mutation causes early-onset alzheimer's disease by β-secretase cleavage with in the secretory pathway." *Nature Medicine* 1(12):1291-1296 (1995).
Harada et al. "Human Amyloid Protein: Chemical Variability and Homogeneity," *Journal of Histochemistry and Cytochemistry*, 19(1): 1-15 (1970).
Hardy et al., "Framing β-amyloid", *Nature Genet.*, 1:233-234 (1992).
Harrigan et al. "Beta Amyloid is Neurotoxic in Hippocampal Slice Cultures," *The Neurobiology of Aging*, 16(5): 779-789, (1995).
Hart et al., "Overproduction of perlecan core protein in cultured cells and transgenic mice", *J. Pathol.*, 194(2):262-269 (2001).
Hashimoto et al., "Human recombinant NACP/α-synuclein is aggregated and fibrillated in vitro: Relevance for Lewy body disease," *Brain Res.* 799:301-306, (1998).
Hertel et al. "Inhibition of the electrostatic interaction between β-amyloid peptide and membranes prevents β-amyloid-induced toxicity," *Proc. Natl. Acad. Sci. USA* 94: 9412-9416 (1997).
Hemingway et al, "Linkage Isomerism in Trimeric and Polymeric 2,3-*cis*-Procyanidins," *J. Chem. Soc. Perkins Trans.* 1:1209-1216 (1982).
Ho et al, "Phytochemicals in Teas and Rosemary and Their Cancer-Preventive Properties," *ACS Symp. Ser. (Food Phytochemicals for Cancer Prevention II*) vol. 547, pp. 2-19 1994.
Hsiao et al. "Age-related CNS Disorder and early death in transgenic FVB/N mice overexpressing alsheimer amyloid precursor proteins." *Neuron*, vol. 15, 1203-1218, Nov. 1995.
Husby et al. "Normenclature of Amyloid and Amyloidosis," *Bulletin of the World Health Organization*, 71(1):105-108, (1993).
Ishimaru et al, :Flavan-2-ol and Procyanidin Glycosides from *Quercus Miyagii, Phytochemistry* 26:1167-1170, (1987).

(56) References Cited

OTHER PUBLICATIONS

Jain et al. "Antiinflammatory Effects clan Ayurvedic Preparation, Brahmi Rasayan, in Rodents," *Indian Journal of Experimental Biology*, 32:633-636 (1994).
Johnson et al. "Islet Amyloid Polypeptide: Mechanisms of Amyloidogenesis in the Pancreatic Islet and Potential Roles in Diabetes Mellitus," *Laboratory Investigation*, 66(5): 522-534, (1992).
Johnson et al. "Islet Amyloid, Islet-Amyloid Polypeptide, and Diabetes Mellitus," *The New England Journal of Medicine*, 321(8): 513-518, (1989).
Jones et al, "The Condensed Tannins of Pasture Legume Species," *Photochemistry*, 15:1407-1409 (1976).
Jucker et al., "Age-related deposition of glia-associated fibrillar material in brains of C57BL/6 mice", *Neuroscience*, 60(4):875-889 (1994).
Kernei et al. "Amyloidosis Associated with Juvenile Rheumatoid Arthritis," *Acta Pathol. Jpn.*, 32(1):23-33 (1982).
Kashiwada et al, "Tannins and Related Compounds. XCIII. Occurnce of Enantiomeric Proanthocyanidins in the Leguminosae Plants, *Cassia fistula* L. and *C.javanica* L.," *Chem. Pharm. Bull.* 38:888-893 (1990).
Kim et al, "Neuroprotective Constituents from *Hedyotis diffusa*," *J. Nat. Prods.* 64:75-78, (2001).
Kitaguchi et al. "Novel Precursor of Alzheimer's Disease Amyloid Protein Shows Protease Inhibitory Activity," *Nature*, 331:530-532, (1988).
Kosik et al. "Microtubule—Associated Protein Tau is a Major Antigenic Component of Pairedd Helicule Filaments in Alzheimer's Disease," *Proc. Natl. Acad. Sci. USA*, 83:4044-4048 (1986).
Krüger et al., "Ala30Pro mutation in the gene encoding α-synuclein in Parkinson's disease," *Nature Genet.* 18:106-108, (1998).
Latimer et al. "71. Inhibitors of Amyloid-β Aggregation: Dimeric Catechols Inhibit Aggregation and Deposition of Aβ," American Chemical Society 221$^{st}$ National Meeting, San Diego, CA Apr. 1-5, 2001 (MEDI 071) [posted on Mar. 23, 2001].
Lee et al. "A68: A Major Subunit of Paired Helical Filaments and Derivatized Forms of Normal Tau," *Science*, 251: 675-678, (1991).
Levine. "Thioflavine T interaction with synthetic alzheimer's disease B-amyloid peptides: Detection of amyloid aggregation in solution." *Protein Science* 2:404-410, (1993).
Levine. "Thioflavine T interacton with amyloid B-sheet structures." *Amyloid: Int. J. Exp. Clin. Invest.* 2:1-6, (1995).
Lorenzo et al, "Pancreatic islet cell toxicity of amylin associated with type-2 diabetes mellitus," *Nature* 368:756-760, (1994).
Mandybur et al. "Cerebral Amyloid Angiopathy: The Vascular Pathology and Complications," *Journal of Neuropathology and Experimental Neurology*, 45(1): 79-90, (1986).
Maresh et al., "Detection and quantitation of perlecan mRNA levels in Alzheimer's disease a normal aged hippocampus by competitive reverse transcription-polymerase chain reaction", *J. Neurochem.*, 67(3):1132-1144 (1996).
Masters et al. "Amyloid Plaque Core Protein in Alzheimers Disease and Down Syndrome," *Proc. Natl. Acad. Sci. USA* 82:4245-4249 (1983).
Matthews et al, "Method for estimation of Proanthocyanidins based on their acid depolymerization in the presence of nucleophiles," *J. Agric. Food Chem.* 45:1195-1201, (1997).
Mattice et al, "Molecular weight averages and $^{13}$C NMR intensities provide evidence for branching in proanthocyanidin polymers," *Phytochem.* 23(6):1309-1311, (1984).
McAdam et al. "Association of Amyloidosis with Erythema Nodosum Leprosum Reactions and Recurrent Neutrophil Leucocytosis in Leprosy," *The Lancet*, pp. 572-576, Sep. 27, 1975.
Metaxas et al. "Familial Mediterranean Fever and Amyloidosis," *Kidney International*, 20:676-685, (1981).
Miller et al., "Localization of perlecan (or a perlecan-related macromolecule) to isolated microglia in vitro and to microglia/macrophages following infusion of beta-amyloid protein into rodent hippocampus", *Gila*, 21(2):228-243 (1997).

Morimoto et al, "Tannins and Related Compounds. LXI Isolation and Structure of Novel Bi- and Triflavanoids from the leaves of *Cassia fistula* L.," *Chem. Pharma. Bull.* 36:39-47, (1988).
Murrell et al. "A mutation in the amyloid recursor protein associated with hereditary alzheimer's disease." Science, 254: 97-99 (1991).
Nahri et al. "Both familial Parkinson's disease mutations accelerate α-Synuclein aggregation." *J. Biol. Chem.* 274:9843-9846 (1999).
Naiki et al. "Kinetic analysis of amyloid Fibril polymerization in vitro." *Laboratory Investigation*, 65(1):104-110, (1991).
Naiki, H. and K. Nakakuki, "First-order kinetic model of Alzheimer's β-amyloid fibril extension in vitro," *Laboratory investigation*, 74(2):374-383 (1996).
Niwano et al., "Inhibitory action of amyloid precursor protein against human Hageman factor (factor XII)," *J. Lab. Clin. Med.* 125:251-6(1995).
Nonaka et al, "Tannins and Related Compound. XV. A New Class of Dimeric Flavan-3-ol Gallates, Theasinensins A and B, and Proanthocyanidin Gallates from Green Tea Leaf. (1)," *Chem. Pharm. Bull.* 31:3906-3914, (1983).
Pardridge et al. "Amyloid Angiopathy of Alzheimer's Disease: Amino Acid Composition and Partial Sequence of a 4,200-Dalton Peptide Isolated from Cortical Microvessels," *Journal of Neurochemisty*, 49(5): 1394-1401, (1987).
Patent Abstracts of Japan citing Japanese Patent 10-245342 published Sep. 14, 1998 , "Agent for reducing neural toxicity of beta-amyoloid protein".
Pike et al. "In Vitro Aging of β-Amyloid Protein Cause Peptide Aggregation and Neurotoxity," *Brain Research*, 563:311-314, (1991).
Pike et al. "Structure-Activity Analyses of β-Amyloid Peptides: Contributions of the β25-35 Region to Aggregation and Neurotoxicity," *Journal of Neurochemistry*, 64(1): 253-265, (1995).
Ponte et al. "A New A4 Amyloid mRNA Contains a Domain Homologous to Serine Proteinase Inhibitors," *Nature*, 31 1:525-527, (1988).
Porter et al, "Isolation of three naturally occuring O-β-glucopyranodsides of procyanidin polymers," *Phytochemistry* 24:567-569, (1985).
Porter, L.J, "Flavans and proanthocyanidins," Chapter 2 in *Flavans and proanthocyanidins—Advances in Research since 1986*, J B Harborne (Ed.) London: Chapman and Hall pp. 23-55, 1994.
Porter,J.J, "Flavans and proanthocyanidins," Chapter 2 in *The Flavanoids—Advances in Research since 1980*, J B Harborne (Ed.), London: Chapman and Hall, pp. 21-62, 1988.
Prieur et al, "Oligomeric and polymeric procyanidins from grape seeds," *Phyochem.* 36:781-784, 1994.
Rogers et al., "Long-term efficacy and safety of donepezil in the treatment of Alzheimer's disease: an interim analysis of the results of a US multicentre open label extension study", *Eur. Neuropsychopharmacol.*, 8:67-75 (1998).
Sang et al, "Iridoid Glycosides from the leaves of *Morinda citrlfolia*,": *J. Nat. Prod.* 64:799-800 (2001).
Santos-Buelga, C. and A. Scalbert, "Proanthocyanidins and tannin-like compounds—nature, occurrence, dietry intake and effects on nutrition and health," *J. Sci.. Food Agri.* 80: 1094-1117, (2000).
Saraiva et al. "Amyloid Fibral Protein in Familial Amyloidotic Polyneurothcrapy, Portugese Type," J. Clin. Invest. 74:104-119 (1984).
Saraiva et al., "Studies on Plasma Transthyretin (Prealbinum) in Familial Amyloidotic Polyneropathy, Portugese Type," J. Lab. Clin. Med. 102(4): 590-603, (1983).
Sekiguchi et al., "Characterization of proteoglycans synthesized by murine embryonal carcinoma cells (P19) reveals increased expression of perlecan (heparan sulfate proteoglycan) during neuronal differentiation", *J. Neurosci. Res.*, 38(6)670-686 (1994).
Skinner et al. "The Prealbinum Nature of the Amyloid Protein in Familial Amyloid Polyneuropathy (FAP)-Swedish Variety," *Biochemical and Biophysical Research Communications*, 99(4):1326-1332, (1981).
Snow et al., "An important role of heparan sulfate proteoglycan (Perlecan) in a model system for the deposition and persistence of fibrillar Aβ-amyloid in rat brain", *Neuron.*, 12(1):219-234 (1994).

(56) References Cited

OTHER PUBLICATIONS

Snow et al., "Differential binding of vascular cell-derived proteoglycans (perlecan, biglycan, decorin, and versican) to the beta-amyloid protein of Alzheimer's disease", *Arch. Biochem. Biophys.*, 320(1):84-95 (1995).
Snow et al., "Heparan sulfate proteoglycan in diffuse plaques of hippocampus but not of cerebellum in Alzheimer's disease brain", *Am. J. Pathol.*, 144(2):337-347 (1994).
Snow et al., "Identification in immunolocalization of a new class of proteoglycan (keratan sulfate) to the neuritic plaques of Alzheimer's disease", *Exp. Neurol.*, 138(2):305-317 (1996).
Snow et al., "In vitro and in vivo models to unravel the potential roles of Flavans and β/A4 in the pathogenesis of Alzheimer's disease", *Hippocampus*, 3(Special Issue):257-268 (1993).
Snow et al., "Peripheral distribution of dermatan sulfate proteoglycans (decorin) in amyloid containing plaques and their presence in neurofibrillary tangles of Alzheimer's disease", *J. Histochem Cytochem.*, 40(1):105-113 (1992).
Snow. "Proteoplycans in the pathogenesis of alzheimer's disease and other amyloidoses." *Neurobiology of Aging*, 10:481-497, (1989).
Spillantini et al., "α-Synuclein in filamentous inclusions in Lewy bodies from Parkinson's disease and dementia with Lewy bodies," *Proc. Natl. Acad. Sci. USA.* 95:6469-6473 (1998).
Stappenbeck et al., "80. Inhibitors of Amyloid-β Aggregation: Histidine Residues in Aβ Play a Crucial Role in Aggregation," American Chemical Society 221$^{st}$ National Meeting, San Diego, CA Apr. 1-5, 2001 (MEDI 080) [posted on Mar. 23, 2001].
Steinberg. "Uncaria Tomentosa (cat's Claw) a wondrous herb from the peruvian rain forest." *Townsend Letter for Doctors*—pp. 442-443, May 1994.
Tamaoka et al. "Amyloid B protein 1-42/43(AB 1-42/43) in crebellar diffuse plaques: enzyme-linked immunosorbent assay and immunocytochemical study." *Brain Research* 67:151-156 (1995).
Tamaoka et al. "Biochemical evedence for the long tail form of amyloid B protein as a seed molecule in cerebral deposits of alzheimer's disease." *Biochemical and biophysical research communications*, 205(1): 834-842, (1994).
Tanzi et al. "Protein Inhibitor Domain Encoded by an Amyloid Protein Precursor mRNA Associated with Alzheimer's Disease," *Nature*, 331:528-532, (1988).
Tawara et al. "Amyloid Fibril Protein in Type 1 Familial Amyloidotic Polyncurotherapy in Japanese," *J. Lab. Clin. Med.*, 98(6): 811-822, (1981).
Thompson et al, "Plant Proanthocyanidins. Part 1. Introduction; the Isolation, Structure, and Distributionin Nature of Plant Procyanidins," *J. Chem. Soc. Perkins Trans.* 1: 1387-1399 (1972).
Tückmantel, "Studies in Potyphenol Chemistry and Bioactivity. 1. Preparation of Building Blocks from (+)-Catechin. Procyanidin Formation. Synthesis of the Cancer Cell Growth Inhibitor, 3-O-Galloyl-(2R,3R)-epicatechin-4β,8-[3-O-Galloyl-(2R,3R)-epicatechin],"*J. Am. Chem. Soc.* 121:12073-12081(1999).
Van Broeckhoven et al. "Amyloid β Protein precursor gene and Hereditary cerebral hemorrage with amyloidosis (Dutch)." *Science*, 248:1120-1122 (1990).
Wirth et al. "Pharmacologically active procyanidines from the bark of *Uncaria tomentosa*." Phytomedicine, vol. 4 (3), pp. 265-266, 1997.
Wood et al., "α-synuclein fibrillogenesis is nucleation-dependent," *J. Biol. Chem.* 274:19509-19512, (1999).
Zhang et al, "Potentillanin, A Biflavanoid and a procyanidin glycoside from potentate viscose," *Phytochemistry* 27:3277-3280, (1988).
English Language Translation of Japanese Patent 10-245342.
Hashimoto et al, "Tannins and related Compounds. XC. 8-C-Ascorbyl(−)-Epigallocatechin 3-)-Gallate and novel dimeric Flavan-3-ols, Oolonghomobisflavans A and B from Oolong tea.", *Chem Pharm. Bull.* 37(12) 3255-3263 (1989).
Hsiao et al., "Correlative Memory Deficits, Aβ Elevation, and Amyloid Plaques in Transgenic Mice," *Science* 274:99-102 (1996).

Kiunk et al., "Quantifying Amyloid β-Peptide (Aβ) Aggregation Using the Congo Red-Aβ (CR-Aβ) Spectrophotometric Assay," *Analytical Biochemistry* 266:66-76 (1999).
Pollanen et al., "Pathology and Biology of the Lewy Body," *Journal of Neuropathology and Experimental Neurology* 52(3):183-191 (1993).
Polymeropoulos et al., "Mutation in the α-Synuclein Gene Identified in Families with Parkinson's Disease", Science, 276:2045-2047 (1997).
Puchtler et al., "On the Binding og Congo Red by Amyloid," *J. Histochem. Cytochem.* 10:355-364 (1962).
Sugita-Konishi et al., "Epigallocatechin gallate and gallocatechin gallate in green tea catechins inhibit extracellular release of Vero toxin from enterohemorrhagic *Escherichia coli* O157:H7," *Biochimica et Biophysica Acta* 1472:42-50 (1999).
Ueda et al., "Molecular cloning of cDNA encoding an unrecognized component of amyloid in Alzheimer 's disease," *Proc. Natl. Acad. Sci. USA* 90:11282-11286 (1993).
Acheson et al., "694. The Synthesis of Some Acylglycines and Related Oxazolones," *J. Chem Soc. Abstracts*, 3457-61 (1960).
Altmann et al., Effects of 1,2-dimethylhydrazine on the number of epithelial cells present in the villi, crypts, and mitotic pool along the rat small intestine. *Cancer Res.* 44:5522-31 (1984).
Arai et el., "Argyrophilic glial inclusions in the midbrain of patients with Parkinson's disease and diffuse Lewy body disease are immunapositive for NACP/a-synuclein," *Neuroscience Letters* 259:83-86 (1999).
Askanas et al. "Beta-Amyloid precursor epitopes in muscle fibers of inclusion body myositis" *Ann. Neurol.* 34:5.51-540 (1993).
Barner et al. "Donepezil use in Alzheimer's disease" *Ann. Pharmacotherapy* 32:70-77 (1998).
Benson et al. "Serum amyloid A protein in amyloidosis, rheumatic and enoplastic disease" *Arth. Rheum.* 22:36-42 (1979).
Castillo et al. "Perlecan binds to the beta-amyloid proteins (A beta) of Alzheimer's disease, accelerates A beta fibril formation, and maintains A beta fibril stability." *J Neurochem.* 69(6):2452-65 (1997).
Castillo et al. "Novel purification and detailed characterization of perlecan isolated from the Engelbreth-Holm-Swarm tumor for use in an animal model of fibrillar A beta amyloid persistence in brain" *J Biochem* (Tokyo) 120(2):433-44 (1996).
Castillo et al. "Laminin inhibition of beta-amyloid protein (Abeta) fibrillogenesis and identification of an Abeta binding site localized to the globular domain repeats on the laminin a chain" *J Neurosci Res.* 62(3):451-66 2 (2000).
Castillo et al. "Sulfate Content and Specific Glycosaminoglycan Backbone of Perlecan Are for Perlecan's Enhancement of Islet amyloid Polypeptide (Amylin) Fibril Formation," *Diabetes* 47:612-620 (1998).
Castillo et al. "The sulfate moieties of glycosaminoglycans are critical for the enhancement of beta-amyloid protein fibril formation." *J Neurochem.* 72(4):1681-7 (1999).
*Chemical abstracts*, vol. 50(9), May 10, 1956, col. 6402 by Tamura, Saburo et al. "VI. Syntheses of some w,w'-bis(3,4-dihydroxyphenyl)alkanes .1" Journal of the Agricultural Chemical Society of Japan (Nippon Nogei Kagakukaishi), 27: 491-498 (1953).
*Chemical abstracts*, vol. 50(9), May 10, 1956, col. 6402 by Tamura, Saburo et al. "VI. Syntheses of some w,w'-bis(3,4-dihydroxyphenyl)alkanes .2" Journal of the Agricultural Chemical Society of Japan (Nippon Nogei Kagakukaishi), 27: 877-881 (1953).
Conway et al. "Accelerated in Vitro fibril formation by a mutant a-synuclein linked to early-onset Parkinson disease," *Nature medicine* 4(11):1318-20 (1998).
Cooper et al. "Purification and, characterization of a peptide from amyloid-rich pancreases of type 2 diabetic patients," *Proc. Nati. Acad. Sci. USA* 84:8628-8632 (1987).
Crutcher et al. "Cellular and molecular pathology in Alzheimer's disease" *Hippocampus* 3:271-87 (1993).
Cutler et al. "Tacrine in Alzheimer's disease" *N. Engl. J. Med.* 328:808-810 (1993).
Derwent Abstract for Japanese Patent Application, JP 1151514, published Jun. 14, 1989, "Compsn. for treating and preventing nervous diseases—contains carboxylic acid, prf. gallic or pyrogallol-4-

(56) References Cited

OTHER PUBLICATIONS carboxylic acid, esp. useful for alzheimers disease—contains carboxylic acis, pref. gallic or pyrogallol-4-carboxylic acid, esp. useful for alzheimers disease".
Flood et al. "An amyloid B-protein fragment, AB[12-28], equipotentiy impairs post-training memory, processing when injected into different limbic system structures," *Brain Research* 663:271-276 (1994).
Flood et al. "Amnestic effects in mice of four synthetic peptides homologous to amyloid B protein from patients with Alzheimer's disease," *Proc. Natl. Acad. Sci.* 88:3363-3366 (1991).
Fraser et al. "Conformation and fibrillogenesis of Alzheimer A beta peptides with selected substitution of charged residues" *J Mol Biol.* 244(1):64-73 (1994).
Fukuchi et al. "Increased expression of beta-amyloid protein precursor and microtubule-associated protein tau during the differentiation of murine embryonal carcinoma cells" *J Neurochem.* 58(5):1863-73 (1992).
Games et al. "Alzheimer-type neuropathology in transgenic mice overexpressing V717F B-amyloid precursor protein," *Nature* 373:523-527 (1995).
Gejyo et al., "$\beta_2$-microglobulin: A new form of amyloid protein associated with chronic hemodialysis," *Kidney Int.* 30:385-390 (1986).
Gejyo et al., "A New Form of Amyloid Protein Associated with Chronic Hemodialysis was Identified as $\beta$2-microglobulin," *Biochem. Biophys. Res. Comm.* 129:701-706 (1985).
Glenner et al. "Alzheimer's Disease: Initial Report of the Purification and Characterization of a Novel Cerebrovascular Amyloid Protein," *Biochemical and Biophysical Research Communications* 120(3):885-890 (1984).
Grundke-Iqbal et al."Abnormal phosphorylation of the microtube !!!!protein tau (tau) in Alzheimer's cytoskeleton pathology" *Proc. Natl. Acad. Sci. USA* 83:4913-4917 (1986).
Haass et al. "The Swedish mutation causes early-onset Alzheimer's disease by B-secretase cleavage within the secretory pathway," *Nature Medicine* 1(12):1291-1296 (1995).
Harada et al. "Human amyloid protein: chemical variability and homogeneity" *J. Histochem. Cytochem.* 19:1-15 (1971).
Hardy "Framing β-amyloid" *Nature Genet.* 1:233-234 (1992).
Harrigan et al "Beta Amyloid is Neurotoxic in Hippocampal Slice Cultures," *Neurobiology of Aging* 16(5):779-789 (1995).
Hart et al. "Overproduction of perlecan core protein in cultured cells and transgenic mice" *J Pathol.* 194(2):262-9 (2001).
Hashimoto et al. "Human recombinant NACP/a-synuclein is aggregated and fibrillated in vitro: Relevance for Lewy body disease," *Brain Research* 799:301-306 (1998).
Hertel et al. "Inhibition of the electrostatic interaction between J-amyloid peptide and membranes prevents J-amyloid-induced toxicity", *Proc. Nat'l Acad. Sci. USA* 94(8):9412-9416 (1997).
Hsiao et al. "Correlative Memory Deficits, AB Elevation, and Amyloid Plaques in Transgenic Mice," *Science* 274:99-102 (1996).
Ishii et al., "Studies on the Chemical Constituents of Rutaceous Plants. XLIX. Development of a Versatile Method for the Synthesis of Antitumor-Active Benzo[c]phenanthridine Alkaloids. (1). Preparation of Various 2,4-Bisaryl-4-oxo-butyronitriles and 2,4-Bisaryl-4-oxobutyramides," *Chem. Pharm. Bull.* 31(9):3024-3038 (1983).
Johnson et al., "Islet Amyloid Polypeptide: Mechanisms of Amyloidogenesis in the Pancreatic Islets and Potential Roles in Diabetes Mellitus," *Lab. Invest.* 68:522-535 (1992).
Johnson et al., "Islet Amyloid, Islet-Amyloid Polypeptide, and Diabetes Mellitus," *N. Engl. J. Med.* 321:513-518 (1989).
Jucker et al. "Age-related deposition of glia-associated fibrillar material in brains of C57BL/6 mice." *Neuroscience.* 60(4):875-89 (1994).
Kamei et al. "Amyloidosis Associated with Juvenile Rheumatoid Arthritis," *Acta Path. Jpn.* 32:123-133 (1982).
Kitaguchi et al, "Novel precursor of Alzheimer's disease amyloid protein shows protease inhibitory activity," *Nature* 331:530-532 (1988).
Klunk et al. "Quantifying Amyloid B-Peptide (AB) Aggregation Using the Congo Red-AB (CR-AB) Spectrophotometric Assay" *Analytical Biochemistry* 266-76 (1999).
Kosik et al., "Microtubule-associated protein tau (r) is a major antigenic component of paired helical filaments in Alzheimer disease," *Proc. Natl. Acad. Sci. USA* 83:4044-4048 (1986).
Krüger et al. "Ala30Pro mutation in the gene encoding a-synuclein in Parkinson's disease," *Nature Genet.* 18:106-108 (1998).
Kubicova et al., "Synthesis of N,N'-Diarylalkanediamides and Their Antimycobacterial and Antialgal Activity," *Molecules* 5:714-726 (2000).
Lee et al., "A68: A Major Subunit of Paired Helical Filaments and Derivatized Forms of Normal Tau," *Science* 261:675-678 (1991).
LeVine, III et al. "Thioflavine T interaction with synthetic Alzheimer's disease B-amyloid peptides: Detection of amyloid aggregation in solution," *Protein Science* 2:404-410 (1993).
LeVine, III, H. "Thioflavine T Interaction with Amyloid β-Sheet Structures," *Amyloid: The International Journal of Experimental and Clinical Investigation* 2:1-6 (1995).
Lewy, F.H., "Paralysis agitans," in *Handbuch der Neurologie*, M. Lewandowsky (Ed.), Berlin: Springer-Verlag pp. 920-933, (1912).
Mandybur et al. "Cerebral Amyloid Angiopathy: The Vascular Pathology and Complications," *Journal of Neuropathology and Experimental Neurology* 45(1):79-90.
Maresh et al. "Detection and quantitation of perlecan mRNA levels in Alzheimer's disease and normal aged hippocampus by competitive reverse transcription-polymerase chain reaction." *J Neurochem.* 67(3):1132-44 (1996).
Masters et al. "Amyloid plaque core protein in Alzheimer disease and Down syndrome," *Proc. Natl. Acad. Sci. USA* 82:4245-4249 (1985).
Matsui et al., "Synthesis and Characterization of Fluorescent 4,6-Distributed-3-cyano-2-methylpyridines," *J. Chem. Soc. Perkin Trans. 2* pp. 201-206 (1992).
McAdam et al., "Association of Amyloidosis with Erythema Nodosum Leprosum Reactions and Recurrent Neutrophil Leucocytosis in Leprosy," *Lancet* 2:572-573 (1975).
Metaxas, P., "Familial Mediterranean fever and amyloidosis," *Kidney Int.* 20:676-685 (1981).
Miller et al. "Localization of perlecan (or a perlecan-related macromolecule) to isolated microglia in vitro and to microglia/macrophages following infusion of beta-amyloid protein into rodent hippocampus." *Glia*, 21(2):228-43 (1997).
Murray et al., "Synucleinopathies: a pathological and molecular review," *Clinical Neurosc. Res.* 1:445-455 (2001).
Murrell et al. "A Mutation in the Amyloid Precursor Protein Associated with Hereditary Alzheimer's Disease," *Science* 254:97-99 (1991).
Naiki, H. and K. Nakakuki, "First-Order Kinetic Model of Alzheimer's B-amyloid Fibril Extension In Vitro," *Laboratory Investigation* 74(2):374-383 (1996).
Nalki et al. "Kinetic Analysis of Amyloid Fibril Polymerization In vitro," *Laboratory Investigation* 65(1)1104-110 (1991).
Narhi et al. "Both Familial Parkinson's Disease Mutations Accelerate a-Synuclein Aggregation," *The Journal of Biological Chemistry* 274(14):9843-9846 (1999).
Niwano et al. "Inhibitory action of amyloid precursor protein against human Hageman factor (factor XII)", *J. Lab. Clin. Med.* 125(2):251-256 (1995).
Nochlin et al. "Familial dementia with PrP-positive amyloid plaques: a variant of Gerstmann-Straussler syndrome." *Neurology.* 39(7):910-8 (1989).
Pardridge et al., "Amyloid Angiopathy of Alzheimer's Disease: Amino Acid Composition and Partial Sequence of a 4,200-Dalton Peptide Isolated from Cortical Microvessels," *Journal of Neurochemistry* 49(5):1394-1401 (1987).
Pearl et al. "Reactions of Vanillin and its derived compounds. XXIX. 3, 3', 3, 3'—Tetrahydroxybenzil and its reduction" *J. Org. Chem.* 25:1449-1450 (1960).
Pike et al. "In vitro aging of B-amyloid protein causes peptide aggregation and neurotoxicity," *Brain Research* 563:311-314 (1991).
Pollanen et al. "Pathology and Biology of the Lewy Body," *Journal of Neuropathology and Experimental Neurology* 52(3):183-191 (1993).

(56) References Cited

OTHER PUBLICATIONS

Polymeropoulos et al. "Mutation in the a-sSynuclein Gene Identified in Families with Parkinson's Disease," *Science* 276:2045-2047 (1997).

Ponte et al "A new A4 amyloid mRNA contains a domain homologous to serine proteinase inhibitors," *Nature* 331:525-527 (1988).

Puchtler, H., Sweat, F., Levine, M., "On the binding of Congo red by amyloid," *J. Histochem. Cytochem.* 10:355-364 (1962).

Rogers et al., "Long-term efficacy and safety of donepezil in the treatment of Alzheimer's disease: an interim analysis of the results of a US multicentre open label extension study," *Eur. Neuropsych.* 8:67-75 (1998).

Saraiva et al., "Studies on plasma transthyretin (prealbumin) in familial amyloidotic polyneuropathy, Portuguese type," *J. Lab. Clin. Med.* 102:590-603 (1983).

Saraiva et al., "Amyloid Fibril Protein in Familial Amyloidotic Polyneuropathy, Portuguese Type," *J. Clin. Invest.* 74:104-119 (1984).

Sekiguchi et al. "Characterization of proteoglycans synthesized by murine embryonal cells (P19) reveals increased expression of perlecan (heparan sulfate proteoglycan) during neuronal differentiation." *J Neurosci Res.* 38(6):670-86 (1994).

Skinner et al., "The Prealbumin Nature of the Amyloid Protein in Familial Amyloid Polyneuropathy (FAP)-Swedish Variety," *Biochem. Biophys. Res. Comm.* 99:1326-1332 (1981).

Snow et al. "Time-related increase of nucleolar size and villus cell number during DMH carcinogenesis in the rat duodenal epithelium." *Cell Biol Int Rep.* 7(3):195 (1983).

Snow et al. "Differential binding of vascular cell-derived proteoglycans (perlecan, biglycan, decorin, and versican) to the beta-amyloid protein of Alzheimer's disease." *Arch Biochem Biophys.* 320(1):84-95 (1995).

Snow et al. "Proteoglycans in the pathogenesis of Alzheimer's disease and other amyloidoses." *Neurobiol. Aging* 10(5):481-97 (1989).

Snow et al. "In vitro and in vivo models to unravel the potential roles of beta/A4 in the pathogenesis of Alzheimer's disease." *Hippocampus* 3:257-67 (1993).

Snow et al. "Peripheral distribution of dermatan sulfate proteoglycans (decorin) in amyloid-containing plaques and their presence in neurofibrillary tangles of Alzheimer's disease." *J Histochem Cytochem.* 40(1):105-13 (1992).

Snow et al. "Early accumulation of heparan sulfate in neurons and in the beta-amyloid protein-containing lesions of Alzheimer's disease and Down's syndrome." *Am J Pathol.* 137(5):1253-70 (1990).

Snow et al. "A temporal and ultrastructural relationship between heparan sulfate proteoglycans and AA amyloid in experimental amyloidosis." *J Histochem Cytochem.* 39(10):1321-30 (1991).

Snow et al. "Congo red staining on 1 micron de-plasticized sections for detection of lesions in Alzheimer's disease and related disorders." *Prog Clin Biol Res.* 317:383-91 (1989).

Snow et al. "Heparin modulates the composition of the extracellular matrix domain surrounding arterial smooth muscle cells," *Am J Pathol.* 137(2):313-30 (1990).

Snow et al. "Sulfated glycosaminoglycans in Alzheimer's disease," *Hum Pathol.* 18(5):506-10 (1987).

Snow et al. "A close ultrastructural relationship between sulfated proteoglycans and AA amyloid fibrils," *Lab Invest.* 57(6):687-98 (1987).

Snow et al. "Cationic dyes reveal proteoglycans structurally integrated within the characteristic lesions of Alzheimer's disease." *Acta Neuropathol (Berl).* 78(2):113-23 (1989).

Snow et al. "Electrophoresis of glycosaminoglycans isolated from normal human plasma. Direct evidence for the presence of a heparin-like molecule." *Biomed Biochim Acta* 46(7):537-46 (1987).

Snow et al. "The presence of heparan sulfate proteoglycans in the neuritic plaques and congophillic angiopathy in Alzheimer's disease." *Am J Pathol.* 133(3):456-63 (1988).

Snow et al. "Characterization of tissue and plasma glycosaminoglycans during experimental AA amyloidosis and acute inflammation. Qualitative and quantitative analysis." *Lab Invest.* 56(6):665-75 (1987).

Snow, A.D., "Midwest summit on health care reform." *Kans Med.* 94(10):268-272 (1993).

Snow et al. "Sulfated glycosaminoglycans: a common constituent of all amyloids?" *Lab Invest.* 56(1):120-3 (1987).

Snow et al. "An important role of heparan sulfate proteoglycan (Perlecan) in a model system for the deposition and persistence of fibrillar A beta-amyloid in rat brain." *Neuron.* 12(1):219-34 (1994).

Snow et al. "Morphometric study of the rat duodenal epithelium during the initial six months of 1,2-dimethylhydrazine carcinogenesis." *Cancer Res.* 43(10):4838-49 (1983).

Snow et al. "Identification in immunolocalization of a new class of proteoglycan (keratan sulfate) to the neuritic plaques of Alzheimer's disease." *Exp Neurol.* 138(2):305-17 (1996).

Snow et al. "Heparan sulfate proteoglycan in diffuse plaques of hippocampus but not of cerebellum in Alzheimer's disease brain." *Am J Pathol.* 144(2):337-47 (1994).

Snow et al. "Sulfated glycosaminoglycans in amyloid plaques of prion diseases." *Acta Neuropathol (Berl)* 77(4):337-42 (1989).

Snow et al. "Temporal relationship between glycosaminoglycan accumulation and amyloid deposition during experimental amyloidosis. A histochemical study." *Lab Invest.* 53(1):37-44 (1985).

Snow et al. "Immunolocalization of heparan sulfate proteoglycans to the prion protein amyloid plaques of Gerstmann-Straussler syndrome, Creutzfeldt-Jakob disease and scrapie." *Lab Invest.* 63(51:601-11 (1990).

Spillantini et al., "Alpha-Synuclein in filamentous inclusions of Lewy bodies from Parkinson's disease" *Proc. Natl. Acad. Sci. USA* 95:6469-6473 (1998).

Tanzi et al "Protease inhibitor domain encoded by an amyloid protein precursor mRNA associated with Alzheimer's disease," *Nature* 331:528-632 (1988).

Tamura et al., "Studies on the inhibition of the Autoxidation of Oils and Fats, Part 6. The Syntheses of some ω, ω'-bis(3,4-dihydroxyphenyl)alkanes (1)" *Journal of the Agricultural Chemical Society of Japan (Nippon Nogei Kagakukaishi)*, 27: 491-498 (1953).

Tamura et al., "Studies on the inhibition of the Autoxidation of Oils and Fats. Part 7. Syntheses of some w,w'-bis(3,4-dihydroxyphenyl)alkanes (2)" *Journal of the Agricultural Chemical Society of Japan (Nippon Nogei Kagakukaishi)*, 27: 877-881 (1953).

Tawara et al., "Amyloid fibril protein in type I familial amyloidotic polyneuropathy in Japanese," *J. Lab. Clin. Med.* 96:811-822 (1989).

Trojanowski et al. ,"Parkinson's Disease and Related Synucleinopathies are a New Class of Nervous System Amyloidoses," *Neurotoxicology* 23:457-460 (2002).

Ueda et al., "Molecular cloning of cDNA encoding an unrecognized component of amyloid in Alzheimer's disease," *Proc. Natl. Acad. Sci.* 90:11282-11286 (1993).

Upton et al.,"Novel 5,8-Diazabenzo[c]phenanthrenes: Synthesisand Mutagenicity," *Journal of Pharmacy and Pharmacology* 50(5):475-482 (1998).

Van Broeckhoven et al.,"Amyloid β Protein Precursor Gene and Hereditary Cerebral Hemmorrhage with Amyloidosis (Dutch)," *Science* 248:1120-1122 (1990).

Van der Eycken et al. , "The Synthesis of 4-Desoxy-2-Azapodophyl-lotoxins," *Tet. Lett* 30(29):3873-3876 (1989).

*Vogel's Textbook of Practical Organic Chemistry*, 5th ed. Furniss, B.S. et al. (Eds.), London : Longman Scientific & Technical ; New York : John Wiley & Sons, 6.142; 1044-1045 (1989).

Wakabayashi et al., "Accumulation of α-synuclein/NACP is a cytopathological feature common to Lewy body disease and multiple system atrophy," *Acta Neuropath* 96:445-452 (1998).

Wattanasin et al., "An improved Procedure for the Preparation of Chalcones and Related Enones," *Synthesis* 1980(8): 647-650 (1980).

WHO-IUIS Nomenclature Sub-Committee, "Nomenclature of amyloid and amyloidosis," *Bulletin of the World Health Organization*, 71(1): 106-108 (1993).

Williard et al., "Boron Trihalide-Methyl Sulfide Complexes as Convenient Reagents for Dealkylation of Aryl Ethers," *Tetrahedron Letters* 21:3731-3734 (1980).

(56) References Cited

OTHER PUBLICATIONS

Wood et al. "α-Synuclein Fibrillogenesis Is Nucleation-dependent," *The Journal of Biological Chemistry* 274(28):19509-19512 (1999).
Baunumann et al, "A simple isolation method for the major catechins in green tea using high-speed countercurrent chromatography," *J. Natural Prod.* 64:353-355, (2001).
Castillo and Templeton, "Subunit structure of bovine ESF (extracellular-matrix stabilizing factor(s)) A chondroitin sulfate proteoglycan with homology to human Iαi (inter-α-trypsin inhibitors,", FEBS, 318(3): 292-296 (1993).
Czochanaka et al, "Direct Proof of a Homogeneous Polyflavan-3-ol Structure for Polymeric Proanthocyanidins," *J.C. S. Chem. Comm.* pp. 375-377, (1979).
Hashimoto et al, "Tannins and related Compounds. XC. 8-C-Ascorbyl(−)-Epigallocatechin 3-)-Gallate and novel dimeric Flaven-3-ols, Oolonghomobisflavans A and B from Oolong tea.", *Chem Pharm. Bull.* 37(12) 3255-3263 (1989).
Ho et al. "Phytochemicals in Teas and Rosemary and Their Cancer-Preventive Properties," *ACS Symp. Ser.* (*Food Phytochemicals for Cancer Prevention II*) vol. 547, pp. 2-19 1994.
Ishimaru et al, "Flavan-2-ol and Procyanidin Glycosides from *Quercus Miyagii*," *Phytochemistry* 26:1167-1170, (1987).
Jain et al. "Antiinflammatory Effects of an Ayurvedic Preparation, Brahmi Rasayan, in Rodents," *Indian Journal of Experimental Biology*, 32:633-636 (1994).
Kashiwada et al, "Tannins and Related Compounds. XCIII. Occurnce of Enantiomeric Proanthocyanidins in the Leguminosae Plants, *Cassia fistula* L and *C.javanica* L.," *Chem. Pharm. Bull.* 38:888-893 (1990).
Morimoto et al, "Tannins and Related Compounds. LXI. Isolation and Structure of Novel Bi- and Triflavanoids from the leaves of *Cassia fistula* L.," *Chem. Pharma. Bull.* 36:39-47, (1988).
Patent Abstracts of Japan citing Japanese Patent 10-175852 published Jun. 30, 1998, "Water (of Chinese Medicine Idea) Improver and Composition for Oral Administration Containing the Same".
Patent Abstracts of Japan citing Japanese Patent 10-175854 published Jun. 30, 1998, External Preparation for Skin Improving Water (of Chunese Medicine Area).
Patent Abstracts of Japan citing Japanese Patent 2001-341424 published Dec. 11, 2001, "Sensitizer for Urea Urethane Compound Developer".
Porter, J.J, "Flavans and proanthocyanidins," Chapter 2 *The Flavanoids—Advances in Research since 1980*, J B Harborne (Ed.), London: Chapman and Hall, pp. 21-62, 1988.
Sang et al, "Iridoid Glycosides from the leaves of *Morinda citrifolia*,": *J. Nat. Prod.* 64:799-800 (2001).
Santos-Buelga, C. and A. Scalbert, "Proanthocyanidins and tannin-like compounds—nature, occurrence, dietry intake and effects on nutrition and health," *J. Sci. Food Agri.* 80: 1094-1117, (2000).
Steinberg. "Uncaria Tomentosa (cat's Claw) a wondrous herb from the peruvian rain forest" *Townsend Letter for Doctors*—pp. 442-443, May 1994.
Tamaoka et al "Biochemical evidence for the long tail form of amyloid B protein as a seed molecule in cerebral deposits of alzheimer's disease." *Biochemical and biophysical research communications*, 205(1): 834-842, (1994).
Thompson et al, "Plant Proanthocyanidins. Part 1. Introduction; the Isolation, Structure, and Distribution in Nature of Plant Procyanidins," *J. Chem. Soc. Perkins Trans.* 1: 1387-1399 (1972).
Tückmantel, "Studies in Polyphenol Chemistry and Bioactivity. 1. Preparation of Building Blocks from (+)-Catechin. Procyanidin Formation. Synthesis of the Cancer Cell Growth Inhibitor, 3-*O*-Galloyl-(2R,3R)-epicatechin-4β,8-[3-*O*-Galloyl-(2R,3R)-epicatechin]," *J. Am. Chem. Soc.* 121:12073-12081 (1999).
Zhang et al, "Potentillanin, a Biflavanoid and a procyanidin glycoside from potentilla viscosa," *Phytochemistry* 27:3277-3280, (1988).
Lee et al., "Two New Constituents of Isodon excises and Their Evaluation in an Apoptosis Inhibition Assay," *J. Nat. Prod.* 64:659-660 (2001).
Kim et al., "Total Synthesis of Calebin-A, Preparation of Its Analogues, and Their Neuronal Cell Protectivity Against b-Amyloid Insult," Bioog, Med. Chem. Lett. 11:2541-2543 (2001).
Database CAPLUS on STN, Acc, No. 1977:83512, Gazave et al., Conv. Int. Polifenoli, [Relaz. Comm.] (1975), p. 135-41 (abstract).
Database CAPLUS on STN, Acc. No. 1987:417476, Yun-Choi et al., Yakhak Hoechi (1986), 30(5), p. 245-252 (abstract).

\* cited by examiner

COMPOUNDS, COMPOSITIONS AND METHODS FOR THE TREATMENT OF INFLAMMATORY DISEASES

This application is a Continuation-in-Part of U.S. application Ser. No. 12/475,097 filed May 29, 2009 which is a Continuation-in-Part of U.S. application Ser. No. 10/077,596 filed Feb. 15, 2002, which is a Continuation-in-Part of application Ser. No. 10/053,625 filed Nov. 2, 2001, now issued as U.S. Pat. No. 6,929,808 on Aug. 16, 2005.

This application is also a Continuation of U.S. application Ser. No. 13/188,636 filed Jul. 22, 2011, and a Continuation-in-Part of U.S. application Ser. No. 12/837,721 filed Jul. 16, 2010 which claims the benefit of priority under 35 U.S.C. §120 to, and is a Continuation of U.S. application Ser. No. 12/269,017, now abandoned, filed Nov. 11, 2008 which is a Continuation of U.S. application Ser. No. 10/452,851, filed May 30, 2003, now U.S. Pat. No. 7,514,583, which claimed priority under 35 USC 119(e) to:

(1) U.S. Provisional Application No. 60/385,144, filed May 31, 2002,
(2) U.S. Provisional Application No. 60/409,100, filed Sep. 9, 2002,
(3) U.S. Provisional Application No. 60/412,272, filed Sep. 20, 2002,
(4) U.S. Provisional Application No. 60/435,880, filed Dec. 20, 2002, and
(5) U.S. Provisional Application No. 60/463,104, filed Apr. 14, 2003.

The entire contents of all of these applications are incorporated by reference into this application.

TECHNICAL FIELD

This invention relates to bis- and tris-dihydroxyaryl compounds and their methylenedioxy analogs and pharmaceutically acceptable esters, their synthesis, pharmaceutical compositions containing them, and their use in the treatment of inflammation that results from diseases such as arthritis, and in the manufacture of medicaments for such treatment.

BACKGROUND OF THE INVENTION

Various forms of inflammation are characterized by activation of macrophages. Macrophages are thought to induce and maintain inflammatory processes mainly by producing various products that, by acting on other cells, bring about the deleterious consequences of inflammation such as the generation of nitric oxide. For example, macrophages produce cytokines. These proteins are central mediators in inflammatory processes, such as the local inflammatory processes characteristic of arthritis or colitis. Cytokines produced by macrophages are also thought to be involved in systemic inflammatory processes, such as endotoxic shock. Macrophage products are more generally involved in pathophysiological mechanisms, such as plasma extravasation, inflammatory cell diapedesis, release of toxic free radicals such as nitric oxide, endothelial injury, and release of tissue degrading enzymes, which result in tissue injury and, ultimately, organ failure.

Tumor necrosis factor alpha (TNF-$\alpha$) is a cytokine associated with macrophage activation. TNF-$\alpha$ is also thought to be involved in inducing most of the pathophysiological events characteristic of inflammation. TNF-$\alpha$ plays an important role in regulating inflammation, cellular immune response, and host defense. TNF-$\alpha$ is a key cytokine associated with the toxic effect of lipopolysaccharide (LPS) endotoxin and in the pathogenesis of septic shock, as evidenced by high serum plasma levels of TNF-$\alpha$ after LPS administration to animals or to human volunteers, or in septic subjects. Administration of anti-TNF-$\alpha$ antibodies protects against the lethal effects of LPS and of live bacteria in a variety of animal models. Moreover, TNF-$\alpha$ can be a central target in the treatment of rheumatoid arthritis. Conversely in diseases such as rheumatoid arthritis, osteoarthritis, psoriasis, Crohn's disease, inflammatory bowel disease and other chronic disorders of the immune system, excessive levels of TNF-$\alpha$ play a role in the pathophysiology. Indeed, blocking TNF-$\alpha$ can halt disease progression and has led to the search for inhibitors of TNF-$\alpha$.

Interleukin-12 (IL-12) is another macrophage product that has been shown to be involved in the induction of pathology in several inflammatory diseases. These diseases include autoimmune diseases such as multiple sclerosis, inflammatory bowel disease, insulin dependent diabetes mellitus, and rheumatoid arthritis, and inflammatory states such as septic shock and the generalized Schwarzman reaction.

Rheumatoid arthritis is a common rheumatic disease, affecting more than two million people in the United States alone. The disease is three times more prevalent in women as in men but afflicts all races equally. The disease can begin at any age, but most often starts between the ages of forty and sixty. In some families, multiple members can be affected, suggesting a genetic basis for the disorder. The cause of rheumatoid arthritis is unknown. It is suspected that certain infections or factors in the environment might trigger the immune system to attack the body's own tissues, resulting in inflammation in various organs of the body. Regardless of the exact trigger, the result is an immune system that is geared up to promote inflammation in the joints and occasionally other tissues of the body, Lymphocytes are activated and cytokines, such as TNF-$\alpha$ and interleukin-1 (IL-1) are expressed in the inflamed areas.

The clinical expression of rheumatoid arthritis is manifested by chronic inflammation of the joints, the tissue surrounding the joints such as the tendons, ligaments, and muscles, as well as other organs in the body such as the eyes. The inflammation process of causes swelling, pain stiffness, and redness in the joints. In some patients with rheumatoid arthritis, chronic inflammation leads to the destruction of the cartilage, bone and ligaments causing deformity of the joints. Rheumatic diseases can involve other, seemingly unrelated organs as well, such as eyes, skin and glands. Rheumatic diseases are usually divided into those that primarily involve joints, known as arthritis, and those involving other tissues, generally referred to connective tissue diseases. Arthritis is further subdivided into inflammatory and non-inflammatory arthritis. The more common types of inflammatory arthritis are rheumatoid arthritis, gout, psoriatic arthritis (associated with the skin condition psoriasis), reactive arthritis, viral or post-viral arthritis (occurring after an infection), and spondylarthritis which affects the spine as well as joints.

SUMMARY OF THE INVENTION

In a first aspect, this invention is the use of the compounds described herein in methods of inhibiting the inflammatory process, the method comprising administering to a mammal suffering from inflammation a therapeutically effective amount of a pharmaceutical composition comprising the compounds and particularly when wherein the inflammatory process results from a disease selected from the group consisting of ulcerative colitis, endotoxic shock, rheumatoid arthritis, juvenile arthritis, osteoarthritis, psoriasis, Crohn's disease, inflammatory bowel disease, multiple sclerosis, insulin dependent diabetes mellitus, gout, psoriatic arthritis, reactive arthritis, viral or post-viral arthritis and ankylosing spondylarthritis.

In another aspect, this invention is bis- and tris-dihydroxyaryl compounds and their methylenedioxy analogs and pharmaceutically acceptable esters, and pharmaceutically acceptable salts thereof.

The compounds are:
(1) compounds of the formula:

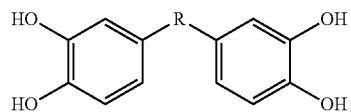

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group; and
(2) the compounds that are:
3,4,3',4'-tetrahydroxybenzoin (compound 1); 3,4,3',4'-tetrahydroxydesoxybenzoin (compound 2); 3,4,3',4'-tetrahydroxydiphenylmethane (compound 3); 1,2-bis(3,4-dihydroxyphenyl)ethane (compound 4); 1,3-bis(3,4-dihydroxyphenyl)propane (compound 5); 3,4,3',4'-tetrahydroxychalcone (compound 6); 3,5-bis(3,4-dihydroxyphenyl)-1-methyl-2-pyrazoline (compound 7); 4,6-bis(3,4-dihydroxyphenyl)-3-cyano-2-methylpyridine (compound 8); 1,4-bis(3,4-dihydroxybenzyl)piperazine (compound 9); N,N'-bis(3,4-dihydroxybenzyl)-N,N'-dimethylethylenediamine (compound 10); 2,5-bis(3,4-dihydroxybenzyl)-2,5-diaza[2.2.1]bicycloheptane (compound 11); N,N'-bis(3,4-dihydroxybenzyl)-trans-1,2-diaminocyclohexane (compound 12); N,N'-bis(3,4-dihydroxybenzyl)-trans-1,4-diaminocyclohexane (compound 13); N,N'-bis(3,4-dihydroxybenzyl)-cis-1,3-bis(aminomethyl)cyclohexane (compound 14); N-(3,4-dihydroxybenzyl)proline 3,4-dihydroxybenzylamide (compound 15); 2-(3,4-dihydroxybenzyl)isoquinoline-3-carboxylic acid 3,4-dihydroxyphenethylamide (compound 16); 2,6-bis(3,4-dihydroxybenzyl)cyclohexanone (compound 17); 3,5-bis(3,4-dihydroxybenzyl)-1-methyl-4-piperidinone (compound 18); 2,4-bis(3,4-dihydroxybenzyl)-3-tropinone (compound 19); tris-(3,4-dihydroxybenzyl)methane (compound 20); α-(3,4-dihydroxybenzamido)-3,4-dihydroxycinnamic acid 3,4-dihydroxybenzyl amide (compound 21); 4-(3,4-dihydroxybenzylaminomethylene)-2-(3,4-dihydroxyphenyl)oxazolin-5-one (compound 22); 1,4-bis(3,4-dihydroxybenzoyl)piperazine (compound 23); N,N'-bis(3,4-dihydroxybenzoyl)-N,N'-dimethylethylenediamine (compound 24); 2,5-bis(3,4-dihydroxybenzoyl)-2,5-diaza[2.2.1]bicycloheptane (compound 25); N,N'-bis(3,4-dihydroxybenzoyl)-trans-1,2-diaminocyclohexane (compound 26); N,N'-bis(3,4-dihydroxybenzoyl)-cis-1,3-bis(aminomethyl)cyclohexane (compound 27); 3,6-bis(3,4-dihydroxybenzyl)-2,5-diketopiperazine (compound 28); 3,6-bis(3,4-dihydroxybenzylidene)-1,4-dimethyl-2,5-diketopiperazine (compound 29); N-(3,4-dihydroxyphenylacetyl)proline 3,4-dihydroxyanilide (compound 30); 2,3-bis(3,4-dihydroxyphenyl)butane (compound 31); 1,3-bis(3,4-dihydroxybenzyl)benzene (compound 32); 1,4-bis(3,4-dihydroxybenzyl)benzene (compound 33); 2,6-bis(3,4-dihydroxybenzyl)pyridine (compound 34); 2,5-bis(3,4-dihydroxybenzyl)thiophene (compound 35); 2,3-bis(3,4-dihydroxybenzyl)thiophene (compound 36); 1,2-bis(3,4-dihydroxyphenyl)cyclohexane (compound 37); 1,4-bis(3,4-dihydroxyphenyl)cyclohexane (compound 38); 3,7-bis(3,4-dihydroxyphenyl)bicyclo[3.3.0]octane (compound 39); 2,3-bis(3,4-dihydroxyphenyl)-1,7,7-trimethylbicyclo[2.2.1]heptane (compound 40); 1,2-bis(3,4-dihydroxyphenoxy)ethane (compound 41); 1,3-bis(3,4-dihydroxyphenoxy)propane (compound 42); trans-1,2-bis(3,4-dihydroxyphenoxy)-cyclopentane (compound 43); N-(3,4-dihydroxybenzyl)-3-(3,4-dihydroxyphenoxy)-2-hydroxypropylamine (compound 44); 3,4-dihydroxyphenoxyacetic acid 3,4-dihydroxyanilide (compound 45); 3,4-dihydroxyphenoxyacetic acid 3,4-dihydroxybenzylamide (compound 46); 3,4-dihydroxyphenoxyacetic acid 3,4-dihydroxyphenethylamide (compound 47); 3,4-dihydroxybenzoic acid p-(3,4-dihydroxyphenoxy)anilide (compound 48); 3,4-dihydroxybenzoic acid o-(3,4-dihydroxyphenoxy)anilide (compound 49); 2,6-bis(3,4-dihydroxyphenoxy)pyridine (compound 50), 3,4-dihydroxybenzoic acid 3,4-dihydroxyanilide (compound 51); 3,4-dihydroxybenzoic acid 3,4-dihydroxybenzylamide (compound 52); 3,4-dihydroxybenzoic acid 3,4-dihydroxyphenethylamide (compound 53); 3,4-dihydroxyphenylacetic acid 3,4-dihydroxyanilide (compound 54); 3,4-dihydroxyphenylacetic acid 3,4-dihydroxybenzylamide (compound 55); 3,4-dihydroxyphenylacetic acid 3,4-dihydroxyphenethylamide (compound 56); 3-(3,4-dihydroxyphenyl)propionic acid 3,4-dihydroxyanilide (compound 57); 3-(3,4-dihydroxyphenyl)propionic acid 3,4-dihydroxybenzylamide (compound 58); 3-(3,4-dihydroxyphenyl)propionic acid 3,4-dihydroxyphenethylamide (compound 59); 3,4-dihydroxycinnamic acid 3,4-dihydroxyanilide (compound 60); 3,4-dihydroxycinnamic acid 3,4-dihydroxybenzylamide (compound 61); 3,4-dihydroxycinnamic acid 3,4-dihydroxyphenethylamide (compound 62); oxalic acid bis(3,4-dihydroxyanilide) (compound 63); oxalic acid bis(3,4-dihydroxybenzylamide) (compound 64); oxalic acid bis(3,4-dihydroxy-phenethylamide) (compound 65); succinic acid bis(3,4-dihydroxyanilide) (compound 66); succinic acid bis(3,4-dihydroxybenzylamide) (compound 67); succinic acid bis(3,4-dihydroxyphenethylamide) (compound 68); maleic acid bis(3,4-dihydroxyanilide) (compound 69); maleic acid bis(3,4-dihydroxybenzylamide) (compound 70); fumaric acid bis(3,4-dihydroxyanilide) (compound 71); fumaric acid bis(3,4-dihydroxybenzylamide) (compound 72); bis(3,4-dihydroxybenzyl)amine (compound 73); N-(3,4-dihydroxybenzyl)-3,4-dihydroxyphenethylamine (compound 74); tris(3,4-dihydroxybenzyl)amine (compound 75); 1,3-bis(3,4-dihydroxyphenyl)urea (compound 76); 1-(3,4-dihydroxyphenyl)-3-(3,4-dihydroxybenzyl)urea (compound 77); 1-(3,4-dihydroxyphenyl)-3-(3,4-dihydroxyphenethyl)urea (compound 78); 3-deoxy-3-(3,4-dihydroxybenzyl)aminoepicatechin (compound 79); 3-deoxy-3-(3,4-dihydroxyphenethyl)aminoepicatechin (compound 80); 2,3,6,7-tetrahydroxy-9,10-epoxy-9,10-dihydroacridine (compound 81); 10-aminoanthracene-1,2,7,8-tetraol (compound 82); acridine-1,2,6,7-tetraol (compound 83); phenoxazine-2,3,7,8,10-pentaol (compound 84); dibenzo[c,f][2,7]napthyridine-2,3,10,11-tetraol (compound 85); and 6-methyl-5,6,6a,7-tetrahydro-4H-dibenzo[de,g]quinoline-2,10,11-triol (compound 86);
(3) the methylenedioxy analogs and pharmaceutically acceptable esters of compounds of (1) and (2); and (4) the pharmaceutically acceptable salts of the compounds of (1) to (3).

In another aspect, this invention is pharmaceutical compositions comprising a compound of the first aspect of this invention and a pharmaceutically acceptable excipient; and pharmaceutical compositions comprising a pharmaceutically acceptable excipient and, as the sole active ingredient, a compound of the first aspect of the invention.

In another aspect, this invention is a method of treating inflammatory diseases such as arthritis in mammals, especially humans, by administration of a therapeutically effective amount of a compound of the first aspect of this invention, for example as a pharmaceutical composition.

In another aspect, this invention is the use of a compound of the first aspect of this invention in the manufacture of a medicament for the treatment of inflammatory diseases such as arthritis and use of a compound for inhibition of the inflammatory cascade.

In another aspect, this invention is a method of treatment of inflammatory diseases such as arthritis and includes the step of administering a therapeutically effective amount of a compound of this invention. Preferably the compound is selected from the groups described below with respect to their inhibitory activity of microglial nitric oxide (NO) production and/or TNF-α release.

The various compounds disclosed herein inhibit lipopolysaccharide(LPS)/interferon gamma (IFNγ) induced NO release by microglia. This release by the microglia is in response to LPS/IFNγ pro-inflammatory stimulation. These compounds may prevent oxidative stress induced cell death in addition to the inhibition of NO and TNF-α release by microglia and subsequent inhibition of the inflammatory cascade.

DETAILED DESCRIPTION OF THE INVENTION

Definitions

In this application, the following terms shall have the following meanings, without regard to whether the terms are used variantly elsewhere in the literature or otherwise in the known art.

The compounds of the invention, i.e. the compounds of the formula shown in the paragraph numbered (1) at the top of page 1 of the application and the compounds on the list immediately following and numbered (2) (compounds #1 to #86), are referred to generally as bis- and tris-dihydroxyaryl compounds, or sometimes just as "dihydroxyaryl compounds" and sometimes just "compounds". It will be noted that compound #84 has an additional hydroxy group, but does have two dihydroxyaryl groups; while compound #86 has only one dihydroxyaryl group but has an additional phenolic hydroxyl moiety.

"Methylenedioxy analogs" refers to the compounds of this invention in which each of the pairs of adjacent hydroxyl moieties of the dihydroxyaryl groups have been replaced by methylenedioxy groups. The methylenedioxy compounds are illustrated and referred to as compounds #1B to #86B. The methylenedioxy groups also are convenient intermediate protecting groups for the dihydroxy moieties and therefore these disclosed compounds are believed to also serve as effective prodrugs. The methylenedioxy analogs #1B to #80B are illustrated in Example 3.

"Pharmaceutically acceptable esters" refers to the compounds of this invention where the hydroxyl moieties of the dihydroxyaryl groups of the compounds are esterified with an acid or acids that result in a pharmaceutically acceptable poly(ester). The compounds are shown in Example 4 as acetylated, and these acetylated compounds are illustrated and referred to as compounds #1C to #86C; but it should be understood that the depiction of acetyl esters in Example 4 is merely illustrative, and all pharmaceutically acceptable esters are included within this invention. The ester groups are expected to serve as intermediate protecting groups for the hydroxyl moieties and therefore the pharmaceutically acceptable esters are expected to serve as effective prodrugs for their underlying bis- and tris-dihydroxyaryl compounds.

Chemical structures for each of the compounds of this invention (with the note that the acetates are shown as representative of the pharmaceutically acceptable esters as a class) are shown. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.qmul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants (for example, by the use of "3,4-dihydroxybenzoic acid 3,4-dihydroxyanilide" instead of "N-(3,4-dihydroxyphenyl)-3,4-dihydroxybenzamide"). However, the names used are explicitly equated to chemical structures, and are believed to be readily understood by a person of ordinary skill in the art.

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salt" means a salt that is pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid mono-salt or a di-salt; and similarly where there are more than two acidic groups present, some or all of such groups can be salified.

A "therapeutically effective amount" in general means the amount that, when administered to a subject or animal for treating a disease, is sufficient to affect the desired degree of treatment for the disease. A "therapeutically effective amount" or a "therapeutically effective dosage" preferably inhibits, reduces, disrupts, NO or TNF-α release, or treats a disease associated with these conditions, such as an inflammatory disease, by at least 20%, more preferably by at least 40%, even more preferably by at least 60%, and still more preferably by at least 80%, relative to an untreated subject. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day. A broad range of disclosed composition dosages are believed to be both safe and effective.

"Treating" or "treatment" of a disease includes preventing the disease from occurring in a mammal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease), such as by disruption of the inflammatory cascade. One such preventive treatment may be use of the disclosed compounds for the treatment of inflammatory diseases.

"A pharmaceutical agent" or "pharmacological agent" or "pharmaceutical composition" refers to a compound or combination of compounds used for treatment, preferably in a pure or near pure form. In the specification, pharmaceutical or pharmacological agents include the compounds of this invention. The compounds are desirably purified to 80% homogeneity, and preferably to 90% homogeneity. Compounds and compositions purified to 99.9% homogeneity are believed to be advantageous. As a test or confirmation, a suitable homogeneous compound on HPLC would yield, what those skilled in the art would identify as a single sharp-peak band.

Compounds of the Invention

The compounds of this invention are:
(1) compounds of the formula:

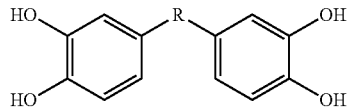

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group; and
(2) the compounds that are:
3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethylethylenediamine; 2,5-bis(3,4-dihydroxybenzyl)-2,5-diaza[2.2.1]bicycloheptane; N,N'-bis(3,4-dihydroxybenzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; 2-(3,4-dihydroxybenzyl)isoquinoline-3-carboxylic acid 3,4-dihydroxyphenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxyphenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxybenzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxybenzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzylamide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl)propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzylamide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxybenzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxyphenethyl)urea; 3-deoxy-3-(3,4-dihydroxybenzyl)aminoepicatechin; 3-deoxy-3-(3,4-dihydroxyphenethyl)aminoepicatechin; 2,3,6,7-tetrahydroxy-9,10-epoxy-9,10-dihydroacridine; 10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol;

(3) the methylenedioxy analogs and pharmaceutically acceptable esters of the compounds of (1) and (2); and (4) the pharmaceutically acceptable salts of the compounds of (1) to (3).

Within the compounds of this invention, a first group of compounds is the compounds selected from the group consisting of:

(1) compounds of the formula:

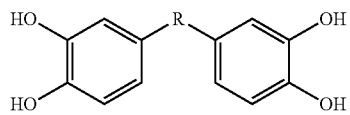

where:

R is a $C_1$-$C_{10}$, especially a $C_{1-6}$, alkylene group, in which, when the number of carbon atoms is at least 2, there are optionally 1 or 2 non-adjacent double bonds; 1 to 3 non-adjacent methylene groups are optionally replaced by NR' (where R' is H, $C_{1-3}$ alkyl, or $C_{2-4}$ acyl), O, or S, especially NH or N—$CH_3$; and 1 or 2 methylene groups are optionally replaced by a carbonyl or hydroxymethylene group;

(2) the methylenedioxy analogs and pharmaceutically acceptable tetraesters thereof; and (3) the pharmaceutically acceptable salts of the compounds of (1) and (2).

Within this first group, a subgroup of compounds is the group of compounds selected from the group consisting of:

(1) compounds of the formula:

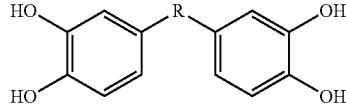

where:

R is a $C_2$-$C_{10}$, especially a $C_{2-6}$, alkylene group in which there is optionally 1 double bond; and 1 or 2 non-adjacent ethylene groups are replaced by —C(O)NR'— or —NR'C(O)— (where R' is H or lower alkyl);

(2) the methylenedioxy analogs and pharmaceutically acceptable tetraesters thereof; and (3) the pharmaceutically acceptable salts of compounds of (1) and (2).

Within the compounds of this invention, a second group of compounds is:

(1) the compounds that are:
3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethylethylenediamine; 2,5-bis(3,4-dihydroxybenzyl)-2,5-diaza[2.2.1]bicycloheptane; N,N'-bis(3,4-dihydroxybenzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; dihydroxybenzyl isoquinoline-3-carboxylic acid 3,4-dihydroxyphenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxyphenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxybenzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxybenzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzylamide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl)propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzylamide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxybenzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxyphenethyl)urea; 3-deoxy-3-(3,4-dihydroxybenzyl)aminoepicatechin; 3-deoxy-3-(3,4-dihydroxyphenethyl)aminoepicatechin; 2,3,6,7-tetrahydroxy-9,10-epoxy-9,10-dihydroacridine;

10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol;

(2) the methylenedioxy analogs and pharmaceutically acceptable esters thereof; and (3) the pharmaceutically acceptable salts of the compounds of (1) and (2).

Within this second group, a subgroup of compounds is:

(1) the compounds that are:
3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethylethylenediamine; 2,5-bis(3,4-dihydroxybenzyl)-2,5-diaza[2.2.1]bicycloheptane; N,N'-bis(3,4-dihydroxybenzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; 2-(3,4-dihydroxybenzyl)isoquinoline-3-carboxylic acid 3,4-dihydroxyphenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxyphenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxybenzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxybenzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzylamide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl)propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzylamide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxybenzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxyphenethyl)urea; 3-deoxy-3-(3,4-dihydroxybenzyl)aminoepicatechin; and 3-deoxy-3-(3,4-dihydroxyphenethyl)aminoepicatechin;

(2) the methylenedioxy analogs and pharmaceutically acceptable esters thereof; and (3) the pharmaceutically acceptable salts of the compounds of (1) and (2).

Within this subgroup, a further subgroup is:

(1) the compounds that are:
3,4,3',4'-tetrahydroxybenzoin; 3,4,3',4'-tetrahydroxydiphenylmethane; 1,2-bis(3,4-dihydroxyphenyl)ethane; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-trans-1,2-diaminocyclohexane; 2,4-bis(3,4-dihydroxybenzyl)-3-tropinone; α-(3,4-dihydroxybenzamido)-3,4-dihydroxycinnamic acid 3,4-dihydroxybenzyl amide; 1,4-bis(3,4-dihydroxybenzoyl)piperazine; N,N'-bis(3,4-dihydroxybenzoyl)-trans-1,2-diaminocyclohexane; 3,4-dihydroxybenzoic acid 3,4-dihydroxyanilide; 3,4-dihydroxybenzoic acid 3,4-dihydroxybenzylamide; 3-(3,4-dihydroxyphenyl)propionic acid 3,4-dihydroxyanilide; 3-(3,4-dihydroxyphenyl)propionic acid 3,4-dihydroxybenzylamide; 3,4-dihydroxycinnamic acid 3,4-dihydroxybenzylamide; oxalic acid bis(3,4-dihydroxyanilide); succinic acid bis(3,4-dihydroxyanilide); succinic acid bis(3,4-dihydroxybenzylamide); bis(3,4-dihydroxybenzyl)amine; tris(3,4-dihydroxybenzyl)amine; 1,3-bis(3,4-dihydroxyphenyl)urea; and 1-(3,4-dihydroxyphenyl)-3-(3,4-dihydroxyphenethyl)urea;

(2) the methylenedioxy analogs and pharmaceutically acceptable esters thereof; and (3) the pharmaceutically acceptable salts of the compounds of (1) and (2).

Within each of these groups and subgroups, there are especially the compounds of the invention that are the bis- and tris(dihydroxyaryl) compounds (i.e. the compounds of the formula or of the list) and compound #86, and their pharmaceutically acceptable salts.

Synthesis of the Compounds of the Invention

The compounds of this invention may be prepared by methods generally known to the person of ordinary skill in the art, having regard to that knowledge and the disclosure of this application.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. A preferred protective group is the methylenedioxy group, as seen in many of Examples 1-23, and a wide variety of methylenedioxyphenyl compounds (such as 3,4-methylenedioxyacetophenone, 3,4-methylenedioxyaniline, 3,4-methylenedioxybenzaldehyde, 3,4-methylenedioxybenzoic acid, 3,4-methylenedioxybenzonitrile, 3,4-methylenedioxybenzoic acid, 3,4-methylenedioxybenzoyl chloride, 3,4-methylenedioxycinnamic acid, 3,4-methylenedioxynitrobenzene, 3,4-methylenedioxyphenol, 3,4-methylenedioxyphenylacetic acid, 3,4-methylenedioxyphenylacetonitrile, 3,4-methylenedioxyphenyl isocyanate, 3,4-methylenedioxyphenylmagnesium bromide, and 3,4-methylenedioxyphenylmethanol) are commercially available. Other protecting groups, such as the benzyl and methoxymethyl groups, may also be used.

Other starting materials or early intermediates may be prepared by elaboration of the materials listed above, for example, by methods well known to a person of ordinary skill in the art.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Pharmacology and Utility

The compounds of this invention, either as the dihydroxyaryl compounds per se, or as the methylenedioxy analogs or pharmaceutically acceptable esters (once de-protected either in the body or in vitro), act to inhibit or prevent microglial NO and/or TNF-α. Their activity can be measured in vitro by methods such as those discussed herein.

Compounds of special interest for treating inflammatory diseases such as arthritis are selected from the group consisting of (1) the compounds that are:
3,4,3',4'-tetrahydroxybenzoin; 3,4,3',4'-tetrahydroxydiphenylmethane; 1,2-bis(3,4-dihydroxyphenyl)ethane; N,N'-bis(3,4-dihydroxybenzyl)-trans-1,2-diaminocyclohexane; α-(3,4-dihydroxybenzamido)-3,4-dihydroxycinnamic acid 3,4-dihydroxybenzylamide; 3,4-dihydroxybenzoic acid 3,4-dihydroxyanilide; bis(3,4-dihydroxybenzyl) amine; 1,3-bis(3,4-dihydroxyphenyl)urea; and 1-(3,4-dihydroxyphenyl)-3-(3,4-dihydroxyphenethyl)urea;
(2) the methylenedioxy analogs and pharmaceutically acceptable esters thereof; and
(3) the pharmaceutically acceptable salts of the compounds of (1) and (2).

Especially of interest are the compounds of (1) above and their pharmaceutically acceptable salts.

Pharmaceutical Compositions and Administration

In general, compounds of the invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease, its severity, the age and relative health of the animal being treated, the potency of the compound(s), and other factors. As anti-inflammatory agents, therapeutically effective amounts of compounds of this invention may range from 0.1-1000 mg/Kg body weight/day, such as from 1-100 mg/Kg/day; for example, 10-100 mg/Kg/day. A person of ordinary skill in the art will be conventionally able, and without undue experimentation, having regard to that skill and to this disclosure, to determine a therapeutically effective amount of a compound for the treatment of inflammatory diseases such as arthritis.

Preferred compositions will contain a compound of this invention that is at least substantially pure. In general "pure" means better than 95% pure, and "substantially pure" means a compound synthesized such that the compound, as made as available for consideration into a therapeutic dosage, has only those impurities that can not readily nor reasonably be removed by conventional purification processes.

In general, the compounds of this invention will be administered as pharmaceutical compositions by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as *Remington: The Science and Practice of Pharmacy*, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols.

In particular, the compound(s)—optimally only one such compound is administered in any particular dosage form—can be administered, orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n propyl p hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

The compounds of the invention can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

It is especially advantageous to formulate the compounds in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labelled or accompanied by a label indicating the intended method of treatment, such as the treatment of an inflammatory disease such as arthritis.

Sustained Release Formulations

The invention also includes the use of sustained release formulations to deliver the compounds of the present invention to the desired target (i.e. systemic organs) at high circulating levels (between $10^{-9}$ and $10^{-4}$ M) are also disclosed.

It is understood that the compound levels are maintained over a certain period of time as is desired and can be easily determined by one skilled in the art using this disclosure and compounds of the invention. In a preferred embodiment, the invention includes a unique feature of administration comprising a sustained release formulation so that a constant level of therapeutic compound is maintained between $10^8$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein may be readily selected for use with the pharmaceutical compositions of the invention. Thus, single unit dosage forms suitable for oral administration, such as, but not limited to, tablets, capsules, gelcaps, caplets, powders and the like, that are adapted for sustained release are encompassed by the present invention.

In a preferred embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are encompassed by this invention. The sustained release formulation is encapsulated by coating particles or granules of the pharmaceutical composition of the invention with varying thickness of slowly soluble polymers or by microencapsulation. In a preferred embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, preferably 20 to 25%, and the amount of coating will be from 10 to 25% of the weight of the active material. Preferably 15 to 20%. Any conventional pharmaceutically acceptable plasticizer may be incorporated into the coating.

The compounds of the invention can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiological solvents may be formulated for administration by inhalation or insufflation (either through the mouth or the nose) or oral, buccal, parenteral, or rectal administration, as examples.

Preparations for oral administration may be suitably formulated to give controlled release of the active compound. In a preferred embodiment, the compounds of the present invention are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compounds of the invention may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

General Experimental Procedures

All solvents were distilled before use and were removed by rotary evaporation at temperatures up to 35° C. Octadecyl functionalized silica gel (C18) was used for reversed phase (RP) flash chromatography, and Merck silica gel 60, 200-400 mesh, 40-63 μm, was used for silica gel flash chromatography. Thin layer chromatography (TLC) was carried out using Merck DC-plastikfolien Kieselgel 60 $F_{254}$, first visualized with a UV lamp, and then by dipping in a vanillin solution (1% vanillin, 1% $H_2SO_4$ in ethanol), and heating. Optical rotations were measured on a Perkin-Elmer 241 polarimeter. Mass spectra were recorded on a Kratos MS-80 instrument. NMR spectra, at 25° C., were recorded at 500 or 300 MHz for $^1H$ and 125 or 75 MHz for $^{13}C$ on Varian INOVA-500 or VXR-300 spectrometers. Chemical shifts are given in ppm on the delta scale referenced to the solvent peaks $CHCl_3$ at 7.25 and $CDCl_3$ at 77.0 ppm, $(CH_3)_2CO$ at 2.15 and $(CD_3)_2CO$ at 30.5 ppm, or $CH_3OD$ at 3.30 and $CD_3OD$ at 39.0 ppm.

HPLC Conditions

The analytical HPLC equipment consisted of a Waters 717 autosampler, 600 pump and controller, and a 2487 UV detector controlled by Omega software. Samples were analyzed by using an RP-18 semi-preparative column (Phenomenex Prodigy 5 mm C18 100A, 250×4.6 mm) with a guard column (Phenomenex SecurityGuard cartridge containing a C18 ODS 4×3 mm, 5 mm column) fitted at 30° C. Samples (5 ml) were analyzed using a mobile phase flow rate of 5.0 ml/min, with UV detection at 280 nm.

| Method 1 | | |
| --- | --- | --- |
| Time (minutes) | $CH_3CN$ | $H_2O$ containing 0.1% TFA |
| 0 | 11 | 89 |
| 20 | 11 | 89 |
| 30 | 100 | 0 |
| 31 | 11 | 89 |
| 40 | 11 | 89 |

| Method 2 | | |
| --- | --- | --- |
| Time (minutes) | $CH_3CN/H_2O$ (95:5) containing 0.1% TFA | $H_2O$ containing 0.1% TFA |
| 0 | 11 | 89 |
| 20 | 11 | 89 |
| 30 | 100 | 0 |
| 31 | 11 | 89 |
| 40 | 11 | 89 |

The following non-limiting Examples are given by way of illustration only and are not considered a limitation of this invention, many apparent variations of which are possible without departing from the spirit or scope thereof.

Example 1

Bis- and Tris-Dihydroxyaryl Compounds of the Invention

This Example describes bis- and tris(dihydroxyaryl) compounds that serve as potent inhibitors of inflammation and in particular the release of NO and TNF-α from microglial cells. A common structural motif that is present in all of the compounds disclosed herein is the presence of two or three dihydroxyaryl groups. These compounds are generally indicated on succeeding pages and identified variously herein by simple number.

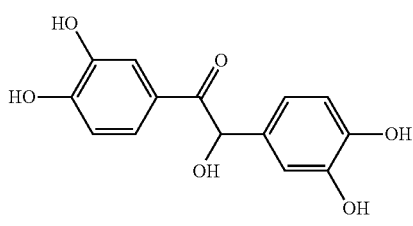

3,4,3',4'-Tetrahydroxybenzoin

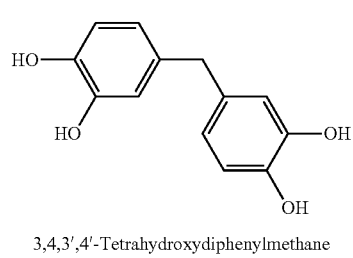

3,4,3',4'-Tetrahydroxydiphenylmethane

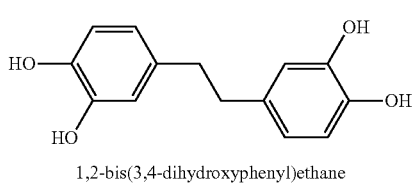

1,2-bis(3,4-dihydroxyphenyl)ethane

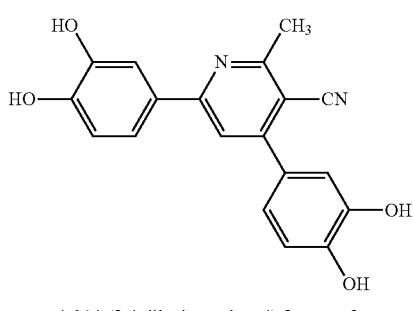

4,6-bis(3,4-dihydroxyphenyl)-3-cyano-2-methylpyridine

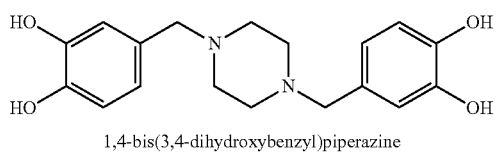

1,4-bis(3,4-dihydroxybenzyl)piperazine

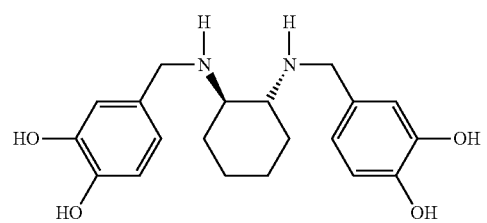

N,N'-bis(3,4-dihydroxybenzyl)-trans-1,2-diaminocyclohexane

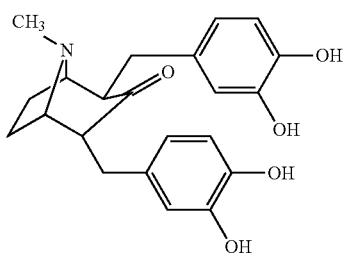

2,4-bis(3,4-dihydroxybenzyl)-3-tropinone

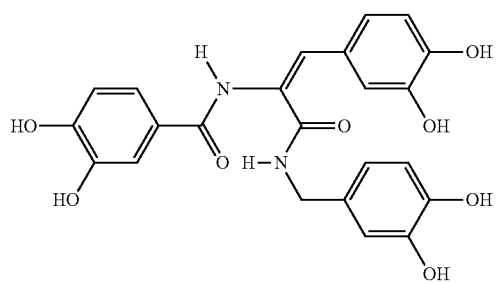

α-(3,4-dihydroxybenzamido)-3,4-dihydroxy
(-) cinnamic acid 3,4-dihydroxybenzylamide

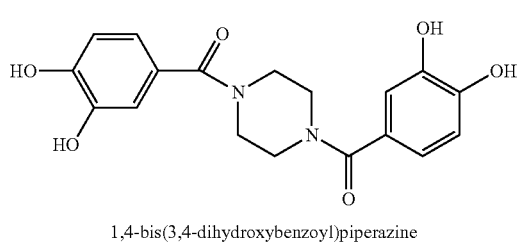

1,4-bis(3,4-dihydroxybenzoyl)piperazine

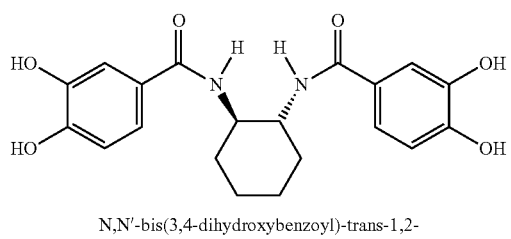

N,N'-bis(3,4-dihydroxybenzoyl)-trans-1,2-
diaminocyclohexane

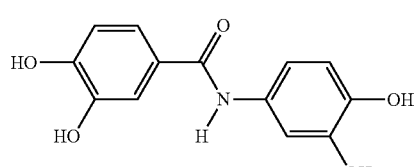

3,4-dihydroxybenzoic acid 3,4-dihydroxy-anilide

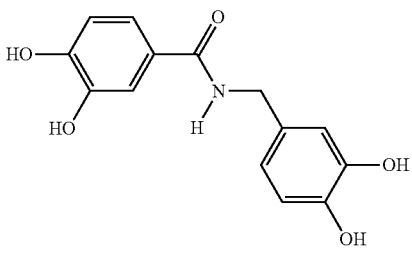

3,4-dihydroxybenzoic acid 3,4-dihydroxy-benzylamide

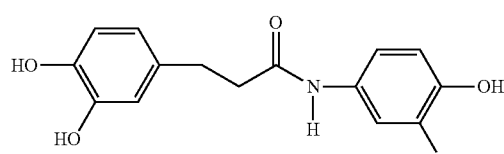

3-(3,4-dihydroxyphenyl)propionic acid 3,4-
dihydroxyanilide

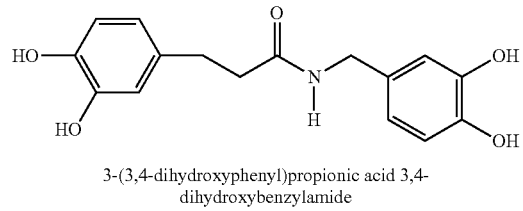

3-(3,4-dihydroxyphenyl)propionic acid 3,4-
dihydroxybenzylamide

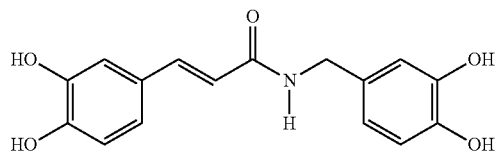

3,4-dihydroxycinnamic acid 3,4-
dihydroxybenzylamide

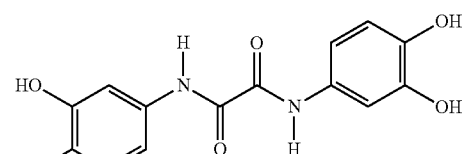

Oxalic acid bis-(3,4-dihydroxy(-)anilide)

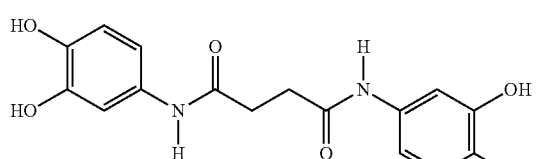

Succinic acid bis-(3,4-dihydroxyanilide)

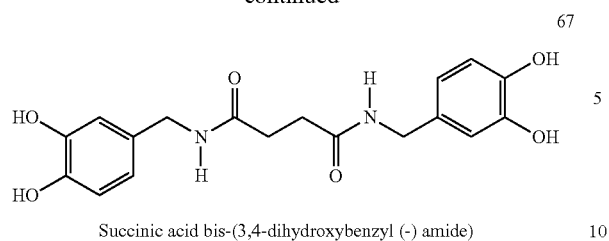
Succinic acid bis-(3,4-dihydroxybenzyl (-) amide)

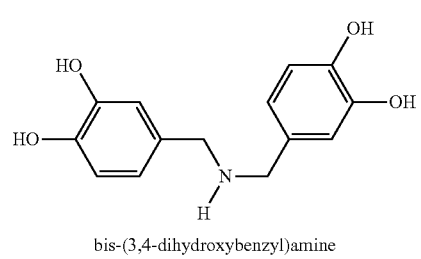
bis-(3,4-dihydroxybenzyl)amine

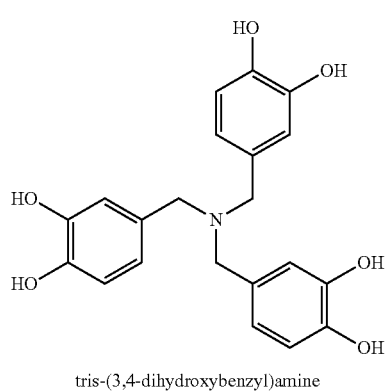
tris-(3,4-dihydroxybenzyl)amine

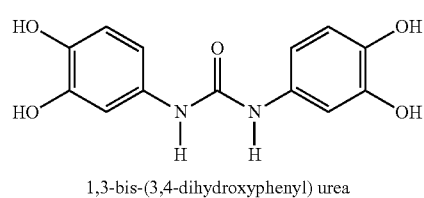
1,3-bis-(3,4-dihydroxyphenyl) urea

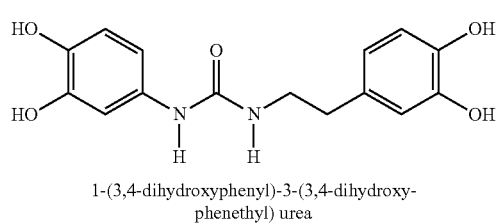
1-(3,4-dihydroxyphenyl)-3-(3,4-dihydroxyphenethyl) urea

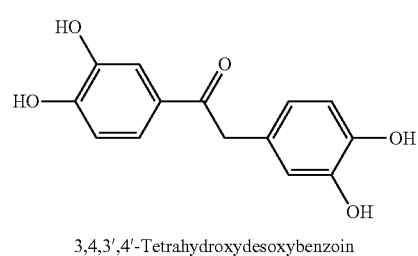
3,4,3′,4′-Tetrahydroxydesoxybenzoin

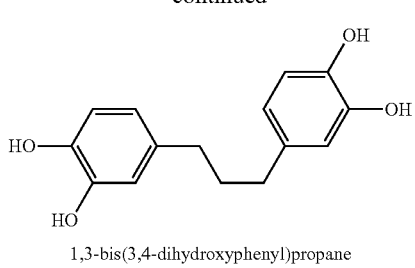
1,3-bis(3,4-dihydroxyphenyl)propane

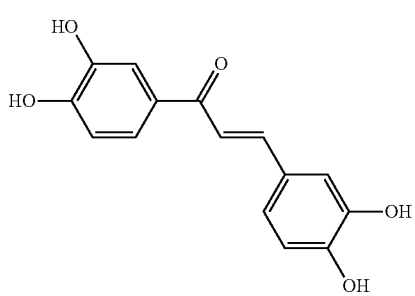
3,4,3′,4′-Tetrahydroxychalcone

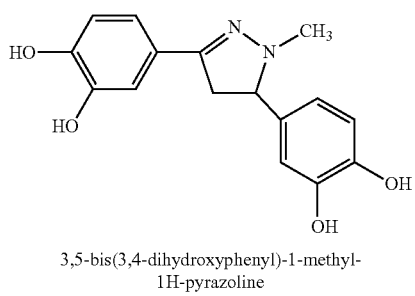
3,5-bis(3,4-dihydroxyphenyl)-1-methyl-1H-pyrazoline

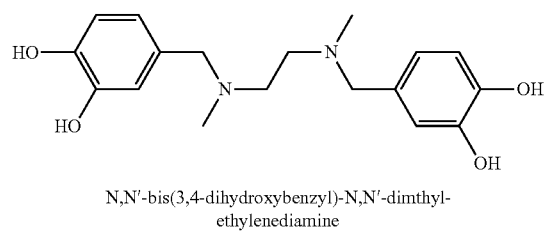
N,N′-bis(3,4-dihydroxybenzyl)-N,N′-dimthyl-ethylenediamine

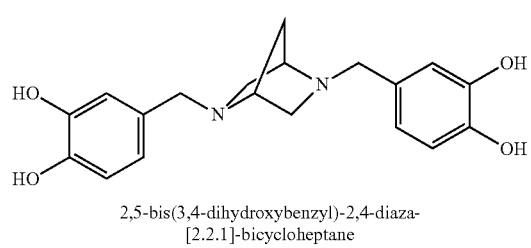
2,5-bis(3,4-dihydroxybenzyl)-2,4-diaza-[2.2.1]-bicycloheptane

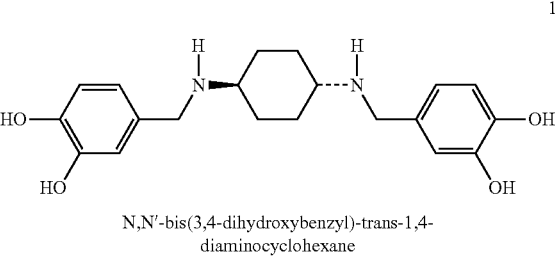
N,N′-bis(3,4-dihydroxybenzyl)-trans-1,4-diaminocyclohexane

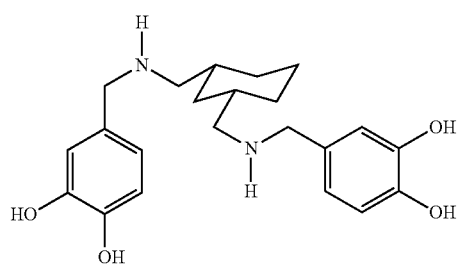

N,N'-bis(3,4-dihydroxybenzyl)-cis-1,3-
bis-aminomethylcyclohexane

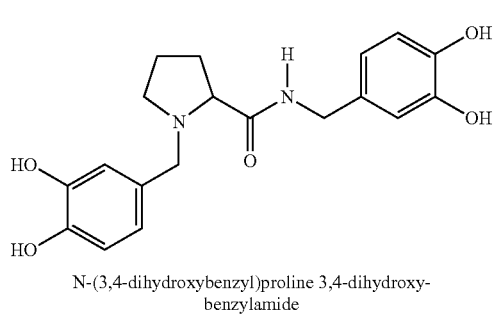

N-(3,4-dihydroxybenzyl)proline 3,4-dihydroxy-
benzylamide

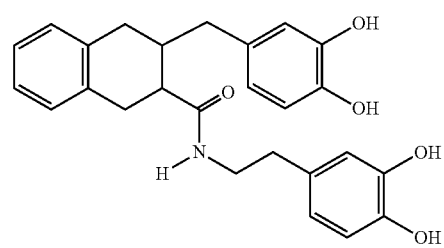

2-(3,4-hydroxybenzyl)isoquinoline-3-carboxylic
acid 3,4-dihydroxyphenethylamide

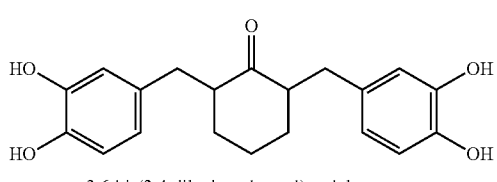

2,6-bis(3,4-dihydroxybenzyl)cyclohexanone

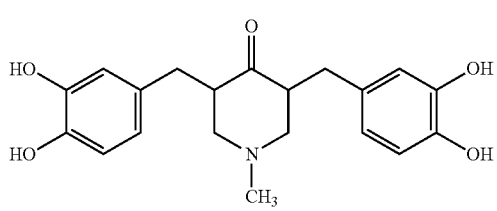

3,5-bis(3,4-dihydroxybenzyl)-1-methyl-4-
piperidinone

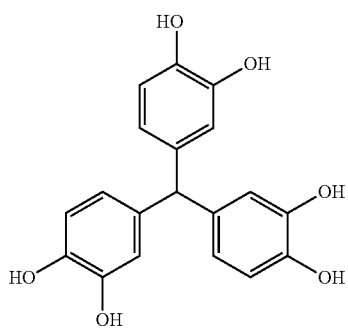

Tris-(3,4-dihydroxybenzyl)methane

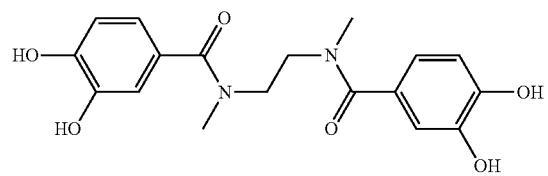

4-(3,4-dihydroxybenzylaminomethylene)-2-
(3,4-dihydroxyphenyl)oxazolin-5-one

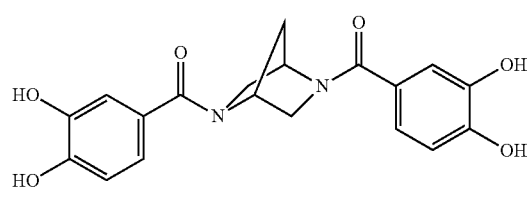

N,N'-bis(3,4-dihydroxybenzoyl)-N,N'-dimethyl
(-)ethylenediamine

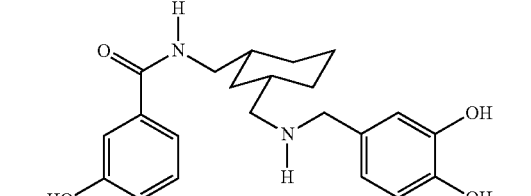

2,5-bis(3,4-dihydroxybenzoyl)-2,5-diaza-
[2.2.1]-bicycloheptane

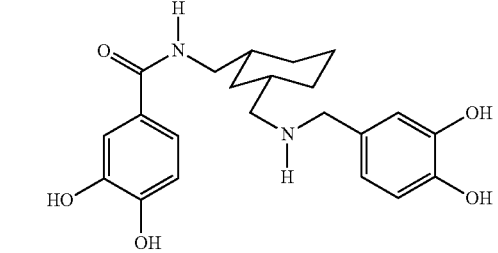

N,N'-bis(3,4-dihydroxybenzoyl)-cis-1,3-
bis-aminomethylcyclohexane

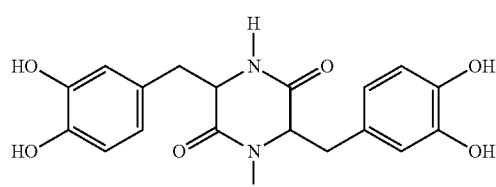
3,6-bis(3,4-dihydroxybenzyl)-1-methyl-2,5-diketopiperazine

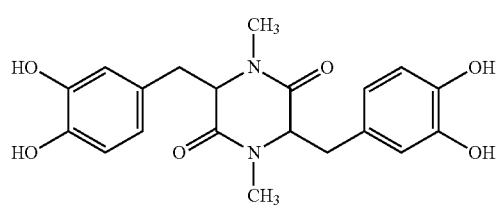
3,6-bis(3,4-dihydroxybenzylidene)-1,4-dimethyl-2,5-diketopiperazine

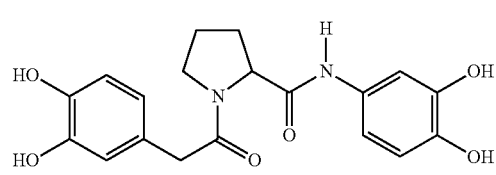
N-(3,4-hydroxyphenylacetyl)proline-3,4-dihydroxyanilide

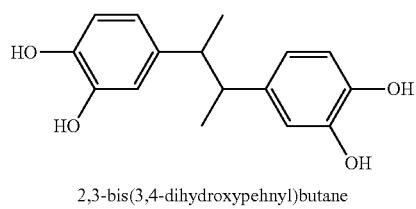
2,3-bis(3,4-dihydroxyphenyl)butane

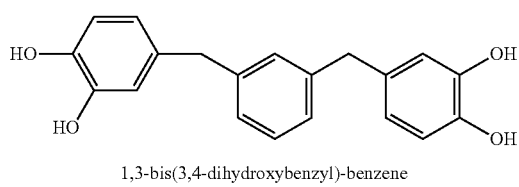
1,3-bis(3,4-dihydroxybenzyl)-benzene

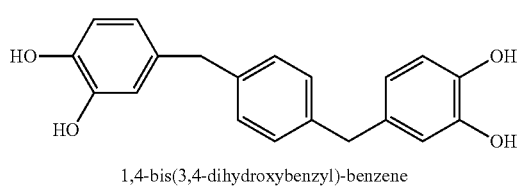
1,4-bis(3,4-dihydroxybenzyl)-benzene

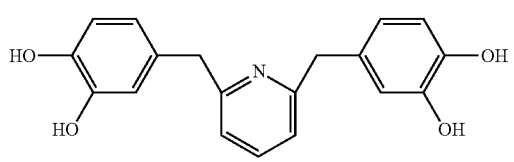
2,6-bis(3,4-dihydroxybenzyl)pyridine

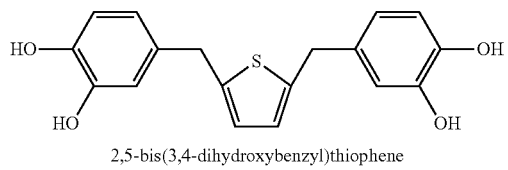
2,5-bis(3,4-dihydroxybenzyl)thiophene

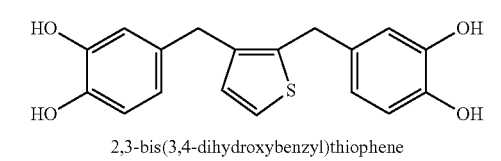
2,3-bis(3,4-dihydroxybenzyl)thiophene

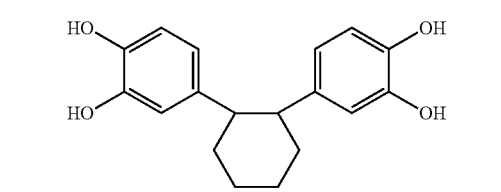
1,2-bis(3,4-dihydroxyphenyl)cyclohexane

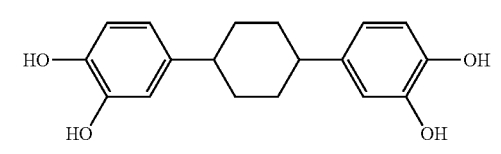
3,7-bis(3,4-dihydroxyphenyl)cyclohexane

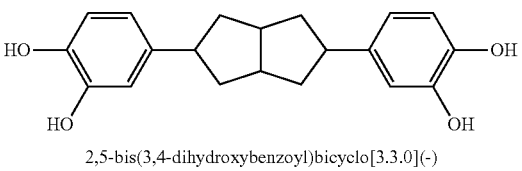
2,5-bis(3,4-dihydroxybenzoyl)bicyclo[3.3.0](-)octane

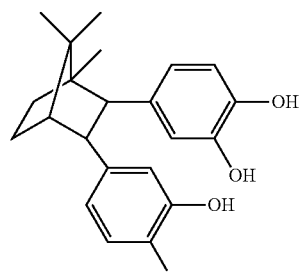
2,3-bis(3,4-dihydroxyphenyl)-1,7,7-trimethyl-bicyclo[2.2.1]heptane

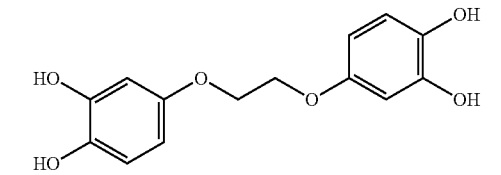
1,2-bis(3,4-dihydroxyphenoxy)ethane

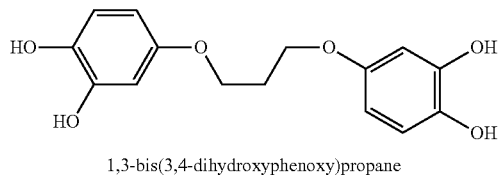

1,3-bis(3,4-dihydroxyphenoxy)propane

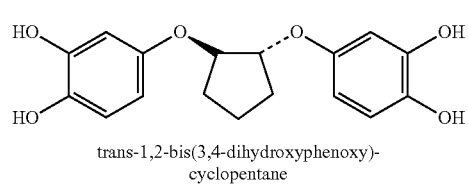

trans-1,2-bis(3,4-dihydroxyphenoxy)-cyclopentane

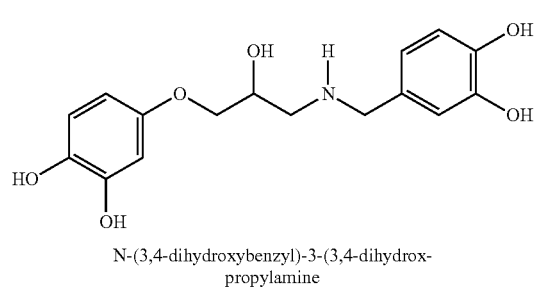

N-(3,4-dihydroxybenzyl)-3-(3,4-dihydroxpropylamine

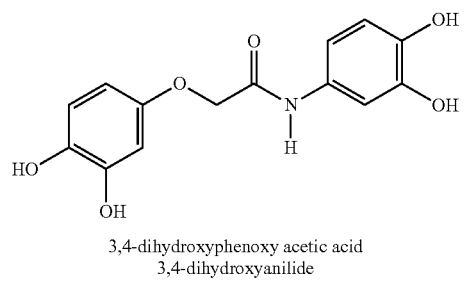

3,4-dihydroxyphenoxy acetic acid 3,4-dihydroxyanilide

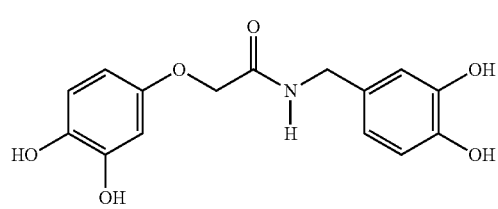

3,4-dihydroxyphenoxyacetic acid 3,4-dihydroxybenzxylamide

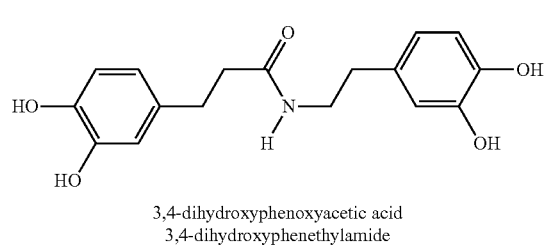

3,4-dihydroxyphenoxyacetic acid 3,4-dihydroxyphenethylamide

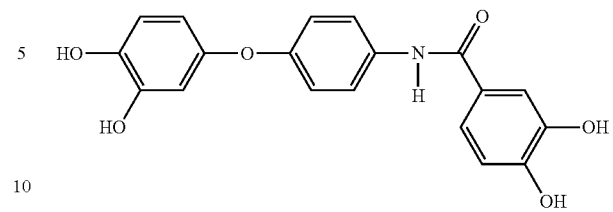

3,4-dihydroxybenzoic acid p-(3,4-dihydroxyphenoxy) anilide

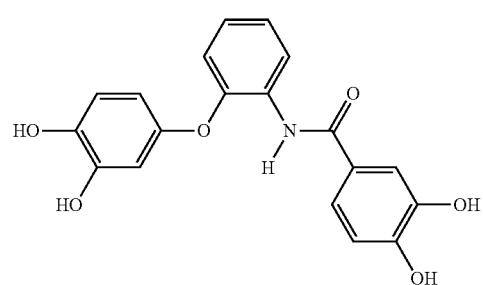

3,4-dihydroxybenzoic acid o-(3,4-dihydroxyphenoxy)anilide

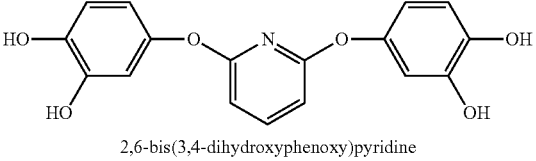

2,6-bis(3,4-dihydroxyphenoxy)pyridine

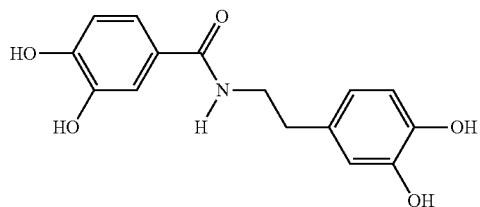

3,4-dihydroxybenzoic acid 3,4-dihydroxyphenethyl amide

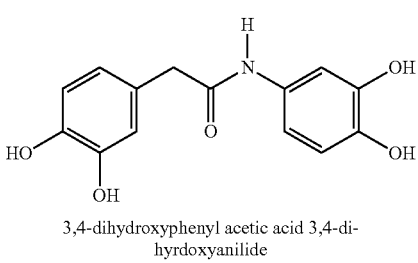

3,4-dihydroxyphenyl acetic acid 3,4-dihyrdoxyanilide

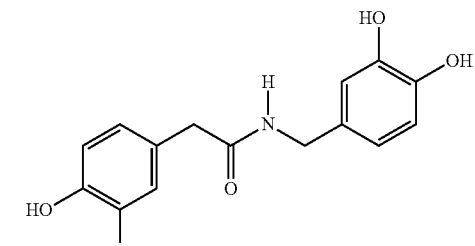

3,4-dihydroxyphenylacetic acid 3,4-dihydroxy-
benzylamide

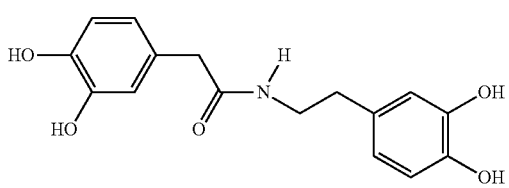

3,4-dihydroxyphenylacetic acid 3,4-dihyroxy-
phenethylamide

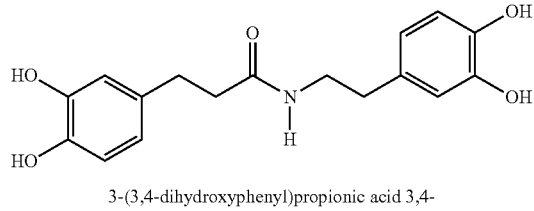

3-(3,4-dihydroxyphenyl)propionic acid 3,4-
dihydroxyphenethylamide

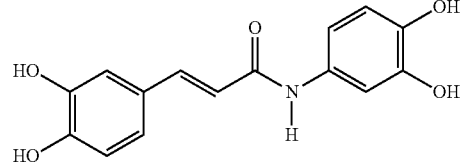

3,4-dihydroxycinnamic acid 3,4-dihydroxy-
anilide

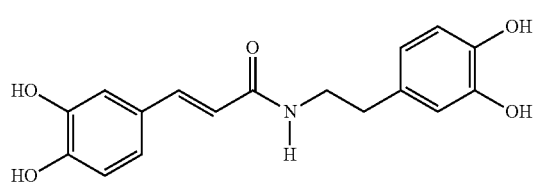

3,4-dihydroxybenzoic acid p-(3,4-di-
hydroxyphenoxy) anilide

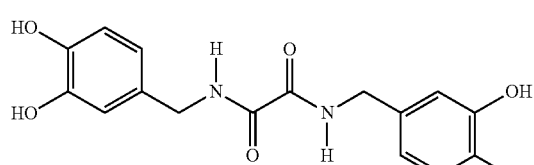

Oxalic acid-bis(3,4-dihydroxybenzyl(-) amide)

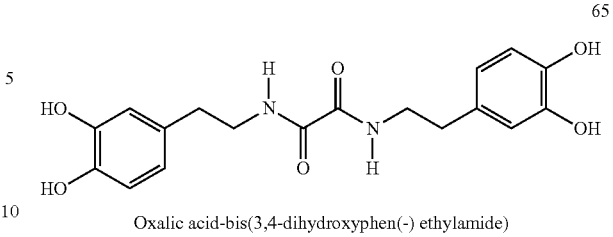

Oxalic acid-bis(3,4-dihydroxyphen(-) ethylamide)

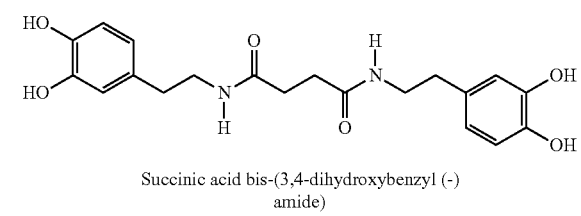

Succinic acid bis-(3,4-dihydroxybenzyl (-)
amide)

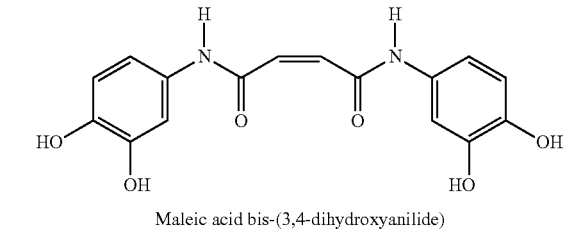

Maleic acid bis-(3,4-dihydroxyanilide)

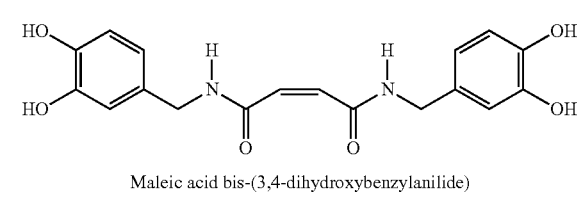

Maleic acid bis-(3,4-dihydroxybenzylanilide)

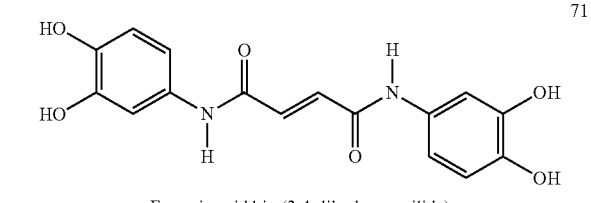

Fumaric acid bis-(3,4-dihydroxyanilide)

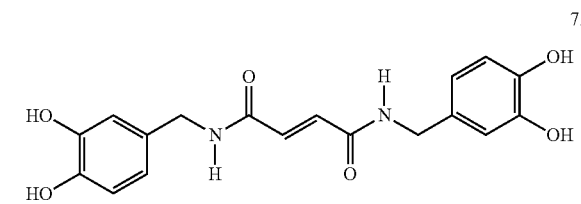

Fumaric acid bis-(3,4-dihydroxybenzylamide)

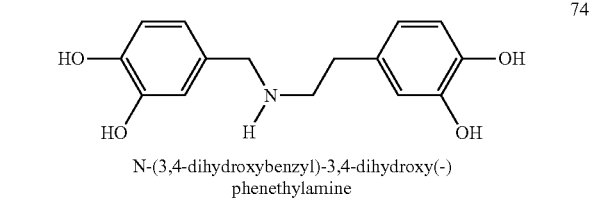

N-(3,4-dihydroxybenzyl)-3,4-dihydroxy(-)
phenethylamine

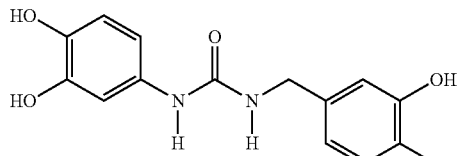

1-(3,4-dihyroxyphenyl)-3-(3,4-dihydroxybenzyl) urea

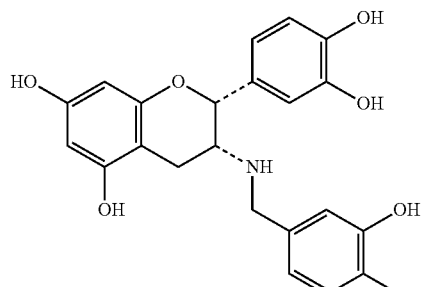

3-deoxy-3-(3,4-dihydroxybenzyl)(-)amino-epicatechin

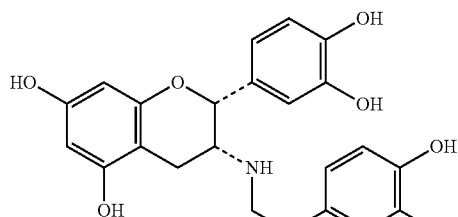

3-deoxy-3-(3,4-dihydroxyphenethyl)(-)amino-epicatechin

Example 2

Compounds of the Invention with Rigid Scaffolds

This Example illustrates six further compounds of this invention; compounds #81, 82, 83, 84, 85, and 86. These compounds have relatively rigid scaffold structures.

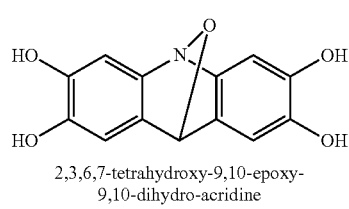

2,3,6,7-tetrahydroxy-9,10-epoxy-9,10-dihydro-acridine

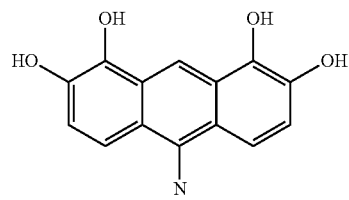

10-Amino-anthracene-1,2,7,8-tetraol

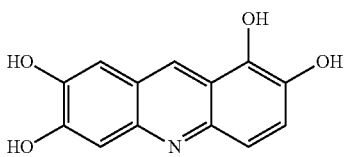

Acridine-1,2,6,7-tetraol

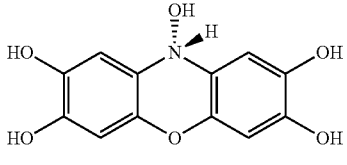

Phenoxazine-2,3,7,8,10-pentaol

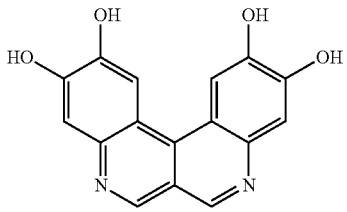

Dibenzo[c,f][2,7]naphthyridine-2,3,10,11-tetraol

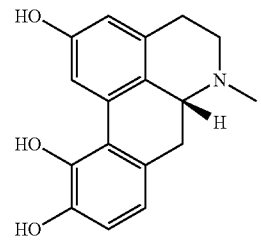

6-Methyl-5,6,6a,7-tetrahydro-4H-dibenzo[de,g]quinoline-2,10,11-triol

Example 3

Methylenedioxy Analogs

A strategy for the delivery of the dihydroxyaryl compounds of this invention to improve and/or cause more favorable metabolism and bioavailability characteristics involves the protection of the hydroxy groups of the dihydroxyaryl compounds with methylenedioxy groups. This strategy is exemplified in the 80 structures shown below, and is equally applicable to protect the dihydroxyaryl groups of compounds #81-86. Methylenedioxy analogs represent intermediate hydroxy protecting structures that are made to successfully complete the synthesis of the dihydroxyaryl compounds described in the invention. These closed-ring compounds also tend to be more stable, and hydrophobic (water insoluble), and less likely to be altered or degraded due to the oxidation that could occur if hydroxyl groups were present. In addition, these compounds make good prodrugs for delivery. Hydrophobic compounds that are lipid soluble tend to be attractive compounds for delivery since they are usually able to penetrate the blood-brain-barrier.

The methylenedioxy analogs are generally available as intermediates in the synthesis of the corresponding dihydroxyaryl compounds. These compounds are expected to be efficacious once the methylenedioxy structures are cleaved to yield hydroxyl groups. Conversion of the hydroxyl groups to methylenedioxy derivatives also yields prodrugs that are believed to improve toxicity (i.e. being less toxic), metabolism (since the OH groups will be less likely to be altered by methylation, glucuronidation and sulfation), and bioavailability. In this prodrug concept, it is believed that the prodrug conversion takes place in the plasma (following its protection through the gut), and closer to its appropriate target tissue (systemic organs). Enzymes in the blood and appropriate tissues are believed to be able to cleave the methylenedioxy group on these analogs to yield the dihydroxy structures to achieve the observed efficacy.

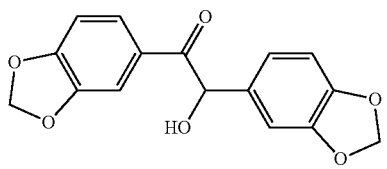

1B bis(3,4-methylenedioxy)benzoin

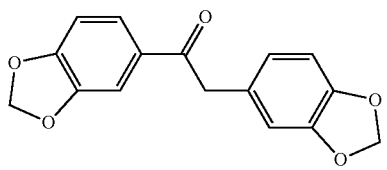

2B bis(3,4-methylenedioxy)desoxybenzoin

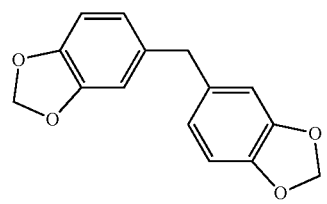

3B 1,1-bis(3,4-methylenedioxyphenyl)methane

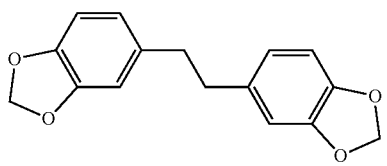

4B 1,2-bis(3,4-methylenedioxyphenyl)ethane

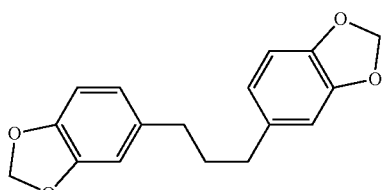

5B 1,3-bis(3,4-methylenedioxyphenyl)propane

-continued

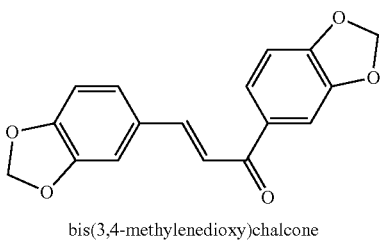

6B bis(3,4-methylenedioxy)chalcone

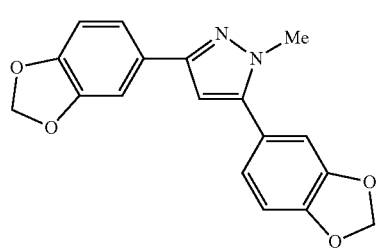

7B 3,5-bis(3,4-methylenedioxyphenyl-
1-methyl-1H-pyrazoline

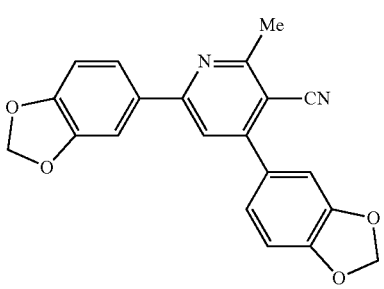

8B 4,6-bis(3,4-methylenedioxyphenyl)-
3-cyano-2-methylpyridine

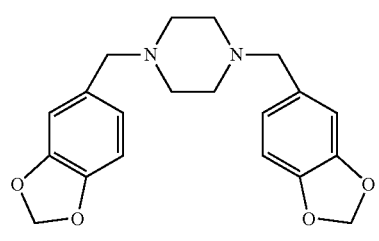

9B 1,4-bis(3,4-methylenedioxybenzyl)piperazine

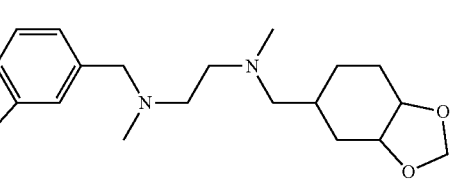

10B

N,N'-bis(3,4-methylenedioxybenzyl)-
N,N'-dimethyl-ethylenediamine

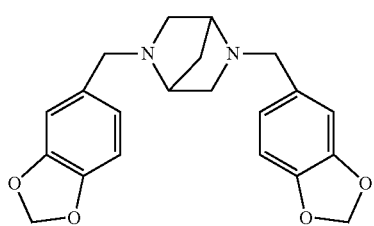

2,5-bis(3,4-methylenedioxybenzyl)-2,5-
diaza[2,2,1]-bicycloheptane

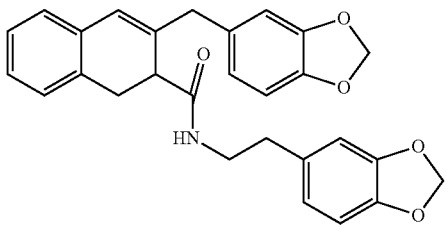

2-(3,4-methylenedioxybenzyl)isoquinoline-3-
carboxylic acid 3,4-
methylenedioxyphenethylamide

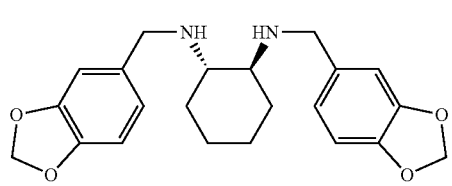

N,N'-bis(3,4-methylenedioxybenzyl)-trans-
1,2-diaminocyclohexane

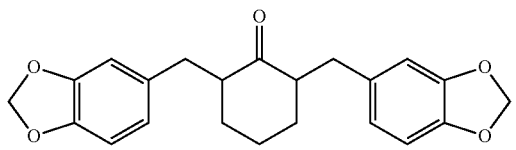

2,6-bis(3,4-methylenedioxybenzyl)
cyclohexanone

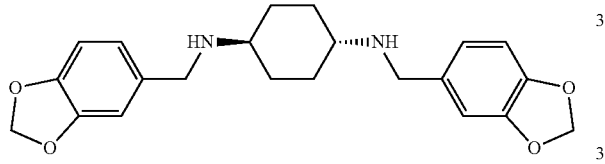

N,N'-bis(3,4-methylenedioxybenzyl)-trans-
1,4-diaminocyclohexane

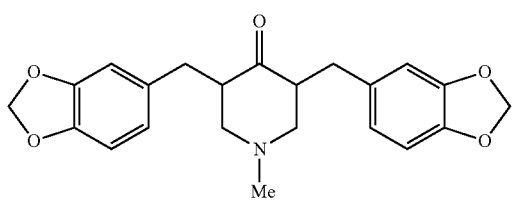

3,5-bis(3,4-methylenedioxybenzyl)-1-methyl-4-
piperidinone

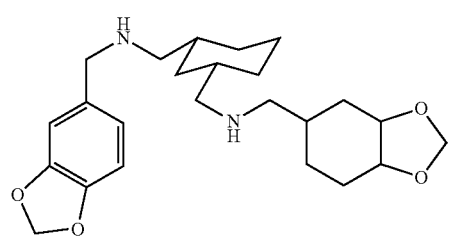

N,N'-bis(3,4-methylenedioxybenzyl)-cis-
1,3-bis-aminomethylcyclohexane

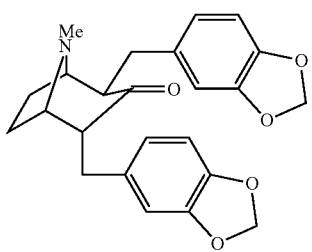

2,4-bis(3,4-methylenedioxybenzyl)-3-tropinone

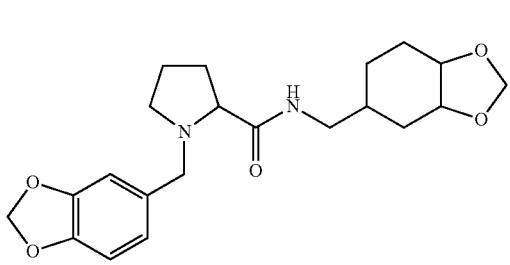

N-(3,4-methylenedioxybenzyl)proline 3,4-
methylenedioxybenzylamide

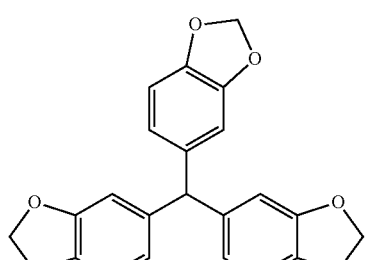

Tris-(3,4-methylenedioxyphenyl)methane

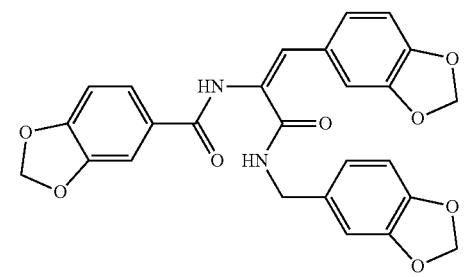

α-(3,4-methylenedioxybenzamido)-3,4-
methylenedioxy(-)cinnamic acid 3,4-
methylenedioxybenzyl amide

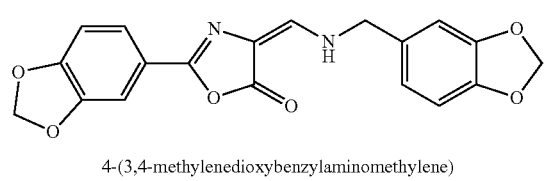

4-(3,4-methylenedioxybenzylaminomethylene)
-2-(3,4-methylenedioxyphenyl)oxazolin-5-one

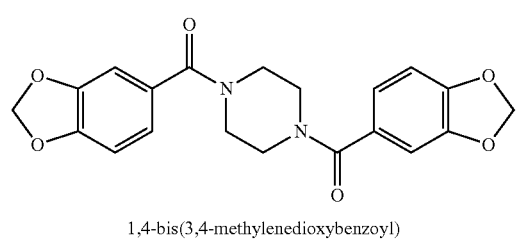

1,4-bis(3,4-methylenedioxybenzoyl)
piperazine

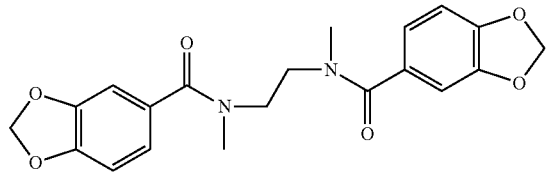

N,N'-bis(3,4-methylenedioxybenzoyl)-
N,N'-dimethyl(-)ethylenediamine

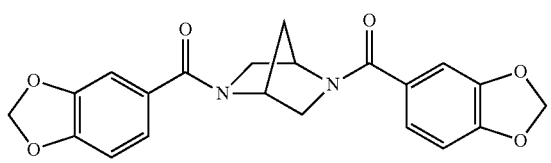

2,5-bis(3,4-methylenedioxybenzoyl)-2,5-
diaza[2,2,1]-bicycloheptane

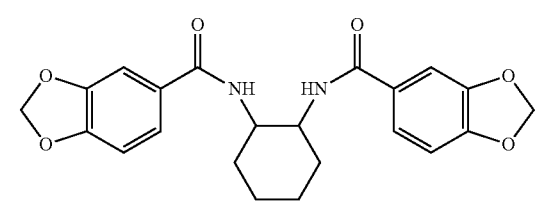

N,N'-bis(3,4-methylenedioxybenzoyl)-trans-
diaminocyclohexane

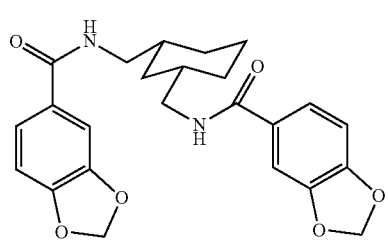

N,N'-bis(3,4-methylenedioxybenzoyl)-cis-
1,3-bis-aminomethylcyclohexane

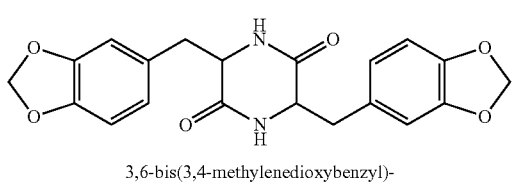

3,6-bis(3,4-methylenedioxybenzyl)-
2,5-diketopiperazine

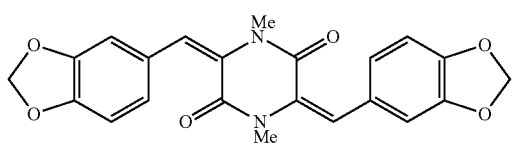

3,6-bis(3,4-methylenedioxybenzylidene)-
1,4-dimethyl-2,5--diketopiperazine

N-(3,4-methylenedioxyphenylacetyl)-
proline-3,4-methylenedioxyanilide

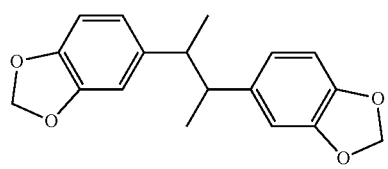

2,3-bis(3,4-methylenedioxyphenyl)
butane

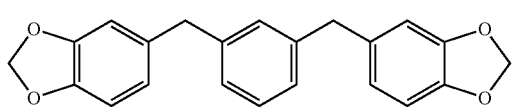

1,3-bis(3,4-methylenedioxybenzyl)benzene

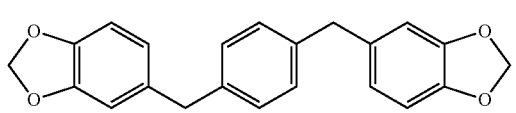

1,4-bis(3,4-methylenedioxybenzyl)
benzene

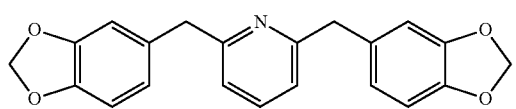

2,6-bis(3,4-methylenedioxybenzyl) pyridine

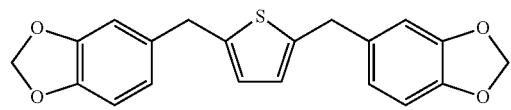

2,5-bis(3,4-methylenedioxybenzyl) thiophene

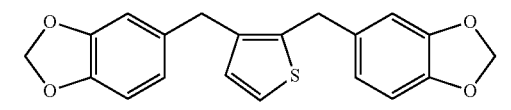

2,3-bis(3,4-methylenedioxybenzyl) thiophene

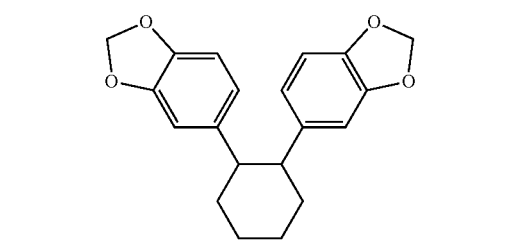

1,2-bis(3,4-methylenedioxyphenyl) cyclohexane

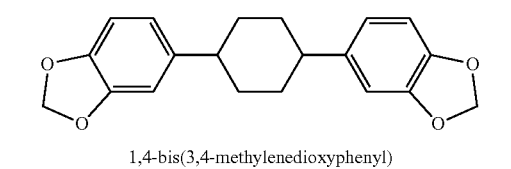

1,4-bis(3,4-methylenedioxyphenyl) cyclohexane

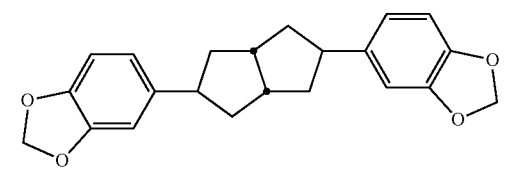

3,7-bis(3,4-methylenedioxyphenyl) bicyclo[3,3,0](-)octane

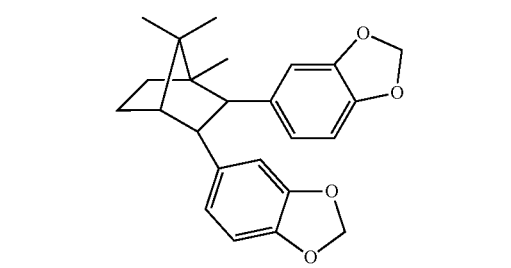

2,3-bis(3,4-methylenedioxyphenyl)-1,7,7-trimethyl-bicyclo[2,2,1]heptane

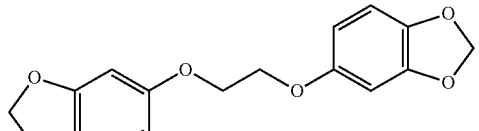

1,2-bis(3,4-methylenedioxyphenoxy)ethane

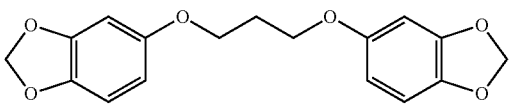

1,3-bis(3,4-methylenedioxyphenoxy)propane

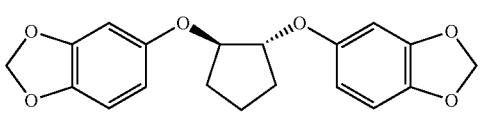

trans-1,2-bis(3,4-methylenedioxyphenoxy)(-)cyclopentane

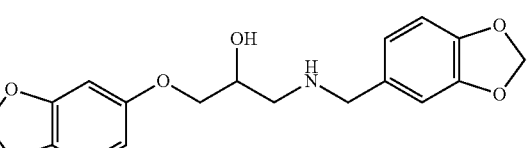

N-(3,4-methylenedioxybenzyl)-3-(3,4-methylenedioxy(-)phenoxy)-2-hydroxypropylamine

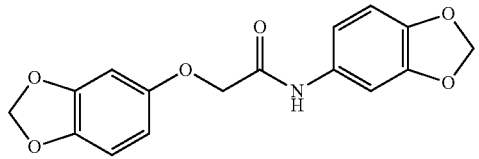

3,4-methylenedioxyphenoxy acetic acid 3,4-methylenedioxyanilide

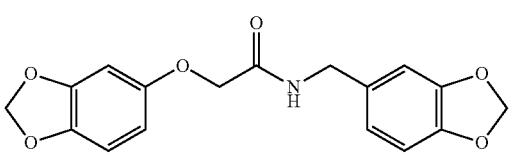

3,4-methylenedioxyphenoxyacetic acid 3,4-methylenedioxybenzylamide

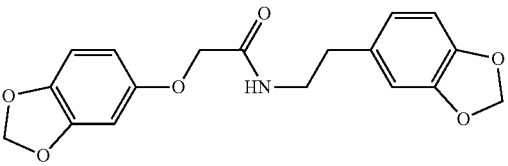

3,4-methylenedioxyphenoxy acetic acid 3,4-methylenedioxyphenethylamide

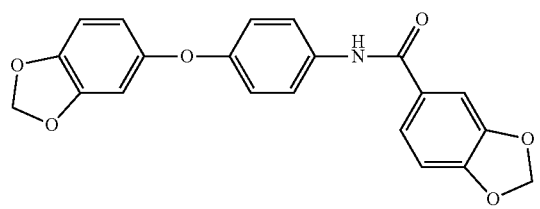

3,4-methylenedioxybenzoic acid p-(3,4-methylenedioxyphenoxy)anilide

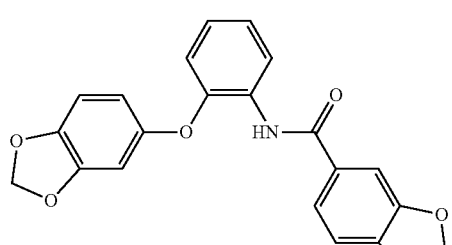

3,4-methylenedioxybenzoic acid o-(3,4-methylenedioxyphenoxy)anilide

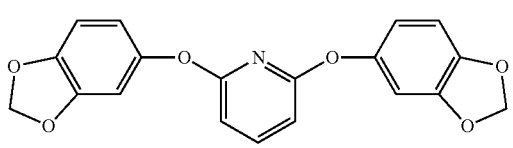

2,6-bis(3,4-methylenedioxyphenoxy) pyridine

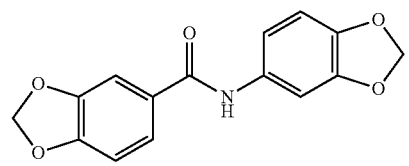

3,4-methylenedioxybenzoic acid 3,4-methylenedioxyanilide

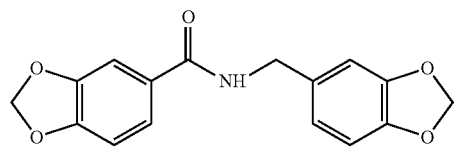

3,4-methylenedioxybenzoic acid 3,4-methylenedioxybenzylamide

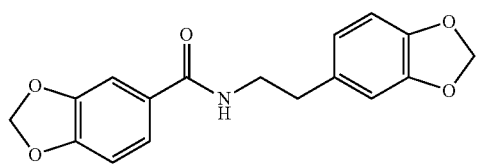

3,4-methylenedioxybenzoic acid 3,4-methylenedioxyphenethylamide

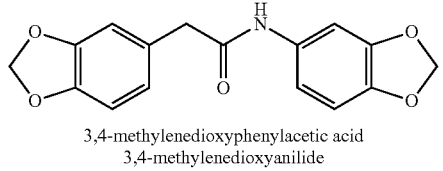

3,4-methylenedioxyphenylacetic acid 3,4-methylenedioxyanilide

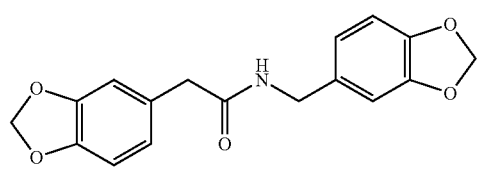

3,4-methylenedioxyphenylacetic acid 3,4-methylenedioxybenzylamide

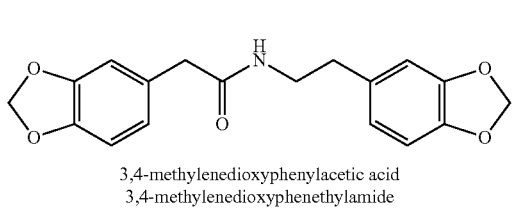

3,4-methylenedioxyphenylacetic acid 3,4-methylenedioxyphenethylamide

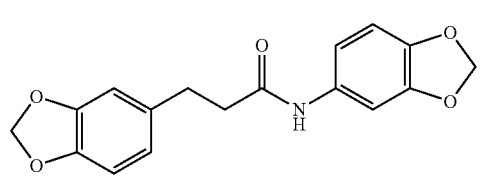

3-(3,4-methylenedioxyphenyl) propionic acid 3,4-methylenedioxyanilide

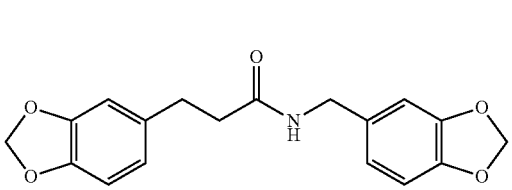

3-(3,4-methylenedioxyphenyl) propionic acid 3,4-methylenedioxybenzylamide

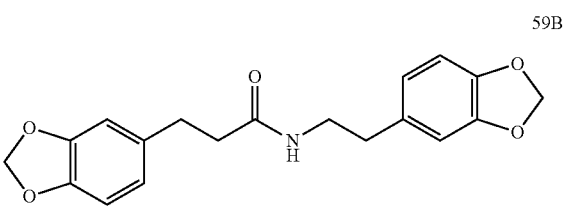

3-(3,4-methylenedioxyphenyl) propionic acid 3,4-methylenedioxyphenethylamide

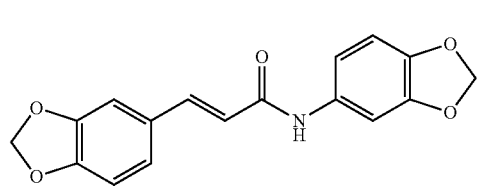

3,4-methylenedioxycinnamic acid 3,4-methylenedioxyanilide

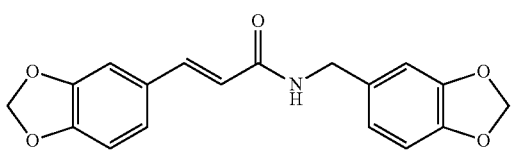

3,4-methylenedioxycinnamic acid
3,4-methylenedioxybenzylamide
61B

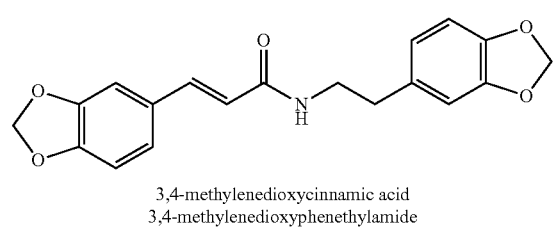

3,4-methylenedioxycinnamic acid
3,4-methylenedioxyphenethylamide
62B

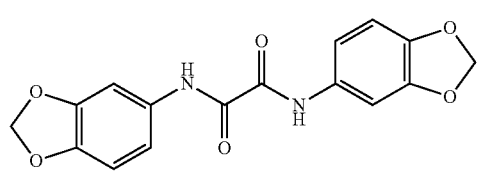

Oxalic acid bis(3,4-methylene-
dioxyanilide)
63B

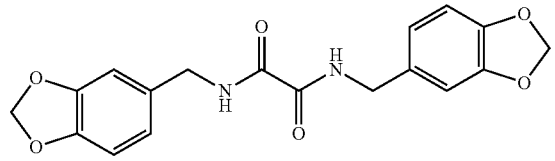

Oxalic acid bis(3,4-methylene-
dioxybenzylamide)
64B

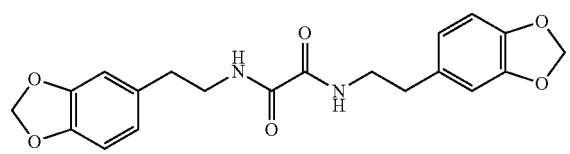

Oxalic acid bis(3,4-methylene-
dioxyphenethylamide)
65B

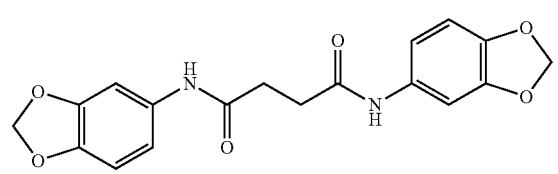

Succinic acid bis(3,4-methylene-
dioxyanilide)
66B

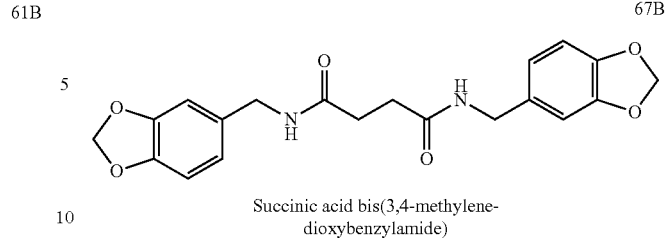

Succinic acid bis(3,4-methylene-
dioxybenzylamide)
67B

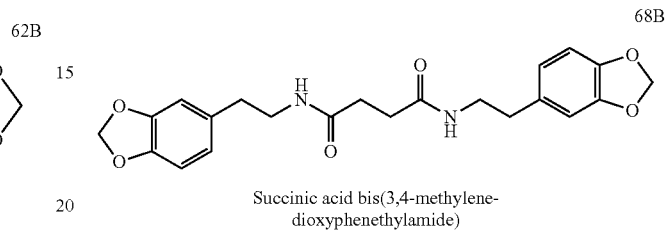

Succinic acid bis(3,4-methylene-
dioxyphenethylamide)
68B

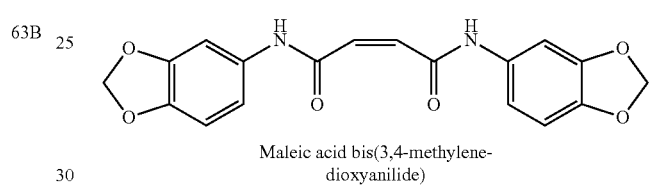

Maleic acid bis(3,4-methylene-
dioxyanilide)
69B

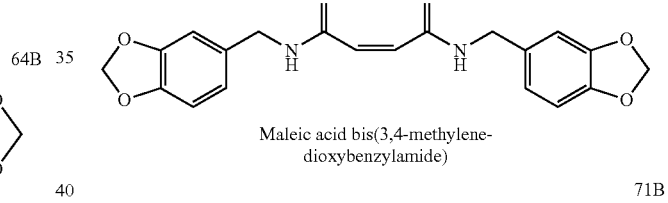

Maleic acid bis(3,4-methylene-
dioxybenzylamide)
70B

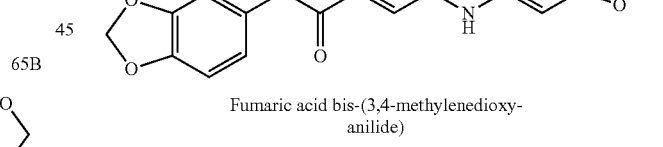

Fumaric acid bis-(3,4-methylenedioxy-
anilide)
71B

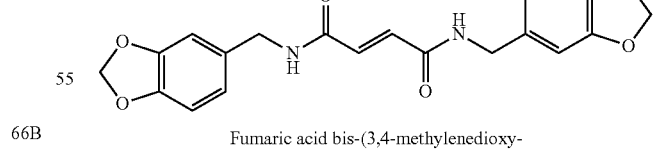

Fumaric acid bis-(3,4-methylenedioxy-
benzylamide)
72B

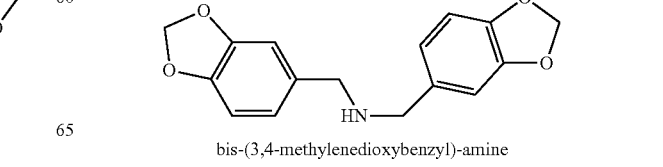

bis-(3,4-methylenedioxybenzyl)-amine
73B

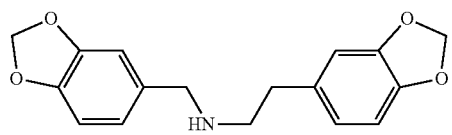

N-(3,4-methylenedioxybenzyl)-
3,4-methylenedioxyphenethylamine

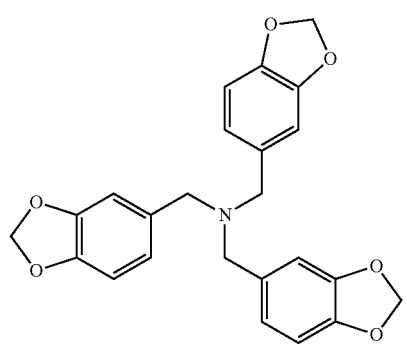

tris-(3,4-methylenedioxybenzyl)-
amine

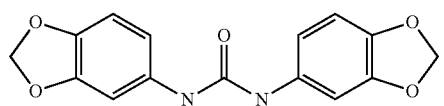

1,3-bis-(3,4-methylenedioxyphenyl)-urea

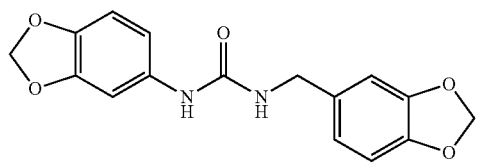

1-(3,4-methylenedioxyphenyl)-3-
(3,4-methylenedioxybenzyl)urea

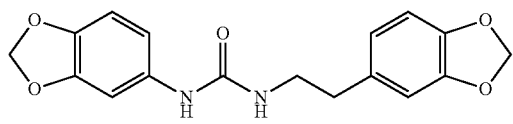

1-(3,4-methylenedioxyphenyl)-3-
(3,4-methylenedioxyphenethyl)urea

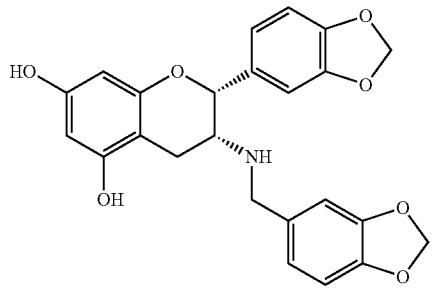

3-deoxy-3-(3,4-methylenedioxybenzyl)-
aminoepicatechin

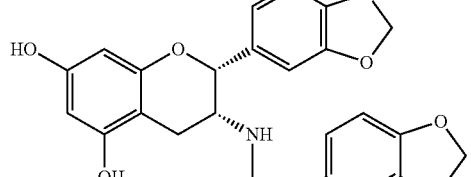

3-deoxy-3-(3,4-methylenedioxyphenethyl)-
aminoepicatechin

Example 4

Acetylated Compounds

Another potential strategy for the delivery of the bis- and tris-dihydroxyaryl compounds of this invention to improve and/or cause more favorable metabolism and bioavailability characteristics, involves methods of protecting the hydroxy groups as their pharmaceutically acceptable esters. Ester groups replacing the hydroxy groups also tend to make the compounds more stable, and less likely to be altered or degraded due to oxidation of the hydroxyl groups.

The compound table below illustrates the acetyl esters of the 86 dihydroxyaryl compounds previously presented herein, and are presented below in which the OH groups are replaced by acetyl groups. The illustration of acetyl esters here is merely exemplary for the class of pharmaceutically acceptable esters that are part of the compounds of this invention and may be prepared by analogous methods. Other compounds disclosed herein also form pharmaceutically acceptable esters in the same manner, and these compounds, though not illustrated in the compound table below, are also compounds of this invention.

These compounds are expected to be efficacious once the ester linkages are cleaved (by enzymes in the plasma or in the brain tissue), and the hydroxyl groups are regenerated. Replacement of the hydroxyl groups with ester groups will yield prodrugs that are believed to improve toxicity (i.e. being less toxic), metabolism (since the OH groups will be less likely to be altered by methylation, glucuronidation and sulfation), and bioavailability. In this prodrug concept, it is believed that the prodrug conversion takes place in the plasma (following its protection through the gut), and closer to its appropriate target tissue. Enzymes in the blood and appropriate tissues are believed to be able to cleave the ester linkages on these pharmaceutically acceptable esters to yield the dihydroxy structures important for the observed efficacy.

The pharmaceutically acceptable esters of compounds #1 through #86 are prepared by methods well known to persons of ordinary skill in the art, such as by reaction of the dihydroxyaryl compounds with pharmaceutically acceptable acids, especially in activated form (such as the acyl halides) and/or in the presence of reagents facilitating esterification (such as an acidic catalyst) and/or under conditions favoring esterification (such as by conducting the reaction under conditions where the water formed in the esterification is removed, e.g. by distillation). Methods of esterification of phenolic hydroxyl groups are well known to persons of ordinary skill in the art.

Suitable acids for the formation of pharmaceutically acceptable esters are the $C_{2-6}$ alkanoic acids (acetic acid, propionic acid, and the like), benzoic acid, arylalkanoic acids (phenylacetic acid, and the like); though many other acids are suitable for the formulation of pharmaceutically acceptable esters, and a person of ordinary skill in the art will have no difficulty in choosing a suitable acid.

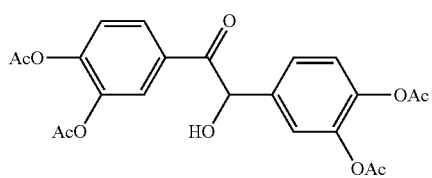

bis(3,4-diacetoxy)benzoin

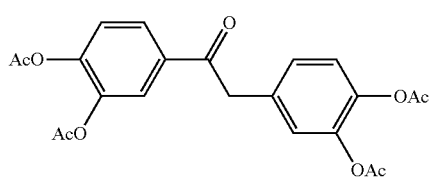

bis(3,4-diacetoxy)desoxybenzoin

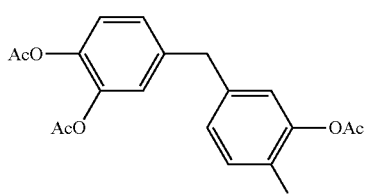

1,1-bis(3,4-diacetoxyphenyl)methane

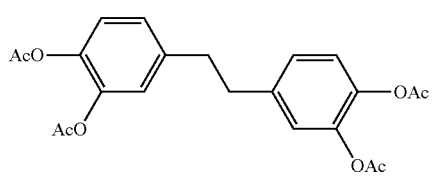

1,2-bis(3,4-diacetoxyphenyl)ethane

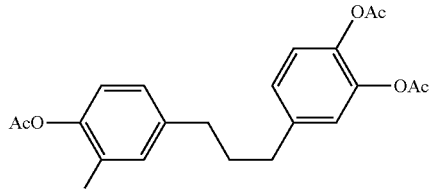

1,3-bis(3,4-diacetoxyphenyl)propane

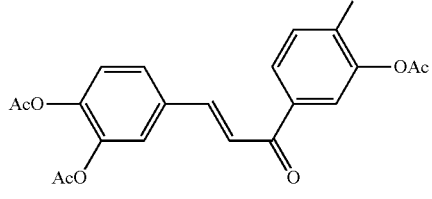

bis(3,4-diacetoxy)chalcone

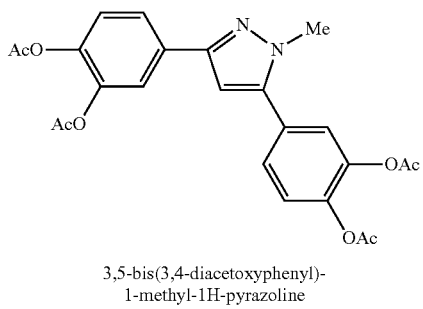

3,5-bis(3,4-diacetoxyphenyl)-1-methyl-1H-pyrazoline

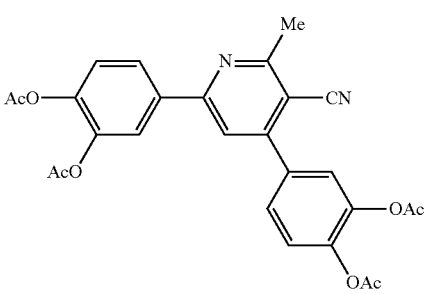

4,6-bis(3,4-diacetoxyphenyl)-3-cyano-2-methylpyridine

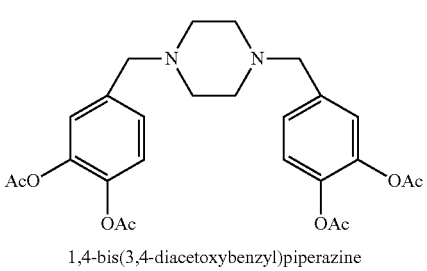

1,4-bis(3,4-diacetoxybenzyl)piperazine

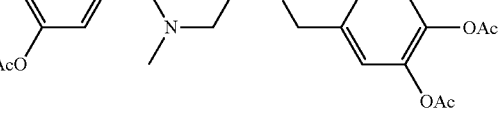

N,N'-bis(3,4-diacetoxybenzyl)-N,N'-dimethyl-ethylenediamine

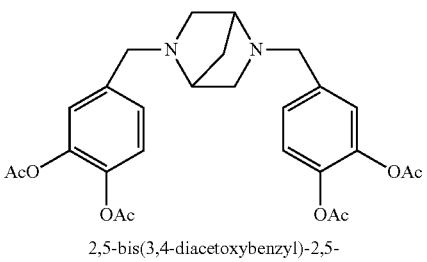

2,5-bis(3,4-diacetoxybenzyl)-2,5-diaza[2,2,1]-bicycloheptane

-continued

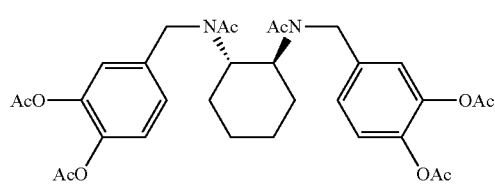

N,N′-bis(acetyl)-bis(3,4-diacetoxybenzyl)-
trans-1,2-diaminocyclohexane

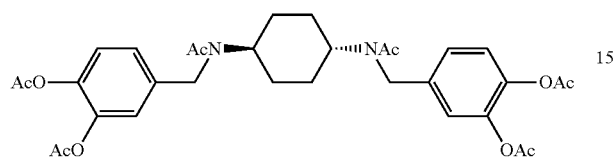

N,N′-bis(acetyl)-bis(3,4-diacetoxybenzyl)-
trans-1,4-diaminocyclohexane

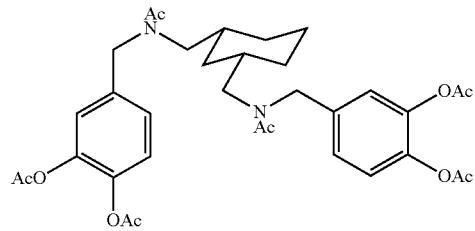

N,N′-bis(acetyl)-bis(3,4-diacetoxybenzyl)-cis-
1,3-bis-aminomethylcyclohexane

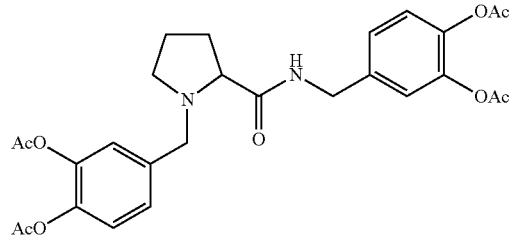

N-(3,4-diacetoxybenzyl)proline 3,4-
diacetoxybenzylamide

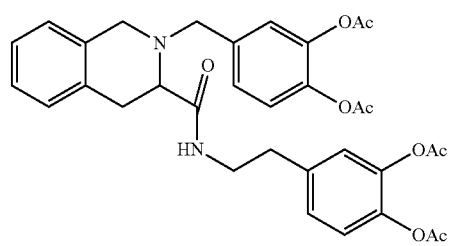

2-(3,4-diacetoxybenzyl)isoquinoline-3-
carboxylic acid 3,4-diacetoxyphenethylamide

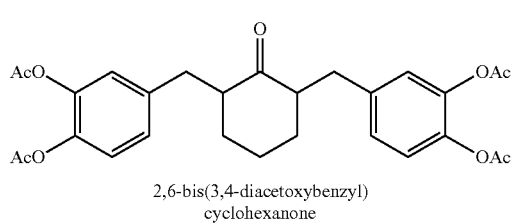

2,6-bis(3,4-diacetoxybenzyl)
cyclohexanone

-continued

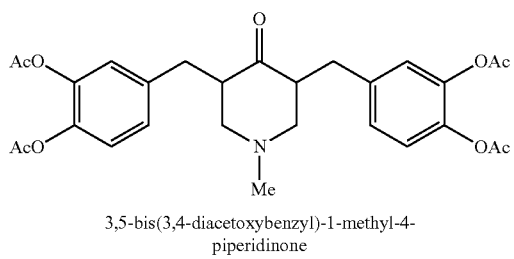

3,5-bis(3,4-diacetoxybenzyl)-1-methyl-4-
piperidinone

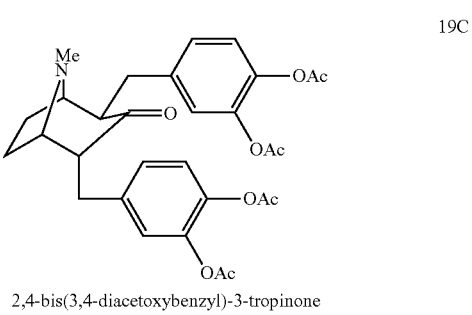

2,4-bis(3,4-diacetoxybenzyl)-3-tropinone

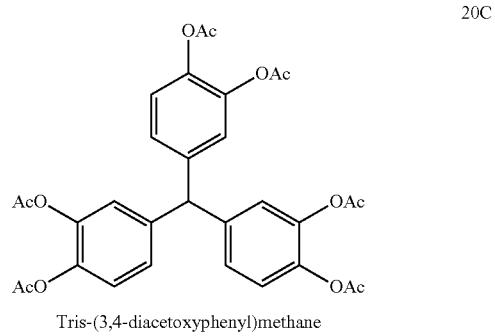

Tris-(3,4-diacetoxyphenyl)methane

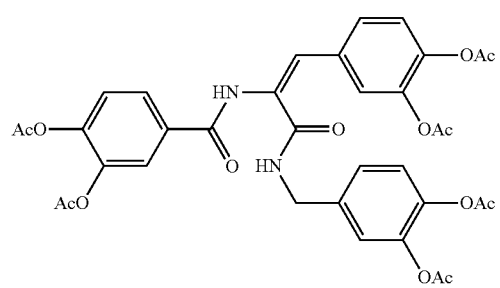

α-(3,4-diacetoxybenzamido)-3,4-
diacetoxy(-)cinnamic acid 3,4-
diacetoxybenzyl amide

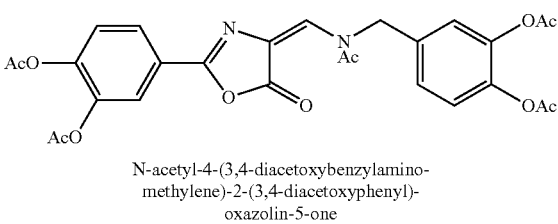

N-acetyl-4-(3,4-diacetoxybenzylamino-
methylene)-2-(3,4-diacetoxyphenyl)-
oxazolin-5-one

23C

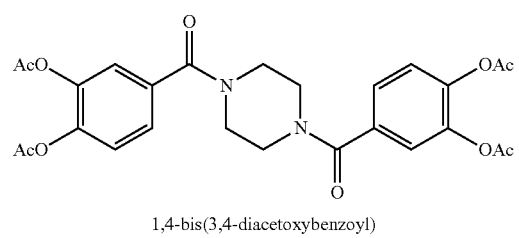

1,4-bis(3,4-diacetoxybenzoyl)
piperazine

24C

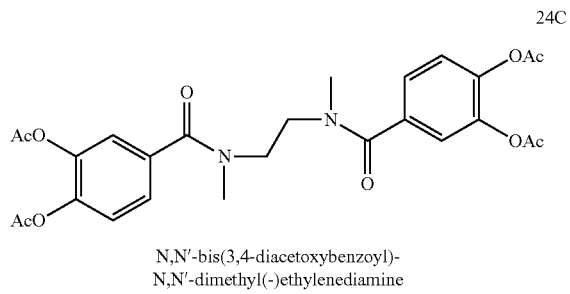

N,N'-bis(3,4-diacetoxybenzoyl)-
N,N'-dimethyl(-)ethylenediamine

25C

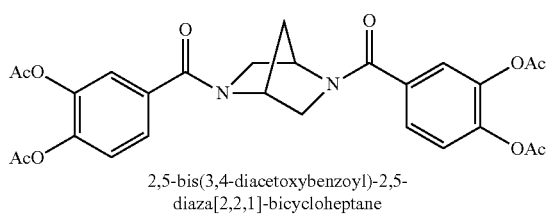

2,5-bis(3,4-diacetoxybenzoyl)-2,5-
diaza[2,2,1]-bicycloheptane

26C

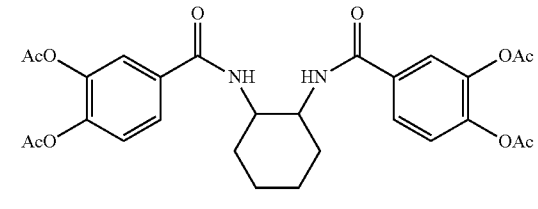

N,N'-bis(3,4-diacetoxybenzoyl)-trans-
diaminocyclohexane

27C

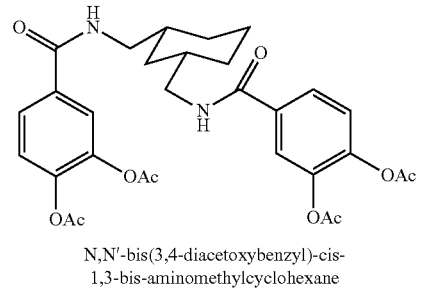

N,N'-bis(3,4-diacetoxybenzyl)-cis-
1,3-bis-aminomethylcyclohexane

28C

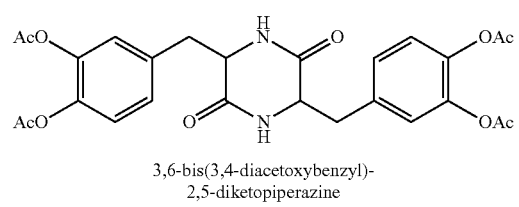

3,6-bis(3,4-diacetoxybenzyl)-
2,5-diketopiperazine

29C

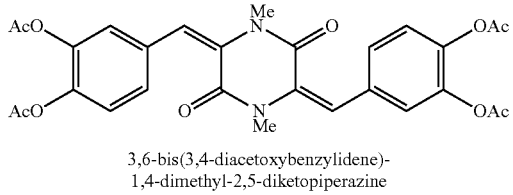

3,6-bis(3,4-diacetoxybenzylidene)-
1,4-dimethyl-2,5-diketopiperazine

30C

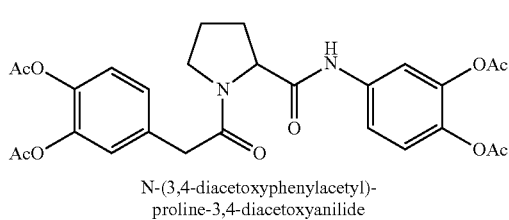

N-(3,4-diacetoxyphenylacetyl)-
proline-3,4-diacetoxyanilide

31C

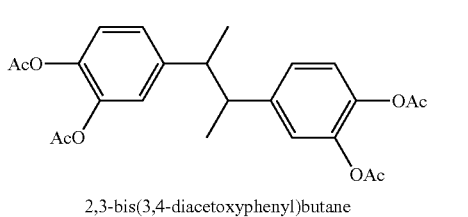

2,3-bis(3,4-diacetoxyphenyl)butane

32C

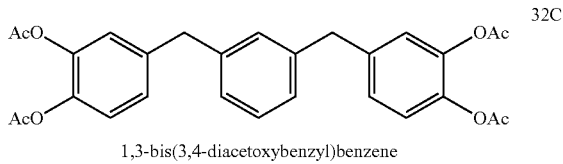

1,3-bis(3,4-diacetoxybenzyl)benzene

33C

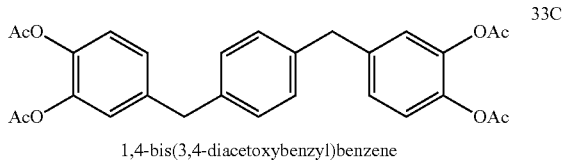

1,4-bis(3,4-diacetoxybenzyl)benzene

34C

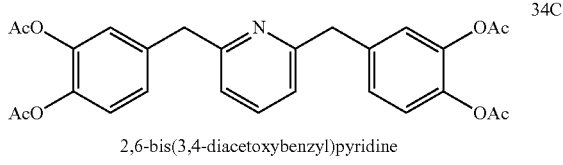

2,6-bis(3,4-diacetoxybenzyl)pyridine

35C

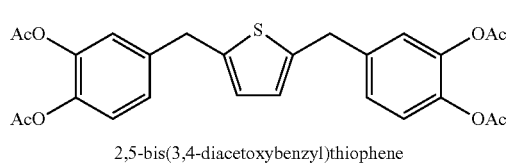

2,5-bis(3,4-diacetoxybenzyl)thiophene

36C

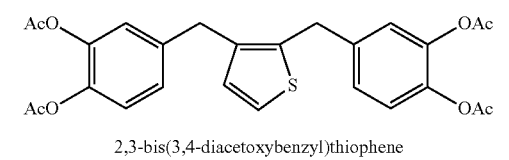

2,3-bis(3,4-diacetoxybenzyl)thiophene

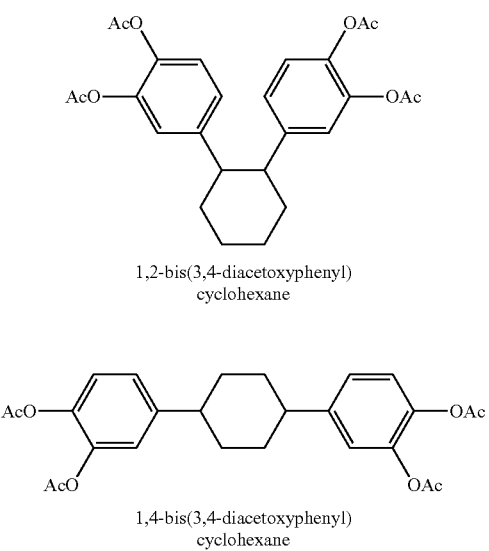

1,2-bis(3,4-diacetoxyphenyl)
cyclohexane

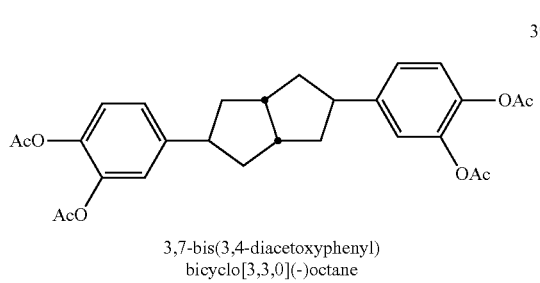

1,4-bis(3,4-diacetoxyphenyl)
cyclohexane

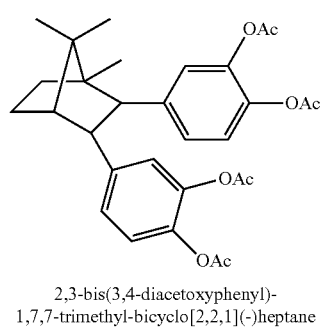

3,7-bis(3,4-diacetoxyphenyl)
bicyclo[3,3,0](-)octane

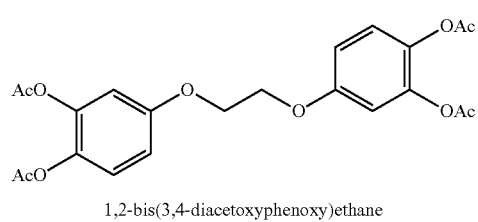

2,3-bis(3,4-diacetoxyphenyl)-
1,7,7-trimethyl-bicyclo[2,2,1](-)heptane

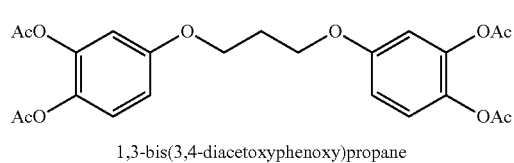

1,2-bis(3,4-diacetoxyphenoxy)ethane

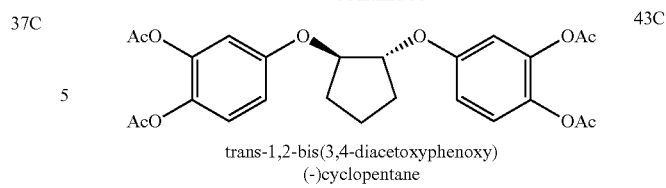

1,3-bis(3,4-diacetoxyphenoxy)propane

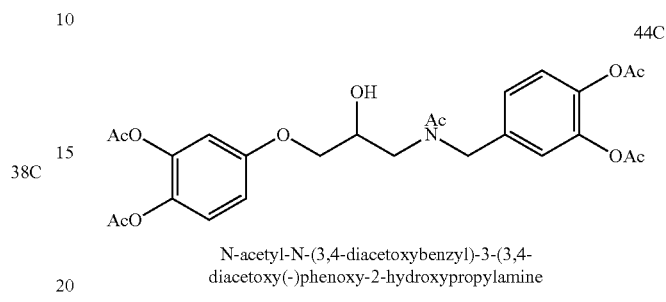

trans-1,2-bis(3,4-diacetoxyphenoxy)
(-)cyclopentane

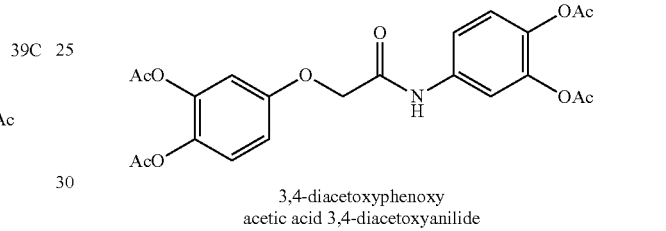

N-acetyl-N-(3,4-diacetoxybenzyl)-3-(3,4-
diacetoxy(-)phenoxy-2-hydroxypropylamine

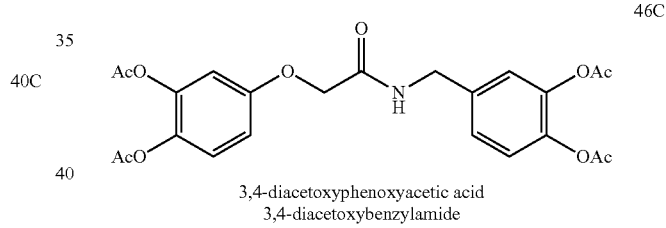

3,4-diacetoxyphenoxy
acetic acid 3,4-diacetoxyanilide

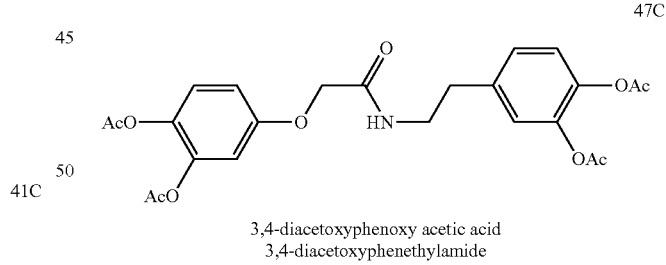

3,4-diacetoxyphenoxyacetic acid
3,4-diacetoxybenzylamide

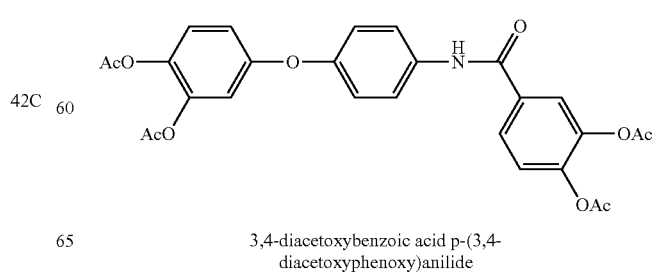

3,4-diacetoxyphenoxy acetic acid
3,4-diacetoxyphenethylamide 3,4-diacetoxybenzoic acid p-(3,4-
diacetoxyphenoxy)anilide

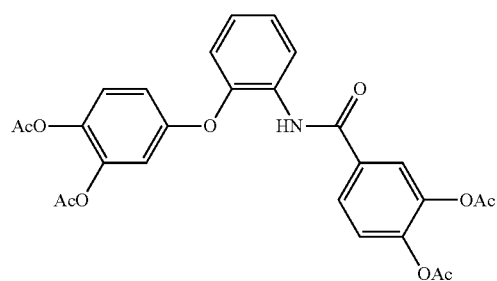

3,4-diacetoxybenzoic acid
o-(3,4-diacetoxyphenoxy)anilide

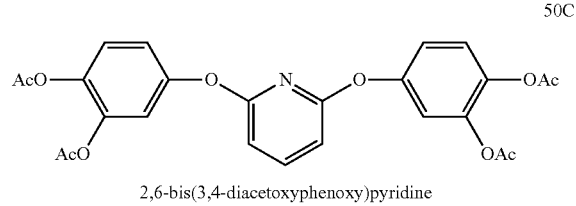

2,6-bis(3,4-diacetoxyphenoxy)pyridine

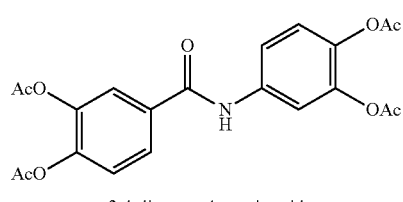

3,4-diacetoxybenzoic acid
3,4-diacetoxyanilide

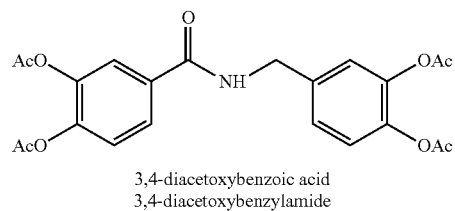

3,4-diacetoxybenzoic acid
3,4-diacetoxybenzylamide

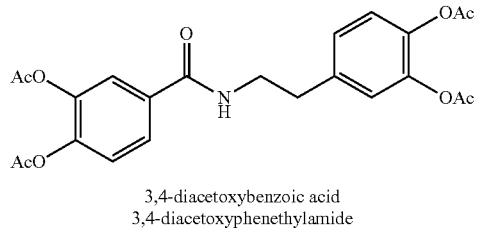

3,4-diacetoxybenzoic acid
3,4-diacetoxyphenethylamide

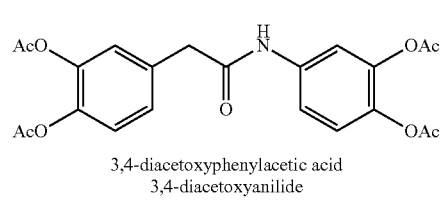

3,4-diacetoxyphenylacetic acid
3,4-diacetoxyanilide

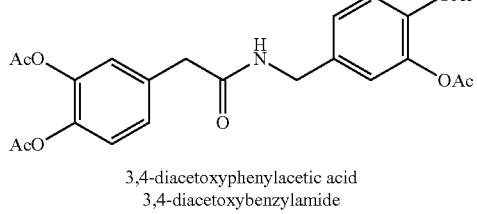

3,4-diacetoxyphenylacetic acid
3,4-diacetoxybenzylamide

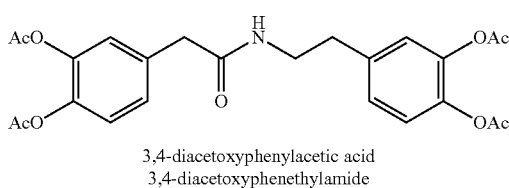

3,4-diacetoxyphenylacetic acid
3,4-diacetoxyphenethylamide

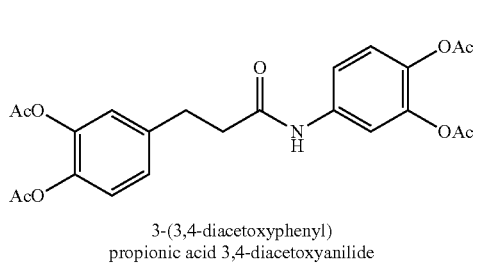

3-(3,4-diacetoxyphenyl)
propionic acid 3,4-diacetoxyanilide

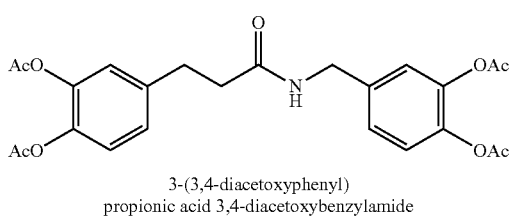

3-(3,4-diacetoxyphenyl)
propionic acid 3,4-diacetoxybenzylamide

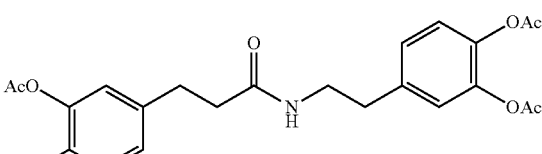

3-(3,4-diacetoxyphenyl)propionic
acid 3,4-diacetoxyphenethylamide

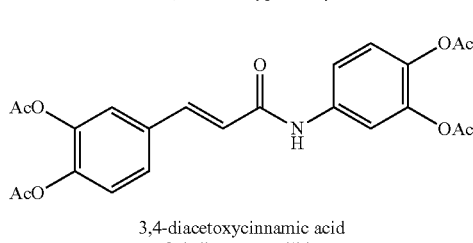

3,4-diacetoxycinnamic acid
3,4-diacetoxyanilide

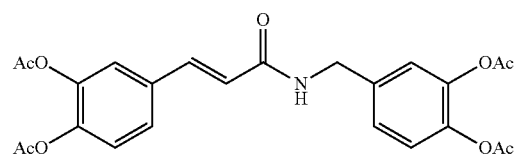

3,4-diacetoxycinnamic acid
3,4-diactoxybenzylamide
61C

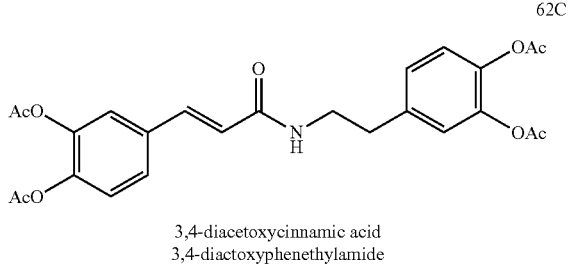

3,4-diacetoxycinnamic acid
3,4-diactoxyphenethylamide
62C

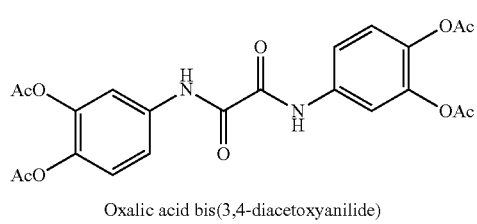

Oxalic acid bis(3,4-diacetoxyanilide)
63C

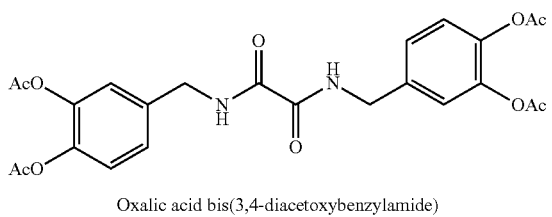

Oxalic acid bis(3,4-diacetoxybenzylamide)
64C

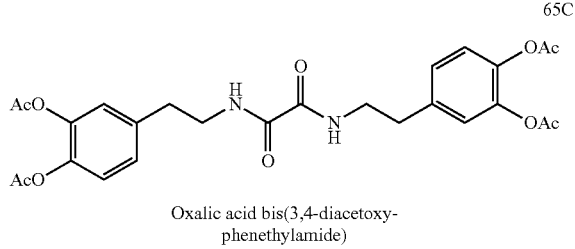

Oxalic acid bis(3,4-diacetoxy-phenethylamide)
65C

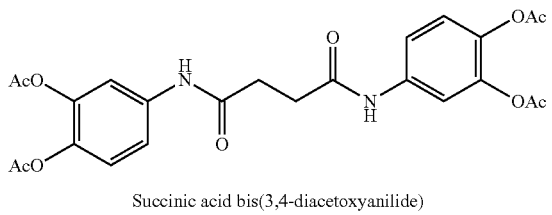

Succinic acid bis(3,4-diacetoxyanilide)
66C

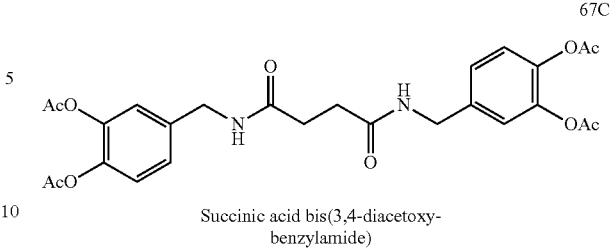

Succinic acid bis(3,4-diacetoxy-benzylamide)
67C

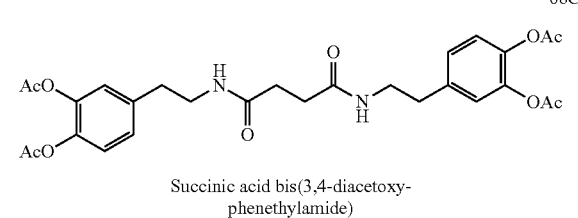

Succinic acid bis(3,4-diacetoxy-phenethylamide)
68C

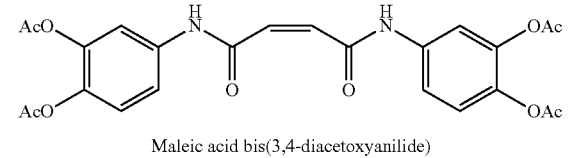

Maleic acid bis(3,4-diacetoxyanilide)
69C

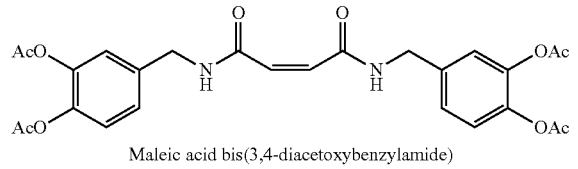

Maleic acid bis(3,4-diacetoxybenzylamide)
70C

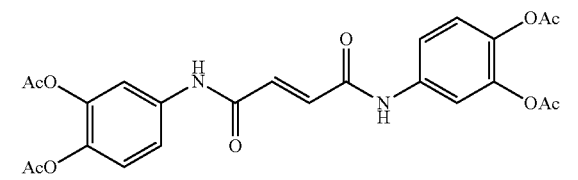

Fumaric acid bis-(3,4-diacetoxy-anilide)
71C

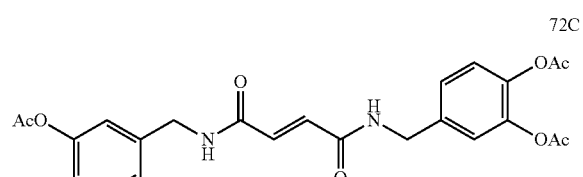

Fumaric acid bis-(3,4-diacetoxy-benzylamide)
72C

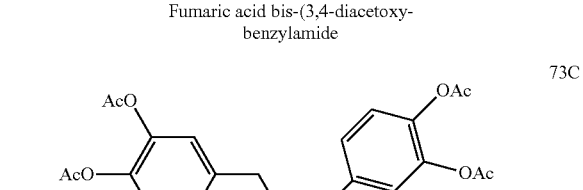
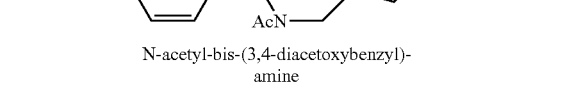

N-acetyl-bis-(3,4-diacetoxybenzyl)-amine
73C

-continued

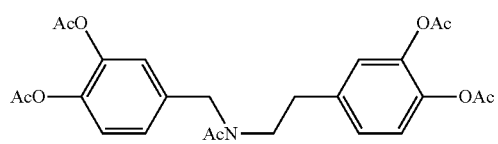

N-acetyl-N-(3,4-diacetoxybenzyl)-
3,4-diacetoxyphenethylamine

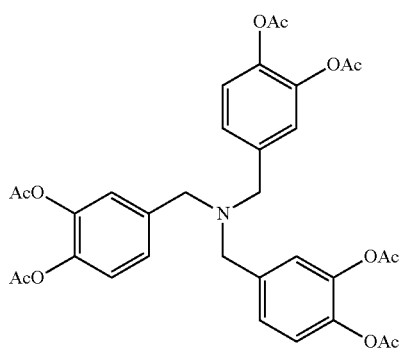

tris-(3,4-diacetoxybenzyl)-amine

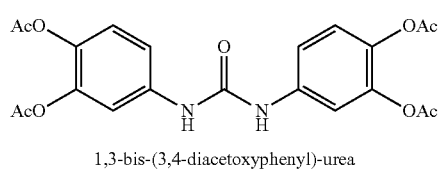

1,3-bis-(3,4-diacetoxyphenyl)-urea

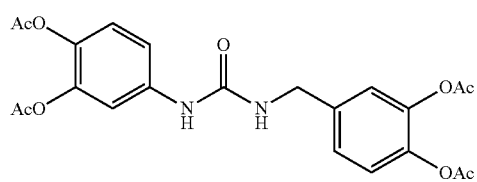

1-(3,4-diaceetoxyphenyl)-3-
(3,4-diacetoxybenzyl) urea

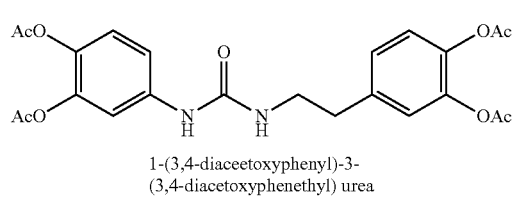

1-(3,4-diaceetoxyphenyl)-3-
(3,4-diacetoxyphenethyl) urea

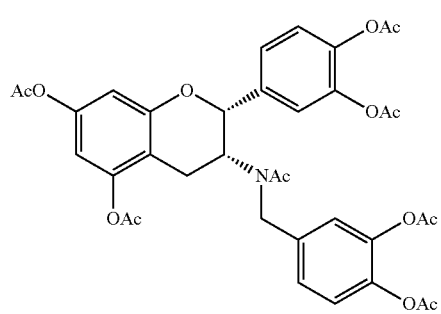

N-acetyl-3-deoxy-3-(3,4-diacetoxy-
benzyl)-amino-5,7,3′,4′-tetraacetyl-
epicatechin -continued

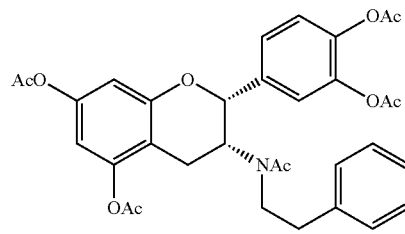

N-acetyl-3-deoxy-3-(3,4-diacetoxy-
phenethyl)-amino-5,7,3′,4′-tetraacetyl-
epicatechin

Example 5

Pharmaceutical Formulations

Compositions of Compounds of this Invention.

The compounds of this invention, as mentioned previously, are desirably administered in the form of pharmaceutical compositions. Suitable pharmaceutical compositions, and the method of preparing them, are well-known to persons of ordinary skill in the art and are described in such treatises as *Remington: The Science and Practice of Pharmacy*, A. Gennaro, ed., 20th edition, Lippincott, Williams & Wilkins, Philadelphia, Pa.

Representative compositions are as follows:

Oral Tablet Formulation

An oral tablet formulation of a compound of this invention is prepared as follows:

|  | % w/w |
|---|---|
| Compound of this invention | 10.0 |
| Magnesium stearate | 0.5 |
| Starch | 2.0 |
| Hydroxypropylmethylcellulose | 1.0 |
| Microcrystalline cellulose | 86.5 |

The ingredients are mixed to homogeneity, then granulated with the aid of water, and the granulates dried. The granulate is then compressed into tablets sized to give a suitable dose of the compound. The tablet is optionally coated by applying a suspension of a film forming agent (e.g. hydroxypropylmethylcellulose), pigment (e.g. titanium dioxide), and plasticizer (e.g. diethyl phthalate), and drying the film by evaporation of the solvent. The film coat may comprise, for example, 2-6% of the tablet weight.

Oral Capsule Formulation

The granulate from the previous section of this Example is filled into hard gelatin capsules of a size suitable to the intended dose. The capsule is banded for sealing, if desired.

Softgel Formulation

A softgel formulation is prepared as follows:

|  | % w/w |
|---|---|
| Compound of this invention | 20.0 |
| Polyethylene glycol 400 | 80.0 |

The compound is dissolved or dispersed in the polyethylene glycol, and a thickening agent added if required. A quantity of the formulation sufficient to provide the desired dose of the compound is then filled into softgels.

Parenteral Formulation

A parenteral formulation is prepared as follows:

|  | % w/w |
|---|---|
| Compound of this invention | 1.0 |
| Normal saline | 99.0 |

The compound is dissolved in the saline, and the resulting solution is sterilized and filled into vials, ampoules, and pre-filled syringes, as appropriate.

Controlled-Release Oral Formulation

A sustained release formulation may be prepared by the method of U.S. Pat. No. 4,710,384, as follows:

One Kg of a compound of this invention is coated in a modified Uni-Glatt powder coater with Dow Type 10 ethyl cellulose. The spraying solution is an 8% solution of the ethyl cellulose in 90% acetone to 10% ethanol. Castor oil is added as plasticizer in an amount equal to 20% of the ethyl cellulose present. The spraying conditions are as follows: 1) speed, 1 liter/hour; 2) flap, 10-15%; 3) inlet temperature, 50° C., 4) outlet temperature, 30° C., 5) percent of coating, 17%. The coated compound is sieved to particle sizes between 74 and 210 microns. Attention is paid to ensure a good mix of particles of different sizes within that range. Four hundred mg of the coated particles are mixed with 100 mg of starch and the mixture is compressed in a hand press to 1.5 tons to produce a 500 mg controlled release tablet.

Example 6

No Release Inhibition by Bis- and Tris-Dihydroxyaryl Compounds

The purpose of this experiment was to screen compounds 3, 4, 21, 26, 51, 52, 66, and 78 for their ability to inhibit Nitric oxide release from microglia. Previous experiments demonstrated the ability of some compounds to inhibit NO release from LPS/IFNγ stimulated microglia. EOC 13.31 microglia cells were plated into 96 well plates for 24 hours. Confluent cells were treated with 50 μM of the bis- and tris-dihydroxyaryl compounds either with or without stimulation at 1 pg/ml LPS, and 1 ng/ml IFNγ. NO release was measured at 24 hours using the Griess reaction which is a spectrophotometric measure of NO release (reagents from Promega).

TABLE 1

Inhibition of NO release from microglia exposed to LPS/IFNγ treated with bis- and tris-dihydroxyaryl compounds

|  | Compound Only | Compound and LPS/IFNγ | % inhibition |
|---|---|---|---|
| Media control | 1.0979 | 18.6224 | — |
| 3 | 1.0417 | 9.5299 | 48.8% |
| 4 | 0.8660 | 1.0417 | 94.4% |
| 21 | −0.0417 | 15.3486 | 17.6% |
| 26 | 0.0000 | 14.8384 | 20.3% |
| 51 | 1.2500 | 20.6633 | −11.0% |
| 52 | −0.0417 | 16.2840 | 12.6% |
| 66 | 0.8333 | 15.4762 | 16.9% |
| 78 | 1.1667 | 18.7925 | −0.9% |
| L-NAME* | 1.4512 | 6.9568 | 62.6% |

*L-NAME (nitro-L-arginine methyl ester) is a positive control for NO inhibition

NO was not detected in cells not exposed to LPS/IFNγ. Exposure of cells only to 1 mg/ml LPS and 1 ng/ml IFNγ induced NO release to 18.6 uM. Concurrent treatment with bis- and tris-dihydroxyaryl compound inhibited NO release as set out in table 2. Bis- and tris-dihydroxyaryl compounds 3, 4 and 26 were very effective inhibitors of NO release by LPS/IFNγ stimulated microglial cells. Specifically compound 4 caused a significant, (p<0.001) 94.4% inhibition.

TABLE 2

Summary of Inhibition of NO release from microglia exposed to LPS/IFNγ treated with bis- and tris-dihydroxyaryl compounds

| Compound | % Inhibition of NO release |
|---|---|
| 3 | 48.8% |
| 4 | 94.4% |
| 21 | 17.6% |
| 26 | 20.3% |
| 51 | −11% |
| 52 | 12.6% |
| 66 | 16.9% |
| 78 | −0.9% |
| L-name (+control) | 62.6% |

Example 7

Inhibition of NO Release by Bis- and Tris-Dihydroxyaryl Compounds

In this experiment, additional bis- and tris-dihydroxyaryl compounds were screened for their ability to inhibit nitric oxide release from microglial cells. Microglial cells stimulated with LPS/IFNγ release nitric oxide. Previous experiments suggest some bis- and tris-dihydroxyaryl compounds block NO release. This is a continuation of screening experiments. EOC 13.31 microglial cells were plated into 96 well plates. At 24 hours and at confluency, cells were treated with 10 μg/ml LPS/10 ng/ml IFNγ+50 uM bis- and tris-dihydroxyaryl compounds. NO release was measured by using the Griess reaction at 48 hours and is shown in Table 3.

TABLE 3

NO release from microglia

| Compound | μM NO release | Avgerage % Inhibition |
|---|---|---|
| Untreated | 3.782 | — |
| 67 | 10.579 | 60.85 |
| 63 | 23.193 | 14.16 |
| 61 | 21.285 | 21.22 |
| 23 | 23.394 | 13.42 |
| 19 | 25.828 | 4.41 |
| 9 | 26.299 | 2.66 |
| 8 | 25.265 | 6.49 |
| 1 | 22.038 | 18.43 |
| L-NAME* | 2.288 | 91.53 |
| LPS | 27.019 | — |
| Untreated | 4.782 | — |
| 77 | 24.398 | 12.06 |
| 58 | 26.605 | 4.10 |
| 75 | 23.343 | 15.86 |
| 57 | 23.756 | 14.37 |
| 12 | 18.976 | 31.60 |
| 76 | 23.745 | 14.41 |
| 73 | 2.301 | 91.71 |
| 85 | 23.445 | 15.49 |

TABLE 3-continued

NO release from microglia

| Compound | µM NO release | Avgerage % Inhibition |
|---|---|---|
| 3 | 1.000 | 96.40 |
| LPS | 27.743 | |

*Positive control

From this experiment, 3, 12, 61, 67 and 73 were compounds that demonstrated the most dramatic effect. L-NAME treated cells appeared exactly like cells that weren't exposed to LPS/IFNγ. Compounds 3, 12, 61, 67 and 73 were effective inhibitors of NO release by LPS/IFNγ stimulated microglia.

Example 8

Dose Response Inhibition of NO Release from Microglia by Bis- and Tris-Dihydroxyaryl Compounds This experiment was designed to determine dose response inhibition of NO release from microglia by bis- and tris-dihydroxyaryl compounds when stimulated with LPS/IFNγ. Earlier experiments demonstrated that some bis- and tris-dihydroxyaryl compounds are good inhibitors of NO release from microglia. This experiment is designed to determine a dose response for various bis- and tris-dihydroxyaryl compounds. Microglial cells were plated into 96 well plates at $1 \times 10^5$ cells/ml. At 48 hours, media was exchanged for media containing 10 ng/ml IFNγ and 10 µg/ml LPS and the following compounds 3, 4, 21, 26 and the positive control L-NAME were used. The doses tested were: 0.75 µM, 1.56 µM, 3.125 µM, 6.25 µM, 12.5 µM, 25 µM, 50 µM, 100 µM and 200 µM. Nitric oxide release was measured after 48 hours using the Griess reaction.

TABLE 4

Dose response

| Compound | Dose µm | Average µM NO release | Avg % Inhibition |
|---|---|---|---|
| 3 | LPS | 19.792 | — |
| | 0.75 | 21.563 | -8.947 |
| | 1.56 | 19.792 | 0.000 |
| | 3.125 | 19.635 | 0.789 |
| | 6.25 | 18.333 | 7.368 |
| | 12.5 | 18.490 | 6.579 |
| | 25 | 16.875 | 14.737 |
| | 50 | 10.417 | 47.368 |
| | 100 | 7.448 | 62.368 |
| | 200 | 6.510 | 67.105 |
| 4 | LPS | 24.323 | — |
| | 0.75 | 27.011 | -11.054 |
| | 1.56 | 23.709 | 2.525 |
| | 3.125 | 22.829 | 6.143 |
| | 6.25 | 15.521 | 36.188 |
| | 12.5 | 4.208 | 82.698 |
| | 25 | 3.357 | 86.197 |
| | 50 | 3.292 | 86.467 |
| | 100 | 4.333 | 82.184 |
| | 200 | 6.000 | 75.332 |
| 21 | LPS | 19.792 | — |
| | 0.75 | 22.865 | -15.526 |
| | 1.56 | 21.094 | -6.579 |
| | 3.125 | 20.990 | -6.053 |
| | 6.25 | 20.156 | -1.842 |
| | 12.5 | 18.802 | 5.000 |
| | 25 | 19.219 | 2.895 |
| | 50 | 17.083 | 13.684 |
| | 100 | 13.125 | 33.684 |
| | 200 | 6.094 | 69.211 |
| 26 | LPS | 24.323 | — |
| | 0.75 | 24.756 | -1.780 |
| | 1.56 | 22.865 | 5.996 |
| | 3.125 | 22.917 | 5.782 |
| | 6.25 | 24.219 | 0.428 |
| | 12.5 | 21.875 | 10.064 |
| | 25 | 21.875 | 10.064 |
| | 50 | 19.531 | 19.700 |
| | 100 | 18.594 | 23.555 |
| | 200 | 13.490 | 44.540 |
| L-name | LPS | 22.292 | — |
| | 0.75 | 23.542 | -5.607 |
| | 1.56 | 22.448 | -0.701 |
| | 3.125 | 21.563 | 3.271 |
| | 6.25 | 19.583 | 12.150 |
| | 12.5 | 16.615 | 25.467 |
| | 25 | 13.594 | 39.019 |
| | 50 | 9.531 | 57.243 |
| | 100 | 6.292 | 71.776 |
| | 200 | 4.500 | 79.813 |

Compounds 3, 4, 21, and to a lesser extent 26 were effective inhibitors of NO release. At the highest concentration tested (200 µM), compounds 3, 4, and 21 inhibited NO release by 67%, 75%, and 69% respectively.

Example 9

Dose Response Inhibition of NO Release from Microglia by Bis- and Tris-Dihydroxyaryl Compounds This experiment was designed to determine the dose response inhibition of NO release from microglia by bis- and tris-dihydroxyaryl compounds when stimulated with LPS/IFNγ. Earlier experiments have demonstrated that some bis- and tris-dihydroxyaryl compounds are good inhibitors of NO release from microglia. This experiment is designed to determine a dose response for various effective bis- and tris-dihydroxyaryl compounds. Microglial cells were plated into 96 well plates at $1 \times 10^5$ cells/ml. At 48 hours, media was exchanged for media containing 10 ng/ml IFNγ and 10 µg/ml LPS and the following compounds 3, 4, 21, 26 and the positive control L-NAME. The doses tested were: 0.5 µM, 1.0 µM, 5.0 µM, 10 µM, 25 µM, 50 µM, 100 µM, 250 µM, and 500 µM. Nitric oxide release was measured after 48 hours using the Griess reaction.

TABLE 5

Dose Response

| | Average % Inhibition |
|---|---|
| Compound 21 | |
| 0.5 | -0.76% |
| 1 | 1.01% |
| 5 | 0.76% |
| 10 | -1.27% |
| 25 | 4.82% |
| 50 | 13.19% |
| 100 | 35.25% |
| 250 | 83.51% |
| 500 | 80.28% |

TABLE 5-continued

Dose Response

| Compound 26 | Average % Inhibition |
|---|---|
| 0.5 | −4.06% |
| 1 | 0.51% |
| 5 | −4.31% |
| 10 | −1.01% |
| 25 | 6.85% |
| 50 | 6.59% |
| 100 | 16.23% |
| 250 | 35.25% |
| 500 | 99.51% |
| Compound 67 | |
| 0.5 | −2.75% |
| 1 | 1.50% |
| 5 | −0.75% |
| 10 | −12.74% |
| 25 | −5.50% |
| 50 | −9.24% |
| 100 | 15.99% |
| 250 | 44.35% |
| 500 | 76.91% |
| Compound 73 | |
| 0.5 | 12.74 |
| 1 | 16.49 |
| 5 | 1.50 |
| 10 | 1.75 |
| 25 | 0.75 |
| 50 | 0.25 |
| 100 | 32.98 |
| 250 | 45.27 |
| 500 | 72.34 |
| L-name | |
| 0.5 | 24.74 |
| 1 | 29.19 |
| 5 | 38.81 |
| 10 | 40.07 |
| 25 | 65.03 |
| 50 | 80.53 |
| 100 | 81.74 |
| 250 | 94.02 |
| 500 | 96.73 |

All of the compounds tested were effective inhibitors of NO release. At the highest concentration tested (500 µM), compounds 26, 67, and 73 inhibited NO release by 99%, 76%, and 72% respectively. Compound 21 was most effective at the 250 µM dose.

Example 10

Inhibition of NO Release from Microglia following Pretreatment with Bis- and Tris-Dihydroxyaryl Compounds This experiment was designed to determine if pretreatment for 24 hours with bis- and tris-dihydroxyaryl compounds changes NO inhibition previously observed with concurrent exposure of bis- and tris-dihydroxyaryl compounds. Previous screens demonstrated significant inhibition by different bis- and tris-dihydroxyaryl compounds of LPS/IFNγ induced nitric oxide release by microglial cells. This study seeks to determine if pretreatment with bis- and tris-dihydroxyaryl compounds increases NO release inhibition. EOC 13.31 microglia cells were plated at $1\times10^6$ cells/ml in 96 well plates. After 48 hours, confluent cells were exposed to 50 µM compound (stock 10 mM in DMSO) prepared in fresh cell culture media. After 24 hours, 10 µg/ml LPS and 10 ng/ml IFNγ was added to wells directly without a media change. Cells were incubated for a further 48 hours and nitric oxide release was measured using the Griess Reaction.

TABLE 6

Pretreatment and inhibition of NO release

| 50 uM Compound | Average % Inhibition |
|---|---|
| 4 | 100.00% |
| 73 | 100.00% |
| 57 | 100.00% |
| 77 | 96.85% |
| 85 | 94.94% |
| 21 | 83.88% |
| 19-2 | 82.93% |
| 63 | 82.08% |
| 52 | 79.97% |
| 3 | 79.87% |
| 76 | 76.28% |
| 58 | 72.48% |
| 67 | 65.63% |
| 78 | 65.52% |
| 66 | 64.26% |
| 51-S1 | 60.14% |
| 75 | 59.62% |
| 51 | 56.03% |
| L-NAME* | 100.00% |
| LPS/IFN | — |

*Positive control

Pretreatment with bis- and tris-dihydroxyaryl compounds significantly inhibited NO release. All of the compounds tested showed inhibition of NO release by at least 55%. Specifically, compounds 4, 73, 57, 77, 85, 21, 19, 63, 52, 3, and 76 showed greater than 75% inhibition of NO release following pretreatment.

Example 11

TNF-A Inhibition by Bis- and Tris-Dihydroxyaryl Compounds

This experiment was designed to determine if bis- and tris-dihydroxyaryl compounds inhibit TNF-α release from microglia immunostimulated with LPS and IFNγ. Previous experiments demonstrated significant TNF-α release from microglia stimulated with LPS and IFNγ. Also, bis- and tris-dihydroxyaryl compound's ability to inhibit NO release strongly supports their interference with the inflammatory cascade and ultimately inhibition of inflammation. Microglia cells were plated at 1×10 cells/ml into 96 well plates. At day three, they were treated with 50 µM bis- and tris-dihydroxyaryl compound for 1 hour and then exposed to 10 µg/ml LPS+10 ng/ml IFNγ for 24 hours. 10 µl of media was removed and stored at −80° C. until TNF-α ELISA assays were performed. Samples were diluted 1:50 before running the TNF-α ELISA (kit commercially available from Sigma).

TABLE 7

TNF-α release from microglia treated with bis- and tris-dihydroxyaryl compounds and 10 ug LPS and 10 ng IFNγ

| Compound | Average % Inhibition |
|---|---|
| No LPS | — |
| 51-1 | −14.64% |
| 51-4 | −16.24% |
| 51-S1 | −11.55% |
| 51-S3 | −9.64% |
| 51-S4 | −0.48% |

TABLE 7-continued

TNF-α release from microglia treated with bis- and tris-dihydroxyaryl compounds and 10 ug LPS and 10 ng IFNγ

| Compound | Average % Inhibition |
|---|---|
| 51-S5 | 55.05% |
| 51-S6 | −0.27% |
| 51-S7 | −13.53% |
| 51-S8 | −21.83% |
| 51-S9 | 44.58% |
| 3-2 | 29.41% |
| 4-3 | 89.89% |
| 73 | −45.90% |
| 67 | −19.65% |
| 12 | 17.20% |
| LPS | — |
| No LPS | — |
| 61 | −9.32 |
| 26 | −16.82 |
| 1 | −17.26 |
| 21-2 | −23.18 |
| 66-2 | −13.70 |
| 75 | 1.86 |
| 85 | −16.77 |
| 76-2 | −9.81 |
| 57 | −3.89 |
| 63 | −9.48 |
| 23 | −19.18 |
| 52 | −23.18 |
| 77-1 | 2.58 |
| 8-1 | 92.47 |
| 19-2 | 9.42 |
| 58 | −12.60 |
| LPS | — |

*S numbers indicate analogs and numerals after dashes indicate synthetic batch numbers.

Dexamethasone, the positive control, demonstrated 72.4% inhibition. Some of the bis- and tris-dihydroxyaryl compounds like 51-S5 (55% inhibition), 51-S9 (44% inhibition), 4-3 (89% inhibition) and 8-1 (92% inhibition) were good inhibitors of TNF-α release indicating that the compounds are also good inhibitors of the inflammatory cascade.

Example 12

Ranking of NO Release Inhibition

The bis- and tris-dihydroxyaryl compounds were ranked in order of effectiveness for the inhibition of NO release as set out in Table 8.

TABLE 8

Ranking of effectiveness of compounds for the inhibition of NO release.

| Compound | % Inhibition at 50 µM |
|---|---|
| 4 | 94 |
| 8 | 92 |
| 67 | 61 |
| 12 | 32 |
| 3 | 30 |
| 61 | 21 |
| 26 | 20 |
| 1 | 18 |
| 21 | 18 |
| 66 | 17 |
| 75 | 16 |
| 85 | 16 |
| 76 | 14 |
| 57 | 14 |
| 63 | 14 |
| 23 | 13 |

TABLE 8-continued

Ranking of effectiveness of compounds for the inhibition of NO release.

| Compound | % Inhibition at 50 µM |
|---|---|
| 52 | 13 |
| 77 | 12 |
| 19 | 4 |
| 58 | 4 |
| 9 | 3 |
| 73 | 2 |
| 78 | −1 |
| L-NAME | 92 |

The present invention is not limited in scope by the specific embodiments described herein. Indeed, various modifications of the invention in addition to those described will become apparent to those skilled in the art from the foregoing descriptions. Such modifications are intended to fall within the scope of the appended claims. Various publications are cited herein, the disclosures of which are incorporated by reference in their entireties.

We claim:

1. A method of inhibiting the inflammatory process, the method comprising administering to a mammal suffering from inflammation a therapeutically effective amount of a pharmaceutical composition comprising a compound

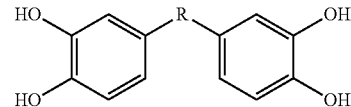

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by $NR^1$ (where $R^1$ is H, alkyl, or acyl), O, or S; and 1 or 2 methylene groups are optionally replaced by a carbonyl or hydroxymethylene group, with the proviso that if R is unsaturated then the carbonyl is not adjacent to either aromatic ring, and pharmaceutically acceptable esters or salts of the compounds.

2. The method of claim 1 where the compound is selected from the group consisting of:
3,4,3',4'-tetrahydroxybenzoin (compound 1);
3,4,3',4'-tetrahydroxydesoxybenzoin (compound 2);
3,4,3',4'-tetrahydroxydiphenylmethane (compound 3);
1,2-bis(3,4-dihydroxyphenyl)ethane (compound 4);
1,3-bis(3,4-dihydroxyphenyl)propane (compound 5);
N,N'-bis(3,4-dihydroxybenzyl)-N,$N^1$-dimethylethylenediamine (compound 10);
N,N'-bis(3,4-dihydroxybenzoyl)-N,N'-dimethylethylenediamine (compound 24);
1,2-bis(3,4-dihydroxyphenoxy)ethane (compound 41);
1,3-bis(3,4-dihydroxyphenoxy)propane (compound 42);
N-(3,4-dihydroxybenzyl)-3-(3,4-dihydroxyphenoxy)-2-hydroxyropylamine (compound 44);
3,4-dihydroxyphenoxyacetic acid 3,4-dihydroxyanilide (compound 45);
3,4-dihydroxyphenoxyacetic acid 3,4-dihydroxybenzylamide (compound 46);
3,4-dihydroxyphenoxyacetic acid 3,4-dihydroxyphenethylamide (compound 47);

3,4-dihydroxybenzoic acid 3,4-dihydroxyanilide (compound 51);
3,4-dihydroxybenzoic acid 3,4-dihydroxybenzylamide (compound 52);
3,4-dihydroxybenzoic acid 3,4-dihydroxyphenethylamide (compound 53);
3,4-dihydroxyphenylacetic acid 3,4-dihydroxyanilide (compound 54);
3,4-dihydroxyphenylacetic acid 3,4-dihydroxybenzylamide (compound 55);
3,4-dihydroxyphenylacetic acid 3,4-dihydroxyphenethylamide (compound 56);
3-(3,4-dihydroxyphenyl)propionic acid 3,4-dihydroxyanilide (compound 57);
3-(3,4-dihydroxyphenyl)propionic acid 3,4-dihydroxybenzaylamide (compound 58);
3-(3,4-dihydroxyphenyl)propionic acid 3,4-dihydroxyphenethylamide (compound 59);
3,4-dihydroxycinnamic acid 3,4-dihydroxyanilide (compound 60);
3,4-dihydroxycinnamic acid 3,4-dihydroxybenzylamide (compound 61);
3,4-dihydroxycinnamic acid 3,4-dihydroxyphenethylamide (compound 62);
oxalic acid bis(3,4-dihydroxyanilide) (compound 63);
oxalic acid bis(3,4-dihydroxybenzylamide) (compound 64);
oxalic acid bis(3,4-dihydroxyphenethylamide) (compound 65);
succinic acid bis(3,4-dihydroxyanilide) (compound 66);
succinic acid bis(3,4-dihydroxybenzylamide) (compound 67);
succinic acid bis(3,4-dihydroxyphenethylamide) (compound 68);
maleic acid bis(3,4-dihydroxyanilide) (compound 69);
maleic acid bis(3,4-dihydroxyanilide) (compound 70);
fumaric acid bis(3,4-dihydroxyanilide) (compound 71);
fumaric acid bis(3,4-dihydroxybenzylamide) (compound 72);
bis(3,4-dihydroxybenzyl)amine (compound 73);
N(3,4-dihydroxybenzyl)-3,4-dihydroxyphenethylamine (compound 74);
1,3-bis(3,4-dihydroxybenzyl)urea (compound 76);
1-(3,4-dihydroxyphenyl)-3-(3,4-dihydroxybenzyl)urea (compound 77);
1-(3,4-dihydroxybenzyl)-3-(3,4-dihydroxyphenethyl)urea (compound 78);
and methylenedioxy analogs and pharmaceutically acceptable esters or salts of the compounds.

3. The method of claim 1 where the mammal is human.

4. The method of claim 1 where the therapeutically effective amount of the pharmaceutical composition is from 0.1-1000 mg/Kg body weight/day.

5. The method of claim 1 where the therapeutically effective amount of the pharmaceutical composition is from 1-100 mg/Kg body weight/day.

6. The method of claim 1 where the therapeutically effective amount of the pharmaceutical composition is from 10-100 mg/Kg body weight/day.

7. The method of claim 1 wherein the inflammatory process results from a disease selected from the group consisting of ulcerative colitis, endotoxic shock, rheumatoid arthritis, juvenile arthritis, osteoarthritis, psoriasis, Crohn's disease, inflammatory bowel disease, multiple sclerosis, insulin dependent diabetes mellitus, gout, psoriatic arthritis, reactive arthritis, viral or post-viral arthritis and ankylosing spondylarthritis.

8. The method of claim 7 wherein the inflammatory process results from rheumatoid arthritis.

9. The method of claim 1 where the pharmaceutical composition additionally comprises one or more pharmaceutically acceptable excipients.

* * * * *